(12) United States Patent
Yoshida et al.

(10) Patent No.: US 9,848,772 B2
(45) Date of Patent: Dec. 26, 2017

(54) IMAGE DISPLAYING METHOD

(71) Applicants: KABUSHIKI KAISHA TOPCON, Itabashi (JP); National University Corporation ASAHIKAWA MEDICAL UNIVERSITY, Asahikawa-shi (JP)

(72) Inventors: Akitoshi Yoshida, Asahikawa (JP); Masahiro Akiba, Toda (JP); Yasufumi Fukuma, Wako (JP); Hideaki Tokoro, Kazo (JP); Taiki Aimi, Musashino (JP); Shunsuke Nakamura, Kita-ku (JP)

(73) Assignees: KABUSHIKI KAISHA TOPCON, Itabashi-ku (JP); National University Corporation ASAHIKAWA MEDICAL UNIVERSITY, Asahikawa-shi (JP)

( * ) Notice: Subject to any disclaimer, the term of this patent is extended or adjusted under 35 U.S.C. 154(b) by 0 days.

(21) Appl. No.: 15/197,282

(22) Filed: Jun. 29, 2016

(65) Prior Publication Data

US 2016/0310024 A1   Oct. 27, 2016

Related U.S. Application Data

(62) Division of application No. 14/379,623, filed as application No. PCT/JP2013/056495 on Mar. 8, 2013, now Pat. No. 9,492,082.

(30) Foreign Application Priority Data

Mar. 12, 2012  (JP) ................................ 2012-053911
Mar. 29, 2012  (JP) ................................ 2012-076741

(51) Int. Cl.
*A61B 5/05*   (2006.01)
*A61B 3/12*   (2006.01)
(Continued)

(52) U.S. Cl.
CPC ............ *A61B 3/1233* (2013.01); *A61B 3/102* (2013.01); *A61B 3/1241* (2013.01);
(Continued)

(58) Field of Classification Search
CPC ..... A61B 3/102; A61B 3/1233; A61B 3/1241; A61B 5/0066; A61B 5/026; A61B 5/0261;
(Continued)

(56) References Cited

U.S. PATENT DOCUMENTS

| 6,377,349 B1 | 4/2002 | Fercher |
| 7,345,770 B2 | 3/2008 | Chan et al. |

(Continued)

FOREIGN PATENT DOCUMENTS

| JP | 09-276232 | 10/1997 |
| JP | 11-325849 | 11/1999 |

(Continued)

OTHER PUBLICATIONS

International Search Report dated Apr. 2, 2013 in PCT/JP13/056495 Filed Mar. 8, 2013.

(Continued)

*Primary Examiner* — Mark Remaly
(74) *Attorney, Agent, or Firm* — Oblon, McClelland, Maier & Neustadt, L.L.P.

(57) ABSTRACT

In an embodiment, cross sectional image storage stores a cross sectional image group including multiple cross sectional images each of which is associated with time. Phase image storage stores a phase image group including multiple phase images each of which is associated with time. Blood flow information storage stores a blood flow information group including multiple blood flow information each of which is related to blood flow in a blood vessel of the living body and is associated with time. Display synchronously (Continued)

displays a cross sectional image included in the cross sectional image group and a phase image included in the phase image group using time associated with the cross sectional image and the phase image, and displays a blood flow image that expresses multiple blood flow information. The display performs the same change as the change to the cross sectional image, the phase image and the blood flow image.

3 Claims, 32 Drawing Sheets

(51) Int. Cl.
*A61B 5/00* (2006.01)
*G06T 11/60* (2006.01)
*A61B 5/0285* (2006.01)
*A61B 5/026* (2006.01)
*A61B 3/10* (2006.01)
*G01N 21/47* (2006.01)

(52) U.S. Cl.
CPC ............ *A61B 5/0066* (2013.01); *A61B 5/026* (2013.01); *A61B 5/0261* (2013.01); *A61B 5/0285* (2013.01); *A61B 5/489* (2013.01); *A61B 5/6821* (2013.01); *A61B 5/7278* (2013.01); *A61B 5/742* (2013.01); *A61B 5/743* (2013.01); *G01N 21/4795* (2013.01); *G06T 11/60* (2013.01); *G06T 2210/41* (2013.01)

(58) Field of Classification Search
CPC ..... A61B 5/0285; A61B 5/489; A61B 5/6821; A61B 5/7278; A61B 5/742; A61B 5/743; G01N 21/4795; G06T 11/60; G06T 2210/41
See application file for complete search history.

(56) References Cited

U.S. PATENT DOCUMENTS

| | | | |
|---|---|---|---|
| 8,244,334 B2 | 8/2012 | Huang et al. | |
| 8,733,933 B2 | 5/2014 | Hirose et al. | |
| 8,770,752 B2 | 7/2014 | Hirose et al. | |
| 2010/0041949 A1* | 2/2010 | Tolkowsky | A61B 1/0052 600/109 |
| 2011/0319775 A1 | 12/2011 | Fujii et al. | |
| 2012/0053904 A1 | 3/2012 | Yuasa et al. | |
| 2012/0120408 A1 | 5/2012 | Yasuno et al. | |

FOREIGN PATENT DOCUMENTS

| | | |
|---|---|---|
| JP | 2002-139421 | 5/2002 |
| JP | 2006-153838 | 6/2006 |
| JP | 2007-024677 | 2/2007 |
| JP | 2007-054251 | 3/2007 |
| JP | 2008-073099 | 4/2008 |
| JP | 2008-259544 | 10/2008 |
| JP | 2009-165710 | 7/2009 |
| JP | 2010-523286 | 7/2010 |
| JP | 2010-259698 | 11/2010 |
| JP | 2012-115572 | 6/2012 |
| JP | 2012-115573 | 6/2012 |
| WO | 2010/131550 | 11/2010 |
| WO | WO 2010/131531 | 11/2010 |
| WO | 2010/143601 | 12/2010 |

OTHER PUBLICATIONS

Extended European Search Report dated Jan. 11, 2017 in Patent Application No. 16176646.4.

* cited by examiner

FIG. 10
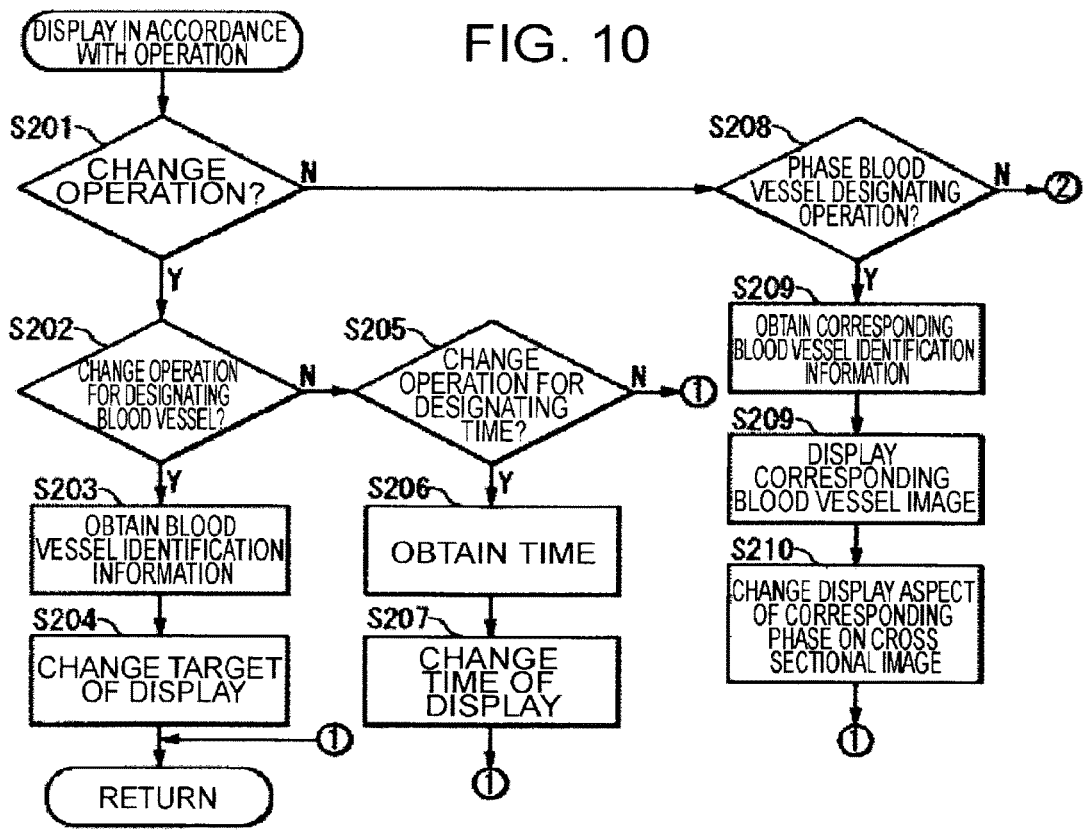
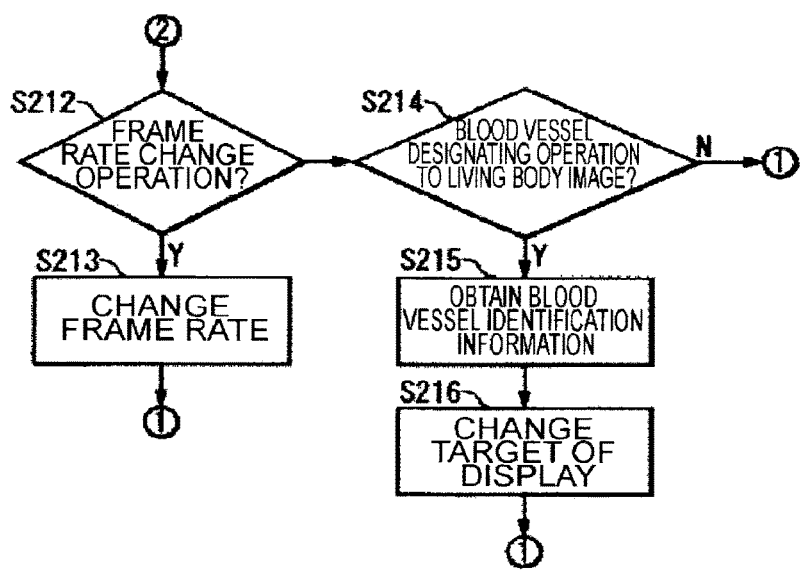

FIG. 13

| SUBJECT ID | LIVING BODY IMAGE GROUP ID | TIME CODE | LIVING BODY IMAGE |
|---|---|---|---|
| P10001 | E01 | t1 | |
| P10001 | E01 | t2 | |
| P10001 | E01 | t3 | |
| P10001 | E01 | t4 | |
| ...... | ...... | ...... | ...... |

FIG. 14

| SUBJECT ID | LIVING BODY IMAGE GROUP ID | TIME CODE | BLOOD VESSEL ID | BLOOD VESSEL LOCATION INFORMATION |
|---|---|---|---|---|
| P10001 | E01 | t1 | v01 | (x11,y11),(x12,y12),(x13,y13)… |
| P10001 | E01 | t1 | v02 | (x21,y21),(x22,y22),(x23,y23)… |
| P10001 | E01 | t1 | v03 | (x31,y31),(x32,y32),(x33,y33)… |
| P10001 | E01 | t1 | v04 | (x41,y41),(x42,y42),(x43,y43)… |
| … | … | … | … | … |
| P10001 | E01 | t2 | v01 | (x11,y11),(x12,y12),(x13,y13)… |
| P10001 | E01 | t2 | v02 | (x21,y21),(x22,y22),(x23,y23)… |
| … | … | … | … | … |

FIG. 16

| SUBJECT ID | CROSS SECTIONAL IMAGE GROUP ID | TIME CODE | CROSS SECTIONAL IMAGE |
|---|---|---|---|
| P10001 | D01 | t1 | |
| P10001 | D01 | t2 | |
| P10001 | D01 | t3 | |
| P10001 | D01 | t4 | |
| ...... | ...... | ...... | ...... |
| P10001 | D02 | t1 | |
| P10001 | D02 | t2 | |
| ...... | ...... | ...... | ...... |

FIG. 17

| SUBJECT ID | CROSS SECTIONAL IMAGE GROUP ID | TIME CODE | BLOOD VESSEL ID | CROSS SECTION BLOOD VESSEL LOCATION INFORMATION |
|---|---|---|---|---|
| P10001 | D01 | t1 | v01 | (x111,y111),(x112,y112),(x113,y113)... |
| P10001 | D01 | t1 | v02 | (x121,y121),(x122,y122),(x123,y123)... |
| P10001 | D02 | t1 | v03 | (x131,y131),(x132,y132),(x133,y133)... |
| P10001 | D03 | t1 | v04 | (x141,y141),(x142,y142),(x143,y143)... |
| ... | ... | ... | ... | |
| P10001 | D01 | t2 | v01 | (x111,y111),(x112,y112),(x113,y113)... |
| P10001 | D01 | t2 | v02 | (x121,y121),(x122,y122),(x123,y123)... |
| ... | ... | ... | ... | |

FIG. 19

| SUBJECT ID | PHASE IMAGE GROUP ID | TIME CODE | PHASE IMAGE |
|---|---|---|---|
| P10001 | F01 | t1 | ■ |
| P10001 | F01 | t2 | ■ |
| P10001 | F01 | t3 | ■ |
| P10001 | F01 | t4 | ■ |
| ...... | ...... | ...... | ...... |
| P10001 | F02 | t1 | ■ |
| P10001 | F02 | t2 | ■ |
| ...... | ...... | ...... | ...... |

FIG. 20

| SUBJECT ID | PHASE IMAGE GROUP ID | TIME CODE | BLOOD VESSEL ID | PHASE BLOOD VESSEL LOCATION INFORMATION |
|---|---|---|---|---|
| P10001 | F01 | t1 | v01 | (x111,y111),(x112,y112),(x113,y113)... |
| P10001 | F02 | t1 | v02 | (x121,y121),(x122,y122),(x123,y123)... |
| P10001 | F03 | t1 | v03 | (x131,y131),(x132,y132),(x133,y133)... |
| P10001 | F04 | t1 | v04 | (x141,y141),(x142,y142),(x143,y143)... |
| ... | ... | ... | ... | ... |
| P10001 | F01 | t2 | v01 | (x111,y111),(x112,y112),(x113,y113)... |
| P10001 | F02 | t2 | v02 | (x121,y121),(x122,y122),(x123,y123)... |
| ... | ... | ... | ... | ... |

FIG. 21

| SUBJECT ID | BLOOD FLOW INFORMATION GROUP ID | TIME CODE | BLOOD VESSEL ID | BLOOD FLOW INFORMATION |
|---|---|---|---|---|
| P10001 | B01 | t1 | v01 | s1 |
| P10001 | B02 | t1 | v02 | s2 |
| P10001 | B03 | t1 | v03 | s3 |
| P10001 | B04 | t1 | v04 | s4 |
| ... | ... | ... | ... | ... |
| P10001 | B01 | t2 | v01 | s5 |
| P10001 | B02 | t2 | v02 | s6 |
| ... | ... | ... | ... | ... |

FIG. 29

| SUBJECT ID | BLOOD VESSEL ID | BLOOD BESSEL CLASSIFICATION INFORMATION |
|---|---|---|
| P10001 | v05 | ARTERY |
| P10001 | v11 | ARTERY |
| P10001 | v08 | VEIN |
| P10001 | v01 | VEIN |
| P10001 | v02 | ARTERY |
| ... | ... | ... |

IMAGE DISPLAYING METHOD

CROSS-REFERENCE TO RELATED APPLICATION

This application is a divisional of and is based upon and claims the benefit of priority under 35 U.S.C. §120 for U.S. Ser. No. 14/379,623, filed Aug. 19, 2014, the entire contents of which are incorporation herein by reference. U.S. Ser. No. 14/379,623 is a National Stage of PCT/JP13/056495, filed Mar. 8, 2013, and claims the benefit of priority under U.S.C. §119 of Japanese Application No. 2012-053911, filed Mar. 12, 2012 and Japanese Application No. 2012-076741, filed Mar. 29, 2012.

TECHNICAL FIELD

The present invention relates to a blood flow measuring technology in which optical coherence tomography (OCT) is used.

BACKGROUND TECHNOLOGY

In recent years, OCT that forms images of the surface morphology and internal morphology of an object by using a light beam from a laser light source or the like has attracted attention. Unlike an X-ray CT apparatus, optical coherence tomography is noninvasive to human bodies, and is therefore expected to be utilized in the medical field and biological field. For example, in the ophthalmology, apparatuses that form images of a fundus and cornea or the like are in a practical stage.

The apparatus disclosed in Patent Document 1 uses a technique of so-called "Fourier Domain OCT." That is to say, the apparatus irradiates a low-coherence light beam to an object, superposes the reflected light and the reference light to generate an interference light, and acquires the spectral intensity distribution of the interference light to execute Fourier transform, thereby imaging the morphology in the depth direction (the z-direction) of the object. Furthermore, the apparatus is provided with a galvano mirror that scans a light beam (signal light) along one direction (x-direction) perpendicular to the z-direction, and is thereby configured to form an image of a desired measurement target region of the object. An image formed by this apparatus is a two-dimensional cross sectional image in the depth direction (z-direction) along the scanning direction (x-direction) of the light beam. The technique of this type is also called Spectral Domain.

Patent Document 2 discloses a technique of scanning with a signal light in the horizontal direction (x-direction) and the vertical direction (y-direction) to form multiple two-dimensional cross sectional images in the horizontal direction, and acquiring and imaging three-dimensional cross sectional information of a measured range based on the cross sectional images. As the three-dimensional imaging, for example, a method of arranging and displaying multiple cross sectional images in the vertical direction (referred to as stack data or the like), or a method of executing a rendering process on volume data (voxel data) based on stack data to form a three-dimensional image may be considered.

Patent Documents 3 and 4 disclose other types of OCT apparatuses. Patent Document 3 describes an OCT apparatus that images the morphology of an object by sweeping the wavelength of light that is irradiated to an object (wavelength sweeping), detecting interference light obtained by superposing the reflected lights of the light of the respective wavelengths on the reference light to acquire its spectral intensity distribution, and executing Fourier transform. Such an OCT apparatus is called a Swept Source type or the like. The Swept Source type is a kind of the Fourier Domain type.

Further, Patent Document 4 describes an OCT device that irradiates a light having a predetermined beam diameter to an object and analyzes the components of an interference light obtained by superposing the reflected light and the reference light, thereby forming an image of the object in a cross-section orthogonal to the travelling direction of the light. Such an OCT device is called a full-field type, en-face type or the like.

Patent Document 5 discloses an example of applying OCT to the ophthalmologic field. It should be noted that, before OCT was applied, a retinal camera, a slit lamp microscope, etc. were used as apparatuses for observing an eye (see Patent Documents 6 and 7, for example). The retinal camera is an apparatus that photographs the fundus by projecting illumination light onto the eye and receiving the reflected light from the fundus. The slit lamp microscope is an apparatus that obtains an image of the cross-section of the cornea by cutting off the light section of the cornea using slit light.

The apparatus with OCT is superior relative to the retinal camera, etc in that high-definition images can be obtained, further in that cross sectional images and three-dimensional images can be obtained, etc.

Thus, the apparatus using OCT can be used for observation of various regions of the eye and is capable of obtaining high-definition images, and therefore, has been applied to the diagnosis of various ophthalmic disorders.

Further, OCT is used not only in measurement of morphology of an object but also blood flow measurement of blood that flows in a blood vessel in a living body (see Patent Documents 8 and 9, for example). The blood flow measurement that uses OCT is applied to measurement of eye fundus blood flow etc.

PRIOR ART DOCUMENTS

Patent Documents

[Patent Document 1]
Japanese Unexamined Patent Application Publication No. H11-325849
[Patent Document 2]
Japanese Unexamined Patent Application Publication No. 2002-139421
[Patent Document 3]
Japanese Unexamined Patent Application Publication No. 2007-24677
[Patent Document 4]
Japanese Unexamined Patent Application Publication No. 2006-153838
[Patent Document 5]
Japanese Unexamined Patent Application Publication No. 2008-73099
[Patent Document 6]
Japanese Unexamined Patent Application Publication No. H09-276232
[Patent Document 7]
Japanese Unexamined Patent Application Publication No. 2008-259544
[Patent Document 8]
Japanese Unexamined Patent Application Publication No. 2009-165710

[Patent Document 9]
Japanese Unexamined Patent Application Publication No. 2010-523286

SUMMARY OF THE INVENTION

Problem that the Invention is to Solve

Since there are cases in which the change of blood flow occurs in early diseases, it can be thought that blood flow measurement may be used for diagnosis thereof. However, it is difficult for conventional blood flow measurement to achieve sufficient accuracy for early diagnosis.

Thus, a purpose of the present invention is to provide a technology that is capable of carrying out blood flow measurement with high accuracy.

Further, conventional image display apparatuses etc have a problem that multiple images required to measure blood flow cannot be displayed adequately.

For example, there is no conventional technology for associating a cross sectional image, phase image and blood flow information required to measure blood flow information and for displaying them simultaneously. For this reason, conventional technology cannot obtain measurement state etc. of blood flow information adequately by utilizing images required for blood flow measurement.

Means for Solving the Problem

The present invention is an image displaying method executed by using: a cross sectional image storage configured to store a cross sectional image group including multiple cross sectional images each of which is associated with time and expresses a cross section intersecting at least one blood vessel of a living body; a phase image storage configured to store a phase image group including multiple phase images each of which is associated with time and expresses chronological variation of phase difference at a cross section intersecting at least one blood vessel of the living body; a blood flow information storage configured to store a blood flow information group including multiple blood flow information each of which is related to blood flow in a blood vessel of the living body and is associated with time; a display; and a change operation receiving part, that comprise a display step in which the display synchronously displays a cross sectional image included in the cross sectional image group and a phase image included in the phase image group using time associated with the cross sectional image and the phase image, and displays a blood flow image that expresses multiple blood flow information, from among the blood flow information included in the blood flow information group, associated with time within a period including time associated with the cross sectional image and the phase image that are being displayed; and change operation receiving step in which the change operation receiving part receives a change operation for changing display of one of the cross sectional image, the phase image and the blood flow image that are displayed by the display step, wherein in the display step, the display performs the same change as the change corresponding to the change operation to the cross sectional image, the phase image and the blood flow image that are displayed in the display step.

BRIEF DESCRIPTION OF THE DRAWINGS

FIG. 10 is a flowchart for explaining the present operation.

FIG. 13 is a diagram showing an example of living body image management information of the present embodiment.

FIG. 14 is a diagram showing an example of blood vessel management information of the present embodiment.

FIG. 16 is a diagram showing an example of cross section management information of the present embodiment.

FIG. 17 is a diagram showing an example of cross section blood vessel management information of the present embodiment.

FIG. 19 is a diagram showing an example of phase management information of the present embodiment.

FIG. 20 is a diagram showing an example of phase blood vessel management information of the present embodiment.

FIG. 21 is a diagram showing an example of blood flow information management information of the present embodiment.

FIG. 29 is a diagram showing an example of blood vessel classification management information of the present embodiment.

MODE FOR CARRYING OUT THE INVENTION

Examples of embodiments of an optical image measuring apparatus according to the present invention will be described in detail with reference to the drawings. An optical image measuring apparatus according to the present invention forms a cross sectional image and three-dimensional image of a living body by using OCT. In the present description, images obtained by OCT are sometimes referred to as OCT images. Furthermore, a measuring action for forming an OCT image is sometimes referred to as OCT measurement. It should be noted that the contents described in the documents cited in this description may be applied to the following embodiments.

In the following embodiments, an eye (fundus) is regarded as a measurement target of a living body, and a fundus observation apparatus is described in which OCT measurement of the fundus is carried out by employing Fourier Domain OCT. Particularly, the fundus observation apparatus according to the following embodiments is capable of obtaining both a fundus OCT image with Spectral Domain OCT and a fundus image, which is similar to the apparatus disclosed in Patent Document 5. It should be noted that configurations according to the present invention may be applied to a fundus observation apparatus of any type other than Spectral Domain (for example, Swept Source OCT). Further, apparatuses in which an OCT apparatus and a retinal camera are combined are explained in the embodiments; however, it is possible to combine an OCT apparatus comprising configuration according to the embodiments with a fundus imaging apparatus of any type, such as an SLO (Scanning Laser Ophthalmoscope), slit lamp microscope, ophthalmologic surgical microscope, etc. Further, configurations of the embodiment may be incorporated with a single-functional OCT apparatus. Moreover, it is possible to apply the configurations of the embodiments to OCT apparatuses that measure biological sites other than eye fundus. Such biological sites may be arbitrary sites that can be targets of examining states of blood flow.

[Configurations]

Figure 1:
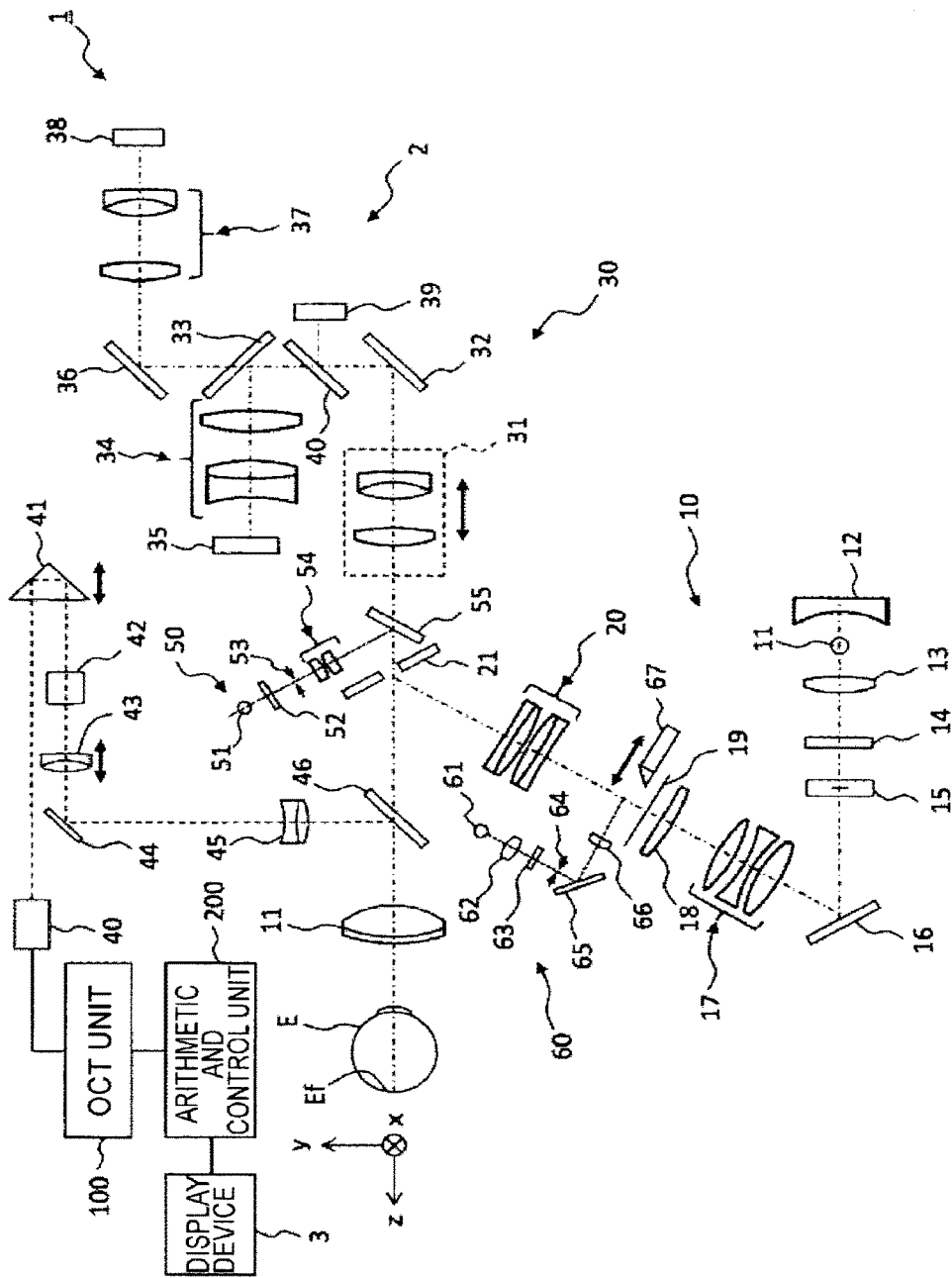
FIG. 1 is a schematic diagram showing an example of a configuration of a fundus observation apparatus (optical image measuring apparatus) according to an embodiment.

A fundus observation apparatus 1, as shown in FIG. 1, includes a retinal camera unit 2, an OCT unit 100, and an arithmetic and control unit 200. The retinal camera unit 2 has almost the same optical system as a conventional retinal camera. The OCT unit 100 is provided with an optical system for obtaining an OCT image of a fundus. The arithmetic and control unit 200 is provided with a computer that executes various arithmetic processes, control processes, and so on.

[Retinal Camera Unit]

The retinal camera unit 2 shown in FIG. 1 is provided with an optical system for forming a 2-dimensional image (fundus image) representing the surface morphology of the fundus Ef of an eye E. Fundus images include observation images, photographed images, etc. The observation image is, for example, a monochromatic moving image formed at a prescribed frame rate using near-infrared light. The photographed image may be, for example, a color image captured by flashing visible light, or a monochromatic still image captured by using near-infrared light or visible light as illumination light. The retinal camera unit 2 may also be configured to be capable of capturing other types of images such as a fluorescein angiography image, an indocyanine green fluorescent image, and an autofluorescent image.

The retinal camera unit 2 is provided with a chin rest and a forehead placement for supporting the face of the subject. Moreover, the retinal camera unit 2 is provided with the illumination optical system 10 and the imaging optical system 30. The illumination optical system 10 irradiates illumination light to the fundus Ef. The imaging optical system 30 guides a fundus reflected light of the illumination light to imaging devices (CCD image sensors 35, 38 (sometimes referred to simply as CCD)). Moreover, the imaging optical system 30 guides signal light input from the OCT unit 100 to the fundus Ef, and guides the signal light returned from the fundus Ef to the OCT unit 100.

An observation light source 11 of the illumination optical system 10 comprises, for example, a halogen lamp. Light (observation illumination light) output from the observation light source 11 is reflected by a reflection mirror 12 with a curved reflection surface, and becomes near-infrared after passing through a visible cut filter 14 via a condenser lens 13. Furthermore, the observation illumination light is once converged near an imaging light source 15, reflected by a mirror 16, and passes through relay lenses 17 and 18, a diaphragm 19, and a relay lens 20. Then, the observation illumination light is reflected on the peripheral part (the surrounding region of an aperture part) of an aperture mirror 21, transmitted through a dichroic mirror 46, and refracted by an object lens 22, thereby illuminating the fundus Ef. It should be noted that LED (Light Emitting Diode) may be used as the observation light source.

The fundus reflection light of the observation illumination light is refracted by the object lens 22, transmitted through the dichroic mirror 46, passes through the aperture part formed in the center region of the aperture mirror 21, transmitted through a dichroic mirror 55, travels through a focusing lens 31, and reflected by a mirror 32. Furthermore, the fundus reflection light is transmitted through a half-mirror 40, refracted by reflected by a dichroic mirror 33, and forms an image on the light receiving surface of the CCD image sensor 35 by a condenser lens 34. The CCD image sensor 35 detects the fundus reflection light at a preset frame rate, for example. An image (observation image) based on the fundus reflection light detected by the CCD image sensor 35 is displayed on a display device 3. It should be noted that when the imaging optical system is focused on the anterior eye part, the observation image of the anterior eye part of the eye E is displayed.

The imaging light source 15 comprises, for example, a xenon lamp. The light (imaging illumination light) output from the imaging light source 15 is irradiated to the fundus Ef via the same route as that of the observation illumination light. The fundus reflection light of the imaging illumination light is guided to the dichroic mirror 33 via the same route as that of the observation illumination light, transmitted through the dichroic mirror 33, reflected by a mirror 36, and forms an image on the light receiving surface of the CCD image sensor 38 by a condenser lens 37. An image (photographed image) based on the fundus reflection light detected by the CCD image sensor 38 is displayed on the display device 3. It should be noted that the display device 3 for displaying the observation image and the display device 3 for displaying the photographed image may be the same or different. Further, when similar photographing is carried out by illuminating the eye E with infrared light, infrared photographed image is displayed. Moreover, LED may be used as the imaging light source.

An LCD (Liquid Crystal Display) 39 displays a fixation target or a target for measuring visual acuity. The fixation target is a visual target for fixating the eye E, and is used when photographing a fundus or performing OCT measurement.

Part of the light output from the LCD 39 is reflected by the half-mirror 40, reflected by the mirror 32, passes through the aperture part of the aperture mirror 21, refracted by the object lens 22, and projected onto the fundus Ef.

By changing a display position of the fixation target on the screen of the LCD 39, it is possible to change the fixation position of the eye E. Examples of the fixation positions of the eye E include the position for acquiring an image centered at the macula of the fundus Ef, the position for acquiring an image centered at the optic papilla, the position for acquiring an image centered at the fundus center located between the macula and the optic papilla, and so on, as in conventional retinal cameras. Further, the display position of the fixation target may be arbitrarily changed.

Furthermore, as with conventional retinal cameras, the retinal camera unit 2 is provided with an alignment optical system 50 and a focus optical system 60. The alignment optical system 50 generates a target (alignment target) for matching the position (alignment) of the device optical system with respect to the eye E. The focus optical system 60 generates a target (split target) for matching the focus with respect to the eye Ef.

Light (alignment light) output from an LED 51 of the alignment optical system 50 passes through diaphragms 52 and 53 and a relay lens 54, is reflected by the dichroic mirror 55, passes through the aperture part of the aperture mirror 21, is transmitted through the dichroic mirror 46, and is projected onto the cornea of the eye E by the object lens 22.

Cornea reflection light of the alignment light passes through the object lens 22, the dichroic mirror 46 and the aperture part, a part of the cornea reflection light is transmitted through the dichroic mirror 55, passes through the focusing lens 31, reflected by the mirror 32, transmitted through the half-mirror 40, reflected by the dichroic mirror 33, and projected onto the light receiving surface of the CCD image sensor 35 by the condenser lens 34. An image (alignment target) captured by the CCD image sensor 35 is displayed on the display device 3 together with the observation image. The user conducts alignment by an operation that is the same as conventional retinal cameras. Further, alignment may be performed in a way in which the arithmetic and control unit 200 analyzes the position of the alignment target and controls the movement of the optical system (automatic alignment function).

In order to conduct focus adjustment, the reflection surface of a reflection rod 67 is positioned at a slanted position on the optical path of the illumination optical system 10. Light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is formed once on the reflection surface of the reflection rod 67 by a condenser lens 66. Furthermore, the focus light passes through the relay lens 20, is reflected at the aperture mirror 21, is transmitted through the dichroic mirror 46, is refracted by the object lens 22, and is projected onto the fundus Ef.

The fundus reflection light of the focus light passes through the same route as the cornea reflection light of the alignment light and is detected by the CCD image sensor 35. An image (split target) captured by the CCD image sensor 35 is displayed on the display device 3 together with the observation image. The arithmetic and control unit 200, as in the conventional technology, analyzes the position of the split target, and moves the focusing lens 31 and the focus optical system 60 for focusing (automatic focusing function). Further, focusing may be performed manually while visually recognizing the split target.

The dichroic mirror 46 splits the optical path for OCT from the optical for eye fundus photographing. More specifically, the optical path for fundus photography and the optical path for OCT measurement are configured to be coaxial and share the optical path on the eye E side of the dichroic mirror 46. The dichroic mirror 46 reflects light of the wavelength band used for OCT, and transmits the light for eye fundus photographing. The optical path for OCT is provided with a collimator lens unit 40, an optical path length changing part 41, a galvano scanner 42, a focusing lens 43, a mirror 44 and a relay lens 45.

The optical path length changing part 41 is capable of moving in the direction indicated by the arrow in FIG. 1 to change the length of the optical path for OCT. This change of optical path length may be used for correction of the optical path length in accordance with the axial length of the eye E, and for adjustment of the condition of interference. The optical path length changing part 41 is configured to comprise a corner cube and a mechanism for moving the corner cube, for example.

The galvano scanner 42 changes the travelling direction of light (signal light LS) travelling along the optical path for OCT. Thereby, the fundus Ef is scanned by the signal light LS. The galvano scanner 42 is configured to comprise a galvano mirror for scanning with the signal light LS in the x-direction, a galvano mirror for scanning in the y-direction, and a mechanism for independently driving these. Thereby, the signal light LS may be scanned in an arbitrary direction in the xy-plane. The galvano scanner 42 is an example of "scanner".

[OCT Unit]

Figure 2:
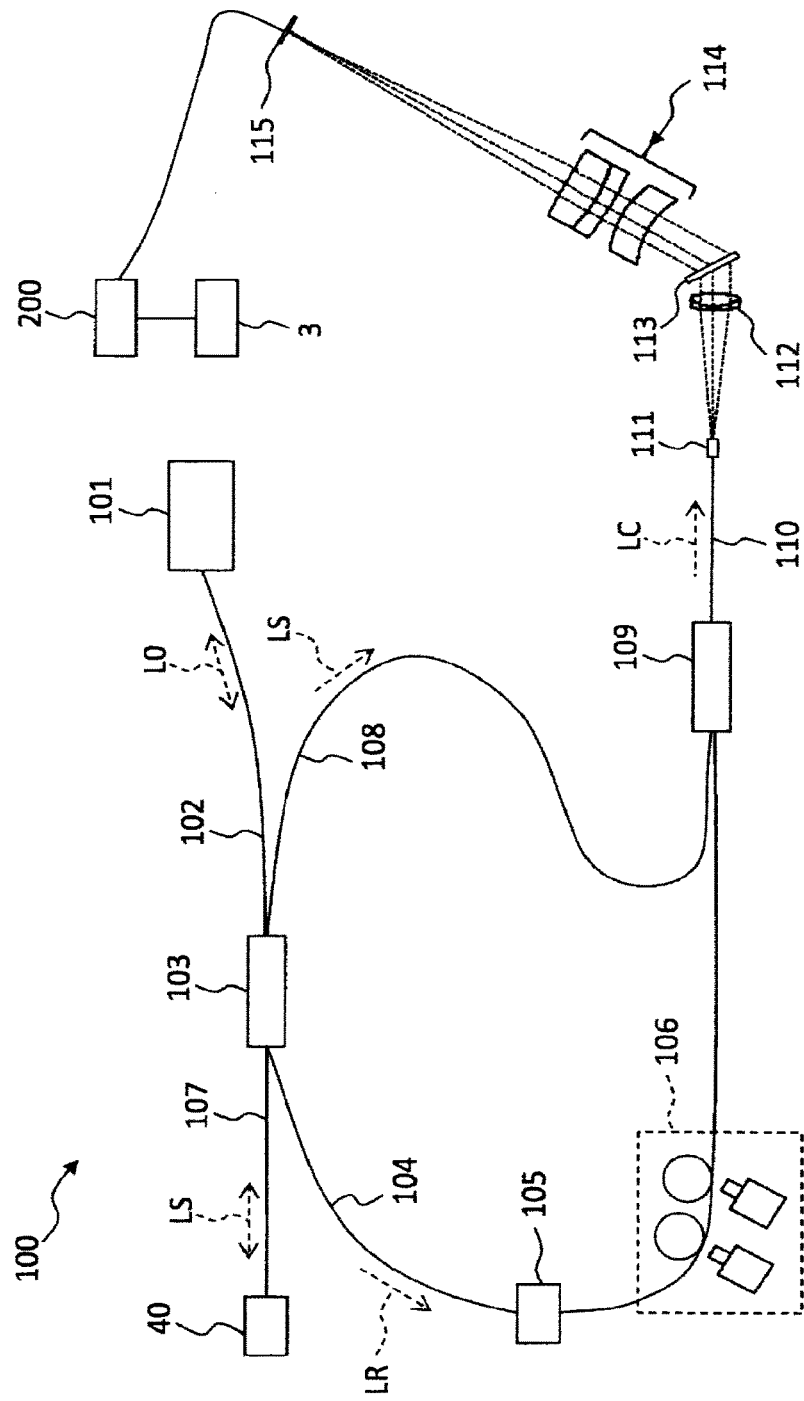
FIG. 2 is a schematic diagram showing an example of a configuration of a fundus observation apparatus according to an embodiment.

An example of the configuration of the OCT unit 100 is explained while referring to FIG. 2. The OCT unit 100 is provided with an optical system for obtaining an OCT image of the fundus Ef. The optical system comprises a similar configuration to a conventional Spectral Domain OCT apparatus. That is to say, this optical system is configured to split low-coherence light into signal light and reference light, superpose the signal light returned form the fundus Ef and the reference light having traveled through a reference optical path to generate interference light, and detect the spectral components of the interference light. This detection result (detection signal) is transmitted to the arithmetic and control unit 200.

It should be noted that when Swept Source OCT apparatus is used, a swept source is provided instead of a low-coherence light source while an optical member for spectrally decomposing interference light is not provided. In general, any known technology in accordance with the type of OCT may be arbitrarily applied to the configuration of the OCT unit 100.

A light source unit 101 outputs broadband low-coherence light L0. The low-coherence light L0, for example, includes near-infrared wavelength band (about 800-900 nm) and has a coherence length of about tens of micrometer. Moreover, it is possible to use, as the low-coherence light L0, near-infrared light having wavelength band that is impossible to be detected by human eyes, for example, infrared light having the center wavelength of about 1040-1060 nm.

The light source unit 101 is configured to comprise light output device, such as an SLD (super luminescent diode), LED, SOA (Semiconductor Optical Amplifier) and the like.

The low-coherence light L0 output from the light source unit 101 is guided to a fiber coupler 103 by an optical fiber 102 and split into the signal light LS and the reference light LR.

The reference light LR is guided to an optical attenuator 105 by an optical fiber 104. Through any known technology, the optical attenuator 105 received control of the arithmetic and control unit 200 for automatically adjusting light amount (light intensity) of the reference light LR guided to the optical fiber 104. The reference light LR having adjusted by the optical attenuator 105 is guided to a polarization controller 106 by the optical fiber 104. The polarization controller 106 is a device configured to, for example, apply stress to the loop-form optical fiber 104 from outside to adjust polarization condition of the reference light LR being guided in the optical fiber 104. It should be noted that the configuration of the polarization controller 106 is not limited to this, and arbitrary known technology may be applied. The reference light LR having adjusted by the polarization controller 106 is guided to a fiber coupler 109.

The signal light LS generated by the fiber coupler 103 is guided by the optical fiber 107, and converted into a parallel light flux by the collimator lens unit 40. Further, the signal light LS travels through the optical path length changing part 41, the galvano scanner 42, the focusing lens 43, the mirror 44 and the relay lens 45, and reaches the dichroic mirror 46. Further, the signal light LS is reflected by the dichroic mirror 46, refracted by the objective lens 22, and projected to the fundus Ef. The signal light LS is scattered (including reflection) at various depth positions of the fundus Ef. The back-scattered light of the signal light LS from the fundus Ef travels along the same route as the outward way in the opposite direction to the fiber coupler 103, and is reached the fiber coupler 109 through an optical fiber 108.

The fiber coupler 109 superposes the back-scattered light of the signal light LS and the reference light LR having passed through the optical fiber 104. Interference light LC thus generated is guided by an optical fiber 110 and output from an exit end 111. Furthermore, the interference light LC is converted into a parallel light flux by a collimator lens 112, spectrally divided (spectrally decomposed) by a diffraction grating 113, converged by a condenser lens 114, and projected onto the light receiving surface of a CCD image sensor 115. It should be noted that although the diffraction grating 113 shown in FIG. 2 is of transmission type, any other kind of a spectrally decomposing element (such as reflection type) may be used.

The CCD image sensor 115 is for example a line sensor, and detects the respective spectral components of the spectrally decomposed interference light LC and converts the components into electric charges. The CCD image sensor 115 accumulates these electric charges, generates a detection signal, and transmits the detection signal to the arithmetic and control unit 200.

Although a Michelson-type interferometer is employed in the present embodiment, it is possible to employ any type of interferometer such as a Mach-Zehnder-type as necessary. Instead of a CCD image sensor, other types of image sensors, such as a CMOS (Complementary Metal Oxide Semiconductor) image sensor, may be used.

[Arithmetic and Control Unit]

A configuration of the arithmetic and control unit 200 will be described. The arithmetic and control unit 200 analyzes the detection signals input from the CCD image sensor 115 to form an OCT image of the fundus Ef. Arithmetic processing for this may be the same as that of a conventional Spectral Domain OCT apparatus.

Further, the arithmetic and control unit 200 controls each part of the retinal camera unit 2, the display device 3 and the OCT unit 100. For example, the arithmetic and control unit 200 displays an OCT image of the fundus Ef on the display device 3.

Further, as controls of the retinal camera unit 2, the arithmetic and control unit 200 executes: controls of actions of the observation light source 101, the imaging light source 103 and LED's 51 and 61; control of action of the LCD 39; controls of movements of the focusing lenses 31 and 43; control of movement of the reflection rod 67; control of movement of the focus optical system 60; control of movement of the optical path length changing part 41; control of action of the galvano scanner 42; and so on.

Further, as controls of the OCT unit 100, the arithmetic and control unit 200 executes: control of action of the light source unit 101; control of action of the optical attenuator 105; control of action of the polarization controller 106; control of action of the CCD image sensor 115; and so on.

The arithmetic and control unit 200 comprises a microprocessor, a RANI, a ROM, a hard disk drive, a communication interface, and so on, as in conventional computers. The storage device such as the hard disk drive stores a computer program for controlling the fundus observation apparatus 1. The arithmetic and control unit 200 may be provided with various circuit boards such as a circuit board for forming OCT images. Moreover, the arithmetic and control unit 200 may be provided with operation devices (input devices) such as a keyboard, a mouse, etc. and/or a display device such as an LCD etc.

The retinal camera unit 2, the display device 3, the OCT unit 100, and the arithmetic and control unit 200 may be integrally configured (that is, provided within a single case), or separately configured in two or more cases.

[Control System]

Figure 3:
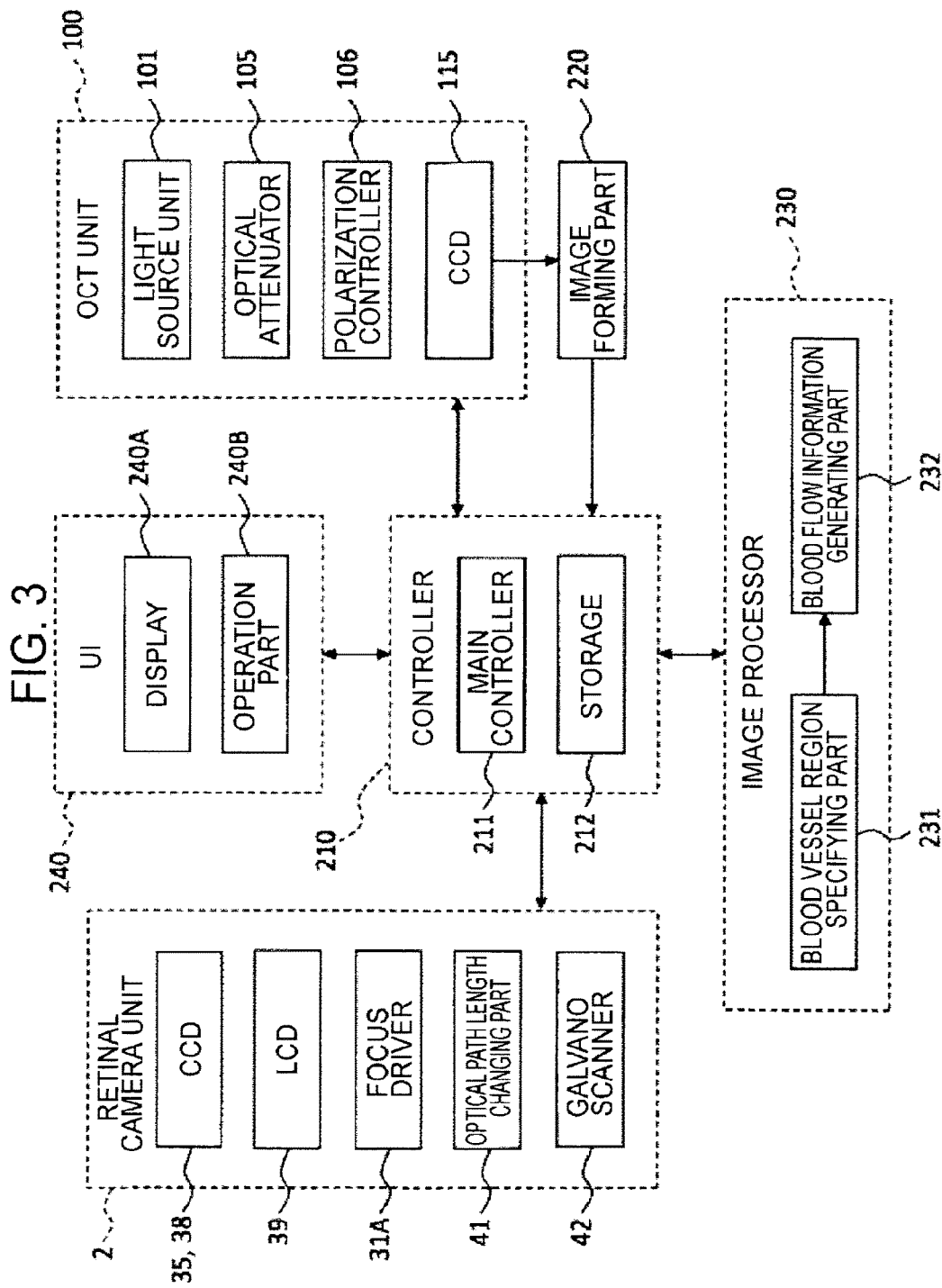
FIG. 3 is a schematic block diagram showing an example of the present configuration.
Figure 4:
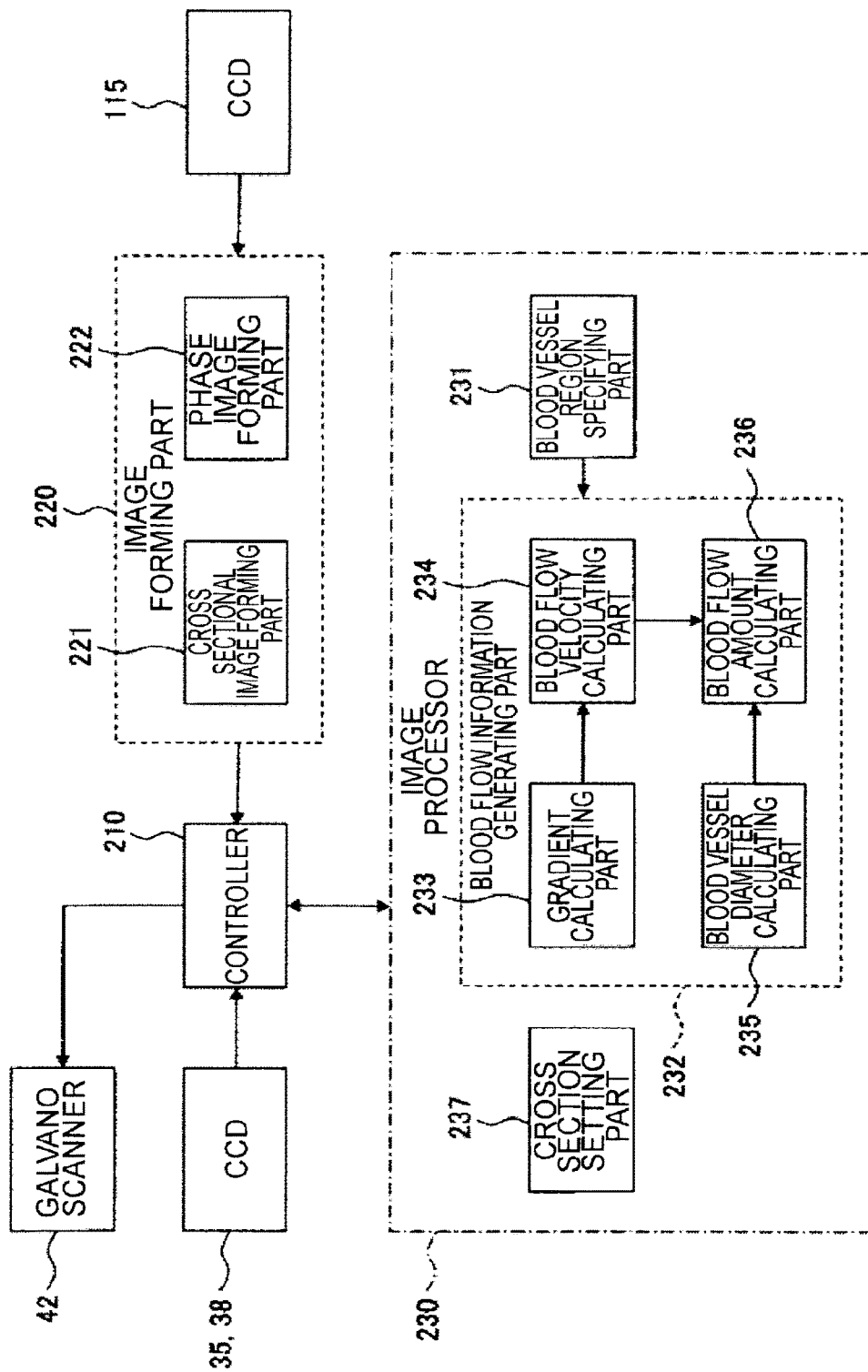
FIG. 4 is a schematic block diagram showing an example of the present configuration.

A configuration of a control system of the fundus observation apparatus 1 will be described with reference to FIGS. 3 and 4.

(Controller)

The control system of the fundus observation apparatus 1 has a configuration centered on a controller 210 The controller 210 is configured to comprise, for example, the aforementioned microprocessor, RAM, ROM, hard disk drive, and communication interface, etc. The controller 210 is provided with a main controller 211 and storage 212.

(Main Controller)

The main controller 211 performs the aforementioned various kinds of controls. Specifically, the main controller 211 controls a focus driver 31A, the optical path length changing part 41 and the galvano scanner 42 of the retinal camera unit 2, and further controls the light source unit 101, the optical attenuator 105 and the polarization controller 106 of the OCT unit 100.

The focus driver 31A moves the focusing lens 31 in the direction of the optical axis. Thereby, the focus position of the imaging optical system 30 is changed. It should be noted that the main controller 211 may control an optical system driver (not shown in diagrams) to three dimensionally move the optical system provided in the retinal camera unit 2. This control is used for alignment and tracking. Tracking is an operation for move the optical system in accordance with eye movement of the eye E. When tracking is applied, alignment and focusing are carried out in advance. Tracking is a function to maintain adequate positional relationship in which alignment and focusing are matched by causing the position of the optical system to follow the eye movement.

The main controller 211 executes a process of writing data into the storage 212, and a process of reading out data from the storage 212.

(Storage)

The storage 212 stores various kinds of data. The data stored in the storage 212 may include image data of OCT images, image data of fundus images, and eye information, for example. The eye information includes information on the eye, such as information on a subject such as a patient ID and a name, identification information on left eye or right eye, and so on. Further, the storage 212 stores various programs and data for operating the fundus observation apparatus 1.

(Image Forming Part)

An image forming part 220 forms image data of a cross sectional image of the fundus Ef and image data of a phase image based on the detection signals from the CCD image sensor 115. These images will be described later. The image forming part 220 includes the aforementioned circuit board and/or microprocessor, for example. It should be noted "image data" and the "image" based on the image data may be identified with each other in this description. The image forming part 220 includes a cross sectional image forming part 221 and a phase image forming part 222.

In the present embodiment, two types of scanning (a first scan and second scan) are performed to the fundus Ef. In the first scan, a first cross section intersecting a blood vessel of interest (interested blood vessel) of the fundus Ef is repeatedly scanned by the signal light LS. In the second scan, a second cross section that intersects this interested blood vessel and is located in the vicinity of the first cross section is scanned by the signal light LS. Here, it is desired that the first and second cross sections are oriented so as to be perpendicular to the running direction the interested blood vessel. As shown in a fundus image D of FIG. 5, in this embodiment, one first cross section C0 and two second cross sections C1 and C2 are set in the vicinity of the optic papilla Da of the fundus Ef so as to intersect a predetermined interested blood vessel Db. One of the two second cross sections C1 and C2 is located in the upstream of the interested blood vessel Db than the first blood vessel C0, and the other is located in the downstream.

It should be noted that the first scan is preferably carried out during a period of at least one cardiac cycle of the heart of the patient. Therefore, blood flow information can be obtained for all time phases of the heart. It should be noted that period of time in which the first scan is performed may be a preset constant period, or may be set for every patient or every examination. In the former case, the period of time longer than a typical cardiac cycle may be set (for example, 2 seconds). In the latter case, examination data such as an electro-cardiogram of the patient may be referred to. Here, a factor other than cardiac cycle may be considered. Examples of such factors include examination time (burden to patients), response time of the galvano scanner 42 (scanning intervals), response time of CCD 115 (scanning intervals), and so on.

(Cross Sectional Image Forming Part)

The cross sectional image forming part 221 forms cross sectional images (first cross sectional image) expressing chronological variation of morphology of the first cross section based on detection results of the interference light LC acquired by the first scan. This processing will be described in more detail. The first scan is carried out by repeatedly scanning the first cross section C0 as described above. Detection signals are successively input from the CCD 115 of the OCT unit 100 into the cross sectional image forming part 221 during the first scan. The cross sectional image forming part 221 forms a single cross sectional image of the first cross section C0 based on detection signals corresponding to the respective scans in the first scan. The cross sectional image forming part 221 repeats such processing preset repetition times of the first scan, thereby forming a series of cross sectional images along time series. Here, it may be configured to improve image quality by dividing these cross sectional images into multiple groups and superposing cross sectional images in the respective groups.

Further, the cross sectional image forming part 221 forms a cross sectional image (second cross sectional image) expressing morphology of the second cross section C1 and a cross sectional image (second cross sectional image) expressing morphology of the second cross section C2 based on detection results of the interference light LC acquired by the second scan of the second cross sections C1 and C2. This processing is carried out in the same way as the case of the first cross sectional image. It should be noted that the first cross sectional image is a series of cross sectional images in chronological order; however, the second cross sectional image may be a single cross sectional image. Alternatively, it may be configured to improve image quality of the second cross sectional images of the second cross sections C1 and C2 by superposing multiple cross sectional images obtained from multiple scanning of the second cross section C1 or C2.

Such processing of forming cross sectional images includes processes such as noise elimination (noise reduction), filtering and FFT (Fast Fourier Transform). In the case in which other type of OCT is applied, the cross sectional image forming part 221 executes known process in accordance with the applied OCT type.

(Phase Image Forming Part)

The phase image forming part 222 forms a phase image expressing chronological variation of phase difference in the first cross section based on the detection results of the interference light LC acquired by the first scan. The detection results used in this processing is the same as those used in the processing of forming the first cross sectional image executed by the cross sectional image forming part 221. Therefore, position matching between the first cross sectional image and the phase image is possible. More specifically, it is possible to obtain natural correspondence between pixels of the first cross sectional image and pixels of the phase image.

An example of method of forming a phase image is described. A phase image of the present example is obtained by calculating phase difference between adjacent A-line complex signals (that is, signals corresponding to adjacent scanning points). In other words, a phase image of the present example is formed, for each pixel of the first cross sectional image, based on chronological variation of pixel value (brightness value) of the concerned pixel. For an arbitrary pixel, the phase image forming part 222 considers a graph showing chronological variation of brightness value thereof. The phase image forming part 222 calculates phase difference $\Delta\phi$ between two points of time t1 and t2 ($=$t1$+\Delta$t) that are apart from each other by a preset time interval $\Delta$t in this graph. Then, this phase difference $\Delta\phi$ is defined as phase difference $\Delta\phi$(t1) at the point of time t1 (more generally, at an arbitrary point of time between the two points of time t1 and t2). Such processing is carried out for each of many points of time that are preset, thereby obtaining the chronological variation of phase difference at the concerned pixel.

A phase image expresses value of respective pixels at respective points of time as an image. This imaging processing may be realized by representing values of phase difference by display colors and/or brightness. Here, it may be configured to differentiate display color in the case in which phase increases along time series from display color in the case in which phase decreases (for example, the former display color is red and the latter is blue). Further, the magnitude of phase variation may be represented by color strength (color depth). Introduction of such representation methods makes it possible to clearly indicate direction and/or speed of blood flow by display colors. A phase image is formed by carrying out the above processing for respective pixels.

It should be noted that chronological variation of phase difference is obtained by assuring phase correlation by making the above time interval Δt sufficiently small. Here, oversampling is executed under a condition in which the time interval Δt is set to be a value smaller than the time corresponding to the resolution of a cross sectional image in the scanning of the signal light LS.

(Image Processor)

An image processor 230 executes various image processing and analysis processing on images formed by the image forming part 220. For example, the image processor 230 executes various correction processing such as brightness correction, dispersion correction of images, etc. Further, the image processor 230 executes various image processing and analysis processing on images obtained by the retinal camera unit 2 (fundus images, anterior eye part images, etc.).

The image processor 230 executes known image processing such as interpolation processing for interpolating pixels between cross sectional images to form image data of a three-dimensional image of the fundus Ef. It should be noted that the image data of a three-dimensional image refers to image data that the positions of pixels are defined by the three-dimensional coordinates. The image data of a three-dimensional image is, for example, image data composed of three-dimensionally arranged voxels. This image data is referred to as volume data, voxel data, or the like. For displaying an image based on the volume data, the image processor 230 executes a rendering process on this volume data, and forms image data of a pseudo three-dimensional image taken from a specific view direction. On a display device such as a display 240A, this pseudo three-dimensional image is displayed.

Further, it is also possible to form stack data of multiple cross sectional images as the image data of a three-dimensional image. Stack data is image data obtained by three-dimensionally arranging multiple cross sectional images obtained along multiple scanning lines, based on the positional relation of the scanning lines. That is to say, stack data is image data obtained by expressing multiple cross sectional images defined by originally individual two-dimensional coordinate systems by a three-dimensional coordinate system (in other words, embedding into a three-dimensional space).

The image processor 230 includes a blood vessel region specifying part 231 and a blood flow information generating part 232. The blood flow information generating part 232 is provided with a gradient calculating part 233, a blood flow velocity calculating part 234, a blood vessel diameter calculating part 235 and a blood flow amount calculating part 236. Further, the image processor 230 includes a cross section setting part 237. These parts 231 to 237 will be described below.

(Blood Vessel Region Specifying Part)

The blood vessel region specifying part 231 specifies a blood vessel region corresponding to the interested blood vessel Db for each of the first cross sectional image, the second cross sectional image and the phase image. This processing may be carried out by analyzing pixel values of the respective images (for example, threshold processing).

There are cases in which a phase image does not have enough resolution for specifying a boundary of a blood vessel region although first and second cross sectional images have enough resolution for executing analysis processing. However, it is necessary to specify a blood vessel region of a phase image with high precision and high accuracy because blood flow information is generated based on the phase image. Accordingly, it is desirable to specify a blood vessel region of a phase image more accurately by performing the following processing, for example.

As described above, a first cross sectional image and phase image are formed from the same detection signals, correspondence between these images can be obtained. Utilizing this fact, firstly, a first cross sectional image is analyzed to find a blood vessel region, and then an image region in a phase image consisting of pixels corresponding to the pixels included in this blood vessel region is defined as a blood vessel region in the phase image. This processing allows highly precise and highly accurate specification of blood vessel regions in the phase image.

(Blood Flow Information Generating Part)

The blood flow information generating part 232 generates blood flow information related to the interested blood vessel Db based on distance between the first cross section and the second cross section, result of specification of blood vessel regions and chronological variation of phase difference within a blood vessel region of a phase image. Here, the distance between the first cross section and the second cross section (distance between cross sections) is determined in advance. An example of this will be described later in the explanation of the cross section setting part 237. A blood vessel region is obtained by the blood vessel region specifying part 231. The chronological variation of phase difference within a blood vessel region of a phase image is obtained as chronological variation of phase difference at pixels within a blood vessel region of a phase image. The following is description of an example of configuration for performing this processing. As described above, the blood flow information generating part 232 is provided with a gradient calculating part 233, a blood flow velocity calculating part 234, a blood vessel diameter calculating part 235 and a blood flow amount calculating part 236.

(Gradient Calculating Part)

The gradient calculating part 233 calculates gradient of the interested blood vessel Db in the first cross section based on the distance between cross sections and the specification result of blood vessel regions. To begin with, the reason why the gradient of the interested blood vessel Db is calculated is explained. Blood flow information is obtained by means of Doppler OCT (see Patent Documents 8 and 9). A component of velocity of blood flow that contributes to Doppler shift is a component in the irradiation direction of the signal light LS. Therefore, even if blood flow velocity is the same, Doppler shift given to the signal light LS varies in accordance with the angle between blood flow direction (that is, direction of the interested blood vessel Db) and the signal light LS, thereby changing blood flow information obtained. In order to avoid such inconvenience, it is necessary to find the gradient of the interested blood vessel Db and reflect it in calculation processing.

Figure 6:
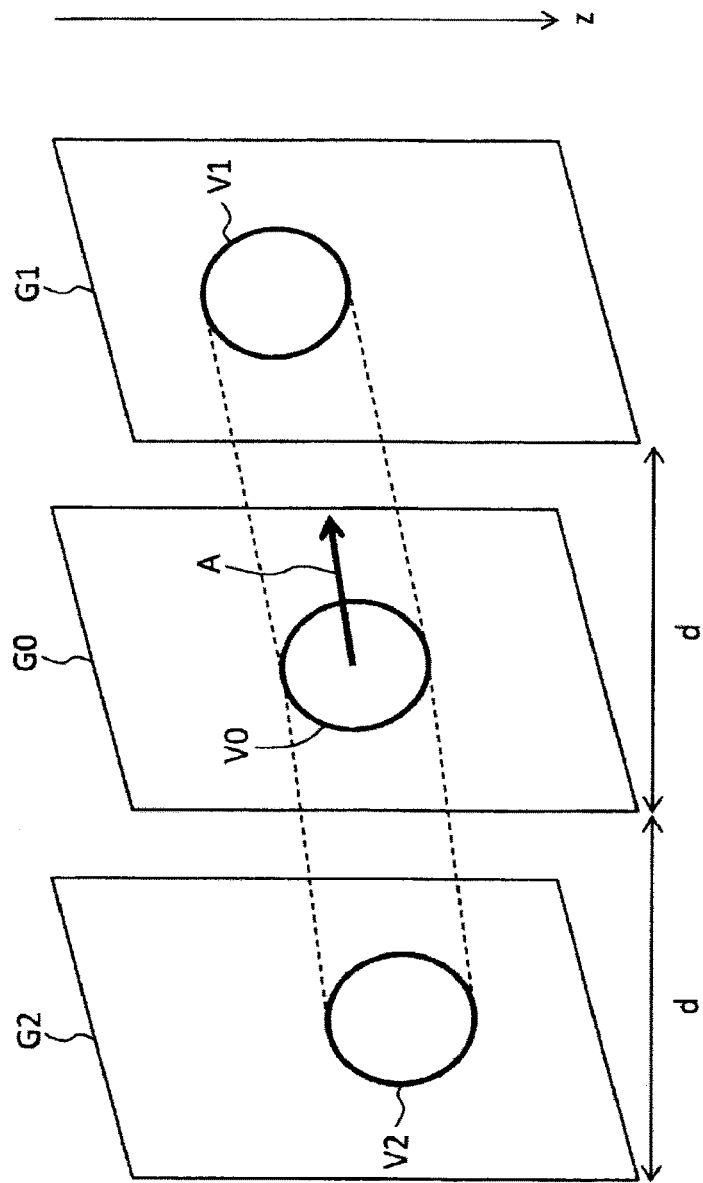
FIG. 6 is a schematic diagram showing an example of the present operation.

Methods of calculating the gradient of the interested blood vessel Db will be described by referring to FIG. 6. Symbols G0, G1 and G2 indicate a first cross sectional image at the first cross section C0, a second cross sectional image at the second cross section C1 and a second cross sectional image at the second cross section C2, respectively. Further, Symbols V0, V1 and V2 indicate a blood vessel region in the first cross sectional image G0, a blood vessel region in the second cross sectional image G1 and a blood vessel region in the second cross sectional image G2, respectively. In FIG. 6, z-coordinate axis is oriented downward on the paper surface and substantially coincides with the irradiation direction of the signal light LS. Further, the interval between adjacent cross sectional images is denoted by "d".

The gradient calculating part 233 calculate the gradient A of the interested blood vessel Db at the first cross section C0 based on the positional relationship among three blood vessel regions V0, V1 and V2. This positional relationship may be obtained, for example, by connecting the three blood vessel regions V0, V1 and V2. More specifically, the gradient calculating part 233 identifies characteristic position in the respective three blood vessel regions V0, V1 and V2, and connects these characteristic positions. Examples of this characteristic position include central position, center of gravity position, uppermost part (position at which z-coordinate value is minimum), lowermost part (position at which z-coordinate value is maximum), etc. Further, examples of methods of connecting these characteristic positions include connection by a line segment, connection by an approximation curve (spline curve, Bezier curve, etc.), and so on.

Further, the gradient calculating part 233 calculate the gradient A based on a (straight or curved) line connecting these characteristic positions. When connected by a line segment, the gradient A is calculated, for example, based on: a first line segment that connects the characteristic position in the first cross section C0 and the characteristic position in the second cross section C1; and a second line segment that connects the characteristic position in the second cross section C1 and the characteristic position in the second cross section C2. As an example of this calculation, the mean value of the gradients of the two line segments may be derived. Moreover, as an example of the case in which connection by an approximation curve, the gradient (slope) of the approximation curve at the crossing position of the approximation curve and the first cross section C0 may be derived. It should be noted that the distance between cross sections d is used for embedding the cross sectional images G0 to G2 into the xyz-coordinate system in the processing of finding a line segment or an approximation curve.

Blood vessel regions in three cross sections are considered in the present example; however, it is possible to employ a configuration in which a gradient is calculated by considering two cross sections. As a specific example of this, the gradient of the first or second line segment described above may be used as the gradient to be obtained. Moreover, a single value of gradient is obtained in the present example; however, it is possible to calculate gradient for each of two or more points (or regions) within the blood vessel region V0. In this case, the obtained two or more values of gradient may be used separately, or these values of gradient may be used to calculate the gradient A by statistically deriving a single value (such as mean value).

(Blood Flow Velocity Calculating Part)

The blood flow velocity calculating part 234 calculates blood flow velocity of the blood that flows within the interested blood vessel Db at the first cross section C0 based on chronological variation of phase difference that is obtained as a phase image. This calculated value may be blood flow velocity at a certain point of time, or may be chronological variation of blood flow velocity (blood flow velocity variation information). In the former case, it is possible to selectively acquire blood flow velocity at a preset time phase of electro-cardiogram (such as time phase of R wave), for example. Further, in the latter case, time range is the whole or arbitrary part of scanning period of the first cross section C0.

When the blood flow velocity variation information is obtained, the blood flow velocity calculating part 234 calculates a statistic of blood flow velocity in the concerned time range. Examples of this statistic include mean value, standard deviation, variance, median, maximum, minimum, local maximum, local minimum, etc. Further, histograms may be created for values of blood flow velocity.

The blood flow velocity calculating part 234 calculates blood flow velocity by means of Doppler OCT as described above. In this processing, the gradient A of the interested blood vessel Db at the first cross section C0 calculated by the gradient calculating part 233 is considered. Specifically, the gradient calculating part 233 utilizes the following relation.

$$\Delta f = \frac{2nv\cos\theta}{\lambda} \qquad [\text{Formula 1}]$$

Here:

$\Delta f$ indicates Doppler shift given to scattered light of the signal light LS;

n indicates refractive index of medium;

v indicates flow velocity of medium (blood flow velocity);

$\theta$ indicates angle between irradiation direction of the signal light LS and flow vector of medium; and $\lambda$ indicates center wavelength of the signal light LS.

In the present embodiment, n and $\lambda$ are known, $\Delta f$ is obtained from chronological variation of phase difference, and $\theta$ is obtained from the gradient A (alternatively, $\theta$ is obtained as the gradient A). The blood flow velocity v is calculated by substituting these values into the above formula.

(Blood Vessel Diameter Calculating Part)

The blood vessel diameter calculating part 235 calculates the diameter of the interested blood vessel Db at the first cross section C0. Examples of this calculation include a first method of calculation utilizing a fundus image and a second method of calculation utilizing a cross sectional image.

In the case in which the first method of calculation is applied, imaging of a site of the fundus Ef including the location of the first cross section C0 is carried out in advance. A fundus image thus obtained may be an observation image (frame thereof), or may be a photographed image. When the photographed image is a color image, an image composing the photographed image (for example, a red-free image) may be used.

The blood vessel diameter calculating part 235 sets a scale in the fundus image based on a factor(s) that determines the relationship between the scale on the fundus image and the scale in the real space such as photographing angle of view (photographing magnification), working distance, information about eyeball optical system. This scale represents length in the real space. As a specific example, this scale associates interval between adjacent pixels with the scale in the real space (for example, interval of pixels=10 μm). It should be noted that it is possible to previously calculate the relationship between various values of the above factor(s) and the scale in the real space, and store information that represents this relationship in the form of table or graph. In this case, a scale corresponding to the above factor(s) is selectively applied by the blood vessel diameter calculating part 235.

Further, the blood vessel diameter calculating part 235 calculates the diameter of the interested blood vessel Db at the first cross section C0, that is, the diameter of the blood vessel region V0 based on this scale and the pixels included in the blood vessel region V0 As a specific example, the blood vessel diameter calculating part 235 calculates the maximum or mean value of diameters of the blood vessel region V0 in various directions. Further, the blood vessel diameter calculating part 235 may approximate the contour of the blood vessel region V0 by a circle or an ellipse, and find the diameter of the circle or the ellipse. It should be noted that because determination of blood vessel diameter allows (substantial) determination of area of the blood vessel region V0 (that is, allows creation of (substantial) one-to-one correspondence between diameter and area), the area may be calculated instead of blood vessel diameter.

The second method of calculation is described. In the second method of calculation, a cross sectional image of the fundus Ef at the first cross section C0 is utilized. This cross sectional image may be the first cross sectional image or may be one obtained separately from the first cross sectional image.

Figure 5:
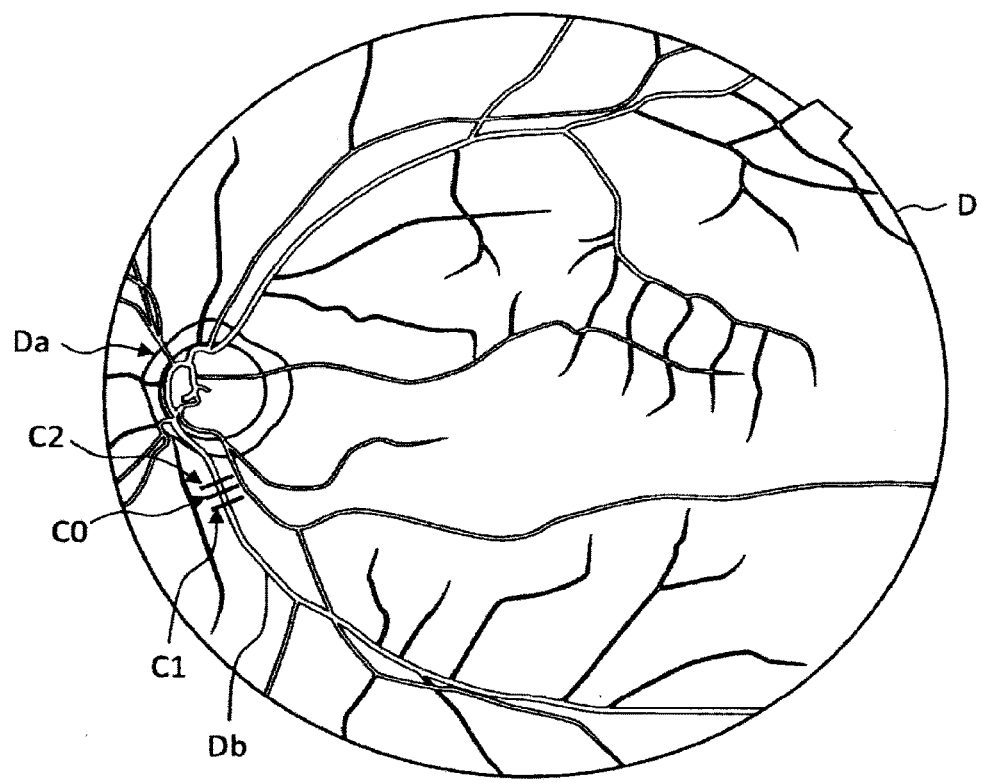
FIG. 5 is a schematic diagram showing an example of the present operation.

A scale in this cross sectional image is determined in accordance with scanning mode of the signal light LS. In the present embodiment, the first cross section C0 is scanned as illustrated in FIG. 5. The length of this first cross section is determined based on various factors that determine the relationship between the scale on an image and the scale in the real space such as working distance, information about eyeball optical system. The blood vessel diameter calculating part 235, for example, finds the interval between adjacent pixels based on this length, and calculates the diameter of the interested blood vessel Db at the first cross section C0 in the similar fashion to the first method of calculation.

(Blood Flow Amount Calculating Part)

The blood flow amount calculating part 236 calculates flow amount (flow rate) of blood that flows within the interested blood vessel based on calculation result of blood flow velocity and calculation result of blood vessel diameter. The following is an example of this processing.

It is assumed that blood flow in blood vessel is Hagen-Poiseuille flow). Further, for blood vessel diameter w and maximum of blood flow velocity Vm, blood flow amount Q is expressed as in the following formula.

$$Q = \frac{\pi w^2}{8} Vm \quad \text{[Formula 2]}$$

The objective blood flow amount Q is calculated by substituting the result w of blood vessel diameter calculated by the blood vessel diameter calculating part 235 and the maximum Vm based on the blood flow velocity calculated by the blood flow velocity calculating part 234 into this formula.

(Cross Section Setting Part)

The main controller 211 displays a fundus image on the display 240A. The fundus image may be an observation image or a photographed image. Alternatively, the fundus image may be an image included in a photographed image. The user operates the operation part 240B to designate the first cross section C0 on the fundus image displayed. The cross section setting part 237 sets the second cross sections C1 and C2 based on the designated first cross section C0 and the fundus image. It should be noted that the first cross section C0 is designated so as to cross a desired interested blood vessel Db, as described above.

An operation for designating the first cross section C0 on the fundus image is carried out by means of a pointing device, for example. Further, when the display 240A is a touch panel, the user designates the first cross section C0 by touching a desired location in the fundus image displayed. In this case, a parameter(s) (orientation, length, etc.) of the first cross section C0 is set manually or automatically.

As an example of manual setting, the user may use an interface for setting the parameter. This interface may be hardware such as a switch, or may be software such as a graphical user interface (GUI).

As an example of automatic setting, the cross section setting part 237 sets the parameter based on the location designated on the fundus image by the user. In automatic setting of length, a preset value may be applied, or the designated location and location of blood vessel in the vicinity of the designated location may be taken into account. The former value is designated based on a typical distance between the desired interested blood vessel and a blood vessel in the vicinity thereof, for example. Information on this distance may be generated based on clinical data. The latter case may be similarly carried out. In any case, the length of the first cross section C0 may be set so as to cross the interested blood vessel Db and cross no other blood vessels (in particular, thick blood vessels).

In automatic setting of orientation of the first cross section C0, a preset orientation may be applied or the orientation of the interested blood vessel Db may be taken into account. In the farmer case, information expressing gradient of an interested blood vessel at respective locations thereof may be generated and this information is referred to. This information may be generated based on clinical data. In the latter case, the running direction of the interested blood vessel Db at the designated location is found and the orientation of the first cross section C0 is set based on this running direction. The processing of finding the running direction is carried out by applying thinning processing to the interested blood vessel Db, for example. It should be noted that in any case, the orientation of the first cross section C0 is preferably set so as to orthogonally cross the running direction.

Next, processing of setting the second cross sections C1 and C2 is described. The cross section setting part 237 sets the second cross sections C1 and C2 at the locations preset distance away from the first cross section C0. This distance is set to 100 μm, for example. Specification of this distance is carried out in the aforementioned way, for example. Further, lengths and/or orientations of the second cross sections C1 and C2 may be set in the same way as in the case of the first cross section C0.

It should be noted that in the present embodiment, cross sections C0, C1 and C2 (that is, scanning positions of the signal light LS) are set based on a fundus image. To do so, it is necessary to obtain correspondence between the fundus image and scanning positions. In order to obtain this correspondence, it is preferable that, as in the present embodiment, the optical system for fundus photography and optical system for OCT measurement share part of optical path of each other. By applying such a coaxial configuration, positions in the fundus image and scanning positions may be associated with each other by considering this optical axis as a reference. Here, in this correspondence, display magnification of the fundus image (including at least one of so-called optical zooming and digital zooming) may be taken into account.

In the case in which such coaxial configuration is not applied, a fundus image and scanning positions are associated with each other based on the fundus image and a projection image obtained by OCT measurement. It should be noted that the projection image is an image that expresses morphology of fundus surface and is obtained by adding up, in the depth direction (z-direction), a three-dimensional image that is acquired by three-dimensional scan described later. By using such a projection image, positions in the fundus image and positions in the projection image may be associated with each other by means of image correlation, for example, and this association may give association between the fundus image and the scanning positions. It should be noted that when taking influences of eye movement of the eye E (involuntary eye movement during fixation etc.) into account, it can be said that the coaxial configuration is more preferable since both imaging modalities may be performed with substantially no time lag.

The image processor 230 that functions as above comprises, for example, the aforementioned microprocessor, RAM, ROM, hard disk drive, circuit board, and so on. A computer program that causes the microprocessor to perform the above functions is stored in the storage device such as the hard disk drive in advance.

(User Interface)

A user interface 240 comprises the display 240A and the operation part 240B. The display 240A is configured to include a display device of the aforementioned arithmetic and control unit 200 and/or the display device 3. The operation part 240B is configured to include an operation device of the aforementioned arithmetic and control unit 200. The operation part 240B may also comprise various kinds of buttons, keys, etc. that are provided with the case of the fundus observation apparatus 1 or outside thereof. For example, when the retinal camera unit 2 has a case that is similar to conventional retinal cameras, a joy stick, operation panel, etc. provided with the case may also be included in the operation part 240B. Furthermore, the display 240A may also include various display devices such as a touch panel monitor etc. provided with the case of the retinal camera unit 2.

The display 240A and the operation part 240B do not need to be configured as separate components. For example, like a touch panel, it is possible to apply a device in which the display function and the operation function are integrated. In this case, the operation part 240B is configured to include a touch panel and a computer program. A content of operation to the operation part 240B is input into the controller 210 as an electrical signal. Further, operations and/or information input may be carried out by using a GUI displayed on the display 240A and the operation part 240B.

[Scanning with Signal Light and OCT Images]

Here, scanning with the signal light LS and OCT image are explained.

The scanning modes of the signal light LS by the fundus observation apparatus 1 may include, for example, horizontal scan, vertical scan, cruciform scan, radial scan, circular scan, concentric scan, helical scan, etc. These scanning modes are selectively used as necessary taking into account an observation site of a fundus, an analysis target (retinal thickness etc.), time required for scanning, the density of scanning, and so on.

The horizontal scan is one for scanning the signal light LS in the horizontal direction (x-direction). The horizontal scan includes a mode of scanning the signal light LS along multiple scanning lines extending in the horizontal direction arranged in the vertical direction (y-direction). In this mode, the interval of scanning lines may be arbitrarily set. Further, by setting the interval between adjacent scanning lines to be sufficiently narrow, it is possible to form the aforementioned three-dimensional image (three-dimensional scan). The vertical scan is performed in a similar manner.

The cruciform scan is one for scanning the signal light LS along a cross-shape trajectory consisting of two linear trajectories (line trajectories) orthogonal to each other. The radial scan is one for scanning the signal light LS along a radial trajectory consisting of multiple line trajectories arranged at predetermined angles. It should be noted that the cruciform scan is an example of the radial scan.

The circular scan is one for scanning the signal light LS along a circular trajectory. The concentric scan is one for scanning the signal light LS along multiple circular trajectories arranged concentrically around a predetermined center position. The circular scan is an example of the concentric scan. The helical scan is one for scanning the signal light LS along a helical trajectory while making the turning radius gradually smaller (or greater).

Since the galvano scanner 42 is configured to scan the signal light LS in the directions orthogonal to each other, the galvano scanner 42 is capable of scanning the signal light LS in the x-direction and the y-direction independently. Moreover, it is possible to scan the signal light LS along an arbitrary trajectory on the xy-plane by simultaneously controlling the directions of two galvano mirrors included in the galvano mirror 42. Thus, various kinds of scanning modes as described above may be realized.

By scanning the signal light LS in the modes described above, it is possible to obtain a cross sectional image in the plane spanned by the direction along the scanning line and the depth direction (z-direction) of the fundus. Moreover, in a case in which the interval between scanning lines is narrow, it is possible to obtain the aforementioned three-dimensional image.

A region on the fundus Ef subjected to scanning by the signal light LS as above, that is, a region on the fundus Ef subjected to OCT measurement, is referred to as a scanning region. A scanning region for the three-dimensional scan is a rectangular-shaped region in which multiple horizontal scans are arranged. Furthermore, a scanning region for the concentric circular scan is a disc-shaped region surrounded by the trajectories of a circular scan of a maximum diameter. Moreover, the scanning region for the radial scan is a disc-shaped (or polygonal-shaped) region linking end positions of the scanning lines.

[Operation]

Figure 7:
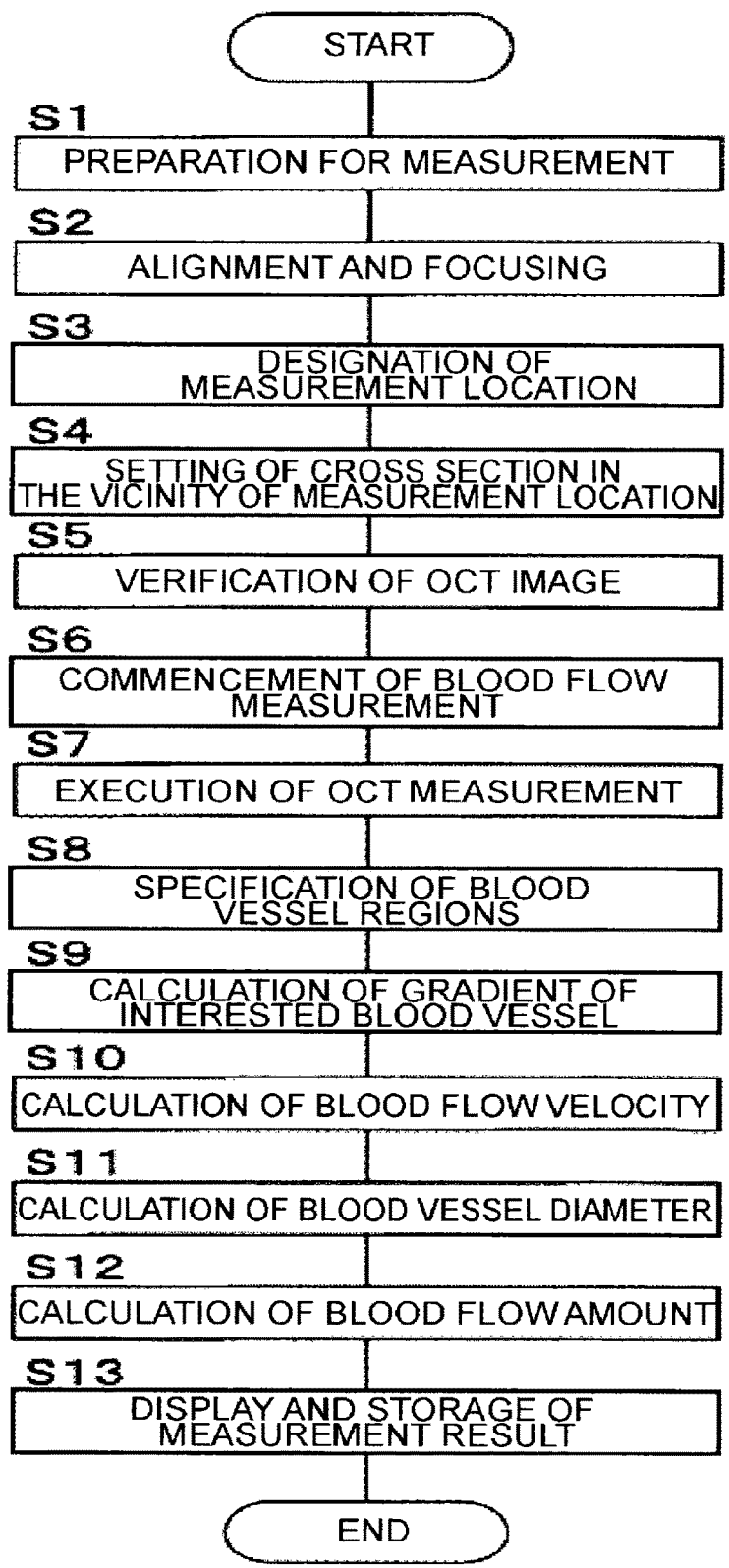
FIG. 7 is a flowchart showing the present operation.

An operation of the fundus observation apparatus 1 is described. FIG. 7 illustrates an example of the operation of the fundus observation apparatus 1.

(S1: Preparation for Measurement)

As preparation for OCT measurement, input of a patient ID, selection of operation mode corresponding to the present embodiment (blood flow measurement mode), etc. are carried out.

(S2: Alignment and Focusing)

Next, near-infrared moving image (observation image) of the fundus Ef is acquired by continuously illuminating the fundus Ef with illumination light from the observation light source 11. The main controller 211 displays this observation light on the display 240A.

At this time, the fixation target from the LCD 39, the alignment target from the alignment optical system 50 and the split target from the focus optical system 60 are projected onto the eye E. Thereby, the alignment target and split target are depicted in the observation image displayed. Alignment and focusing are carried out using these targets. It should be noted that the fixation target for observing an optic papilla is applied in the present embodiment. Here, tracking in which an optical papilla is a target may be started.

(S3: Designation of Measurement Location)

Subsequently, the user designates measurement location of blood flow onto the fundus image displayed. The location designated here is a first cross section. It should be noted that this fundus image may be an observation image or photographed image (or an image included in this). The methods of designating the first cross section are described above.

(S4: Setting of Cross Section in the Vicinity of Measurement Location)

Once the first cross section is designated, the cross section setting part 237 sets a second cross section(s) based on the first cross section.

(S5: Verification of OCT Image)

The main controller 211 controls the light source unit 101, the galvano scanner 42, etc. to carry out OCT measurement. This OCT measurement is performed for the first cross section, the second cross sections, or a cross section other than these. Verification whether a suitable OCT image is acquired is performed by referring to this OCT image. This verification may be carried out by visual observation or may be automatically carried out by the fundus observation apparatus 1.

When carried out by visual observation, the main controller 211 displays this OCT image on the display 240A. The user evaluates position displayed on the frame, image quality of the OCT image, and so on, and inputs the result of the verification using the operation part 240B. When a suitable image is not acquired, adjustment of measurement conditions is carried out. When the displayed position of the image is not suitable, the optical length of the signal light LS is changed by the optical path length changing part 41. Further, when the image quality is not suitable, the optical attenuator 105 and/or the polarization controller 106 are/is adjusted.

In the case of automatic execution, the displayed position, image quality, etc. are evaluated with referring to a preset evaluation standard, and measurement conditions are adjusted based on the evaluation result in the same fashion as in the case of manual execution.

(S6: Commencement of Blood Flow Measurement)

Blood flow measurement is started in response to a predetermined trigger.

(S7: Execution of OCT Measurement)

The blood flow measurement is begun with OCT measurement for the first cross section and the second cross sections to form a first cross sectional image, a second cross sectional image and a phase image.

(S8: Specification of Blood Vessel Regions)

The blood vessel region specifying part 231 specifies a blood vessel region from each of the first cross sectional image, the second cross sectional image and the phase image.

(S9: Calculation of Gradient of Interested Blood Vessel)

The gradient calculating part 233 calculates the gradient of the interested blood vessel at the first cross section based on the distance between cross sections and the specification result of the blood vessel region.

(S10: Calculation of Blood Flow Velocity)

The blood flow velocity calculating part 234 calculates blood flow velocity of the blood that flows within the interested blood vessel at the first cross section based on chronological variation of phase difference that is obtained as the phase image and the gradient of the interested blood vessel.

(S11: Calculation of Blood Vessel Diameter)

The blood vessel diameter calculating part 235 calculates the diameter of the interested blood vessel at the first cross section based on a fundus image or a cross sectional image (the first cross sectional image etc.).

(S12: Calculation of Blood Flow Amount)

The blood flow amount calculating part 236 calculates flow amount of blood that flows within the interested blood vessel based on calculation result of blood flow velocity and the calculation result of blood vessel diameter.

(S13: Display and Storage of Measurement Result)

The main controller 211 displays blood flow information including the calculation result of blood flow velocity, the calculation result of blood flow amount, etc. on the display 240A. Further, the main controller 211 associates the blood flow information with the patient ID and stores it in the storage 212. This is the end of the processing related to the blood flow measurement of the present embodiment.

[Effects]

Effects of the fundus observation apparatus 1 are explained.

The fundus observation apparatus 1 includes the optical system for OCT measurement, the galvano scanner 42, the image forming part 220, the blood vessel region specifying part 231 and the blood flow information generating part 232.

The optical system for OCT measurement splits light from the light source unit 101 into the signal light LS and the reference light LR, and detects the interference light LC between scattered light of the signal light LS from the fundus Ef and the reference light LR having traveled by way of the reference optical path.

The galvano scanner 42 carries out a first scan. In the first scan, a first cross section that crosses an interested blood vessel in the fundus Ef is repeatedly scanned with the signal light LS.

The image forming part 220 forms a first cross sectional image and a phase image. The first cross sectional image expresses chronological variation of morphology of the first cross section and is formed based on detection results of the interference light LC acquired by the optical system during the first scan. The phase image expresses chronological variation of phase difference of the first cross section and is formed based on detection results of the interference light LC acquired by the optical system during the first scan.

The blood vessel region specifying part 231 specifies a blood vessel region corresponding to the interested blood vessel for each of the first cross sectional image and the phase image.

The blood flow information generating part 232 generates blood flow information related to the interested blood vessel based on the blood vessel region of the first cross sectional image and the chronological variation of phase difference within the blood vessel region of the phase image. This is a basic action of the present embodiment.

The galvano scanner 42 may be configured to carry out a second scan in addition to the first scan. In the second scan, a second cross section is scanned with the signal light LS, wherein the second cross section crosses the interested blood vessel and is located in the vicinity of the first cross section. In this case, the image forming part 220 forms a second cross sectional image in addition to the first cross sectional image and the phase image. the second cross sectional image expresses morphology of the second cross section and is formed based on the detection results of the interference light LC acquired by the optical system during the second scan. Further, the blood vessel region specifying part 231 carries out specification of a blood vessel region corresponding to the interested blood vessel in the second cross sectional image as well. The blood flow information generating part 232 generates the blood flow information based on the distance between the first cross section and the second cross section, the blood vessel region of the first cross sectional image, the blood vessel region of the second cross sectional image, and the chronological variation of phase difference expressed by the phase image.

The blood flow information generating part 232 may be configured as follows: (1) the blood flow information generating part 232 includes the gradient calculating part 233 that is configured to calculate gradient of the interested blood vessel at the first cross section based on the distance between the first cross section and the second cross section, the blood vessel region of the first cross sectional image and the blood vessel region of the second cross sectional image; (2) the blood flow information generating part 232 generates the blood flow information based on calculation result of the gradient and the chronological variation of phase difference.

The second cross section may include a cross section located in the upstream of the interested blood vessel from the first cross section and a cross section located in the downstream.

The gradient calculating part 233 may be configured to calculate the gradient of the interested blood vessel at the first cross section based on location of the blood vessel region of the first cross sectional image and location of the blood vessel region of the second cross sectional image.

The blood flow information generating part may include the blood flow velocity calculating part 234 that is configured to calculate blood flow velocity of the blood that flows within the interested blood vessel at the first cross section based on calculation result of the gradient of the interested blood vessel obtained by the gradient calculating part 233 and the chronological variation of phase difference.

The blood flow velocity calculating part 234 may be configured to generate blood flow velocity variation information that expresses chronological variation of the blood flow velocity based on the chronological variation of phase difference.

The blood flow velocity calculating part 234 may be configured to calculate a statistic of the blood flow velocity based on the blood flow velocity variation information.

The fundus camera unit 2 photographs a site of the fundus Ef including the location of the first cross section. In this case, the blood vessel diameter calculating part 235 and the blood flow amount calculating part 236 in the blood flow information generating part 232 function as follows. The blood vessel diameter calculating part 235 calculates diameter of the interested blood vessel at the first cross section based on the image photographed by the retinal camera unit 2. Further, the blood flow amount calculating part 236 calculates amount of blood flow within the interested blood vessel based on the blood flow velocity variation information and the calculation result of the diameter.

Instead of this, it may be configured that the blood vessel diameter calculating part 235 calculates diameter of the interested blood vessel at the first cross section based on the first cross sectional image and the blood flow amount calculating part 236 calculates amount of blood flow within the interested blood vessel based on the blood flow velocity variation information and the calculation result of the diameter.

The blood vessel region specifying part 231 may be configured to analyze the first cross sectional image to specify blood vessel region, specify image region of the phase image corresponding to the location of this blood vessel region of the first cross sectional image, and set this specified image region as blood vessel region of the phase image.

It may be configured that the first scan may be carried out over at least one cardiac cycle of the patient. In particular, when the above [Formula 2] is applied in the calculation of the blood flow amount, the maximum of the blood flow velocity in one cardiac cycle may be used.

The first cross section and the second cross section may be set in the vicinity of the optic papilla of the fundus. In conventional blood flow measurement using laser Doppler, an interested blood vessel is measured at location that is apart from an optic papilla by the optic papilla diameter (or distance more than this) according to the characteristic of the method. However, when OCT is used as the present embodiment, measurement may be carried out at closer locations to the optic papilla. Accordingly, it is considered to improve accuracy and precision of the measurement.

According to the fundus observation apparatus 1 of the present embodiment thus configured, it is possible to realize blood flow measurement with high accuracy because it is configured to carry out blood flow measurement using the first cross sectional image at the same cross section as the phase image and chronological variation of phase difference.

Further, the fundus observation apparatus 1 may have the following characteristics. Namely, the fundus observation apparatus 1 includes the optical system for OCT measurement, the galvano scanner 42, the image forming part 220, the retinal camera unit 2, the blood vessel region specifying part 231, the blood flow velocity calculating part 234, the blood vessel diameter calculating part 235 and the blood flow amount calculating part 236.

The optical system for OCT measurement splits light from the light source unit 101 into the signal light LS and the reference light LR, and detects the interference light LC between scattered light of the signal light LS from the fundus Ef and the reference light LR having traveled by way of the reference optical path.

The galvano scanner 42 carries out a first scan and a second scan. In the first scan, a first cross section that crosses an interested blood vessel in the fundus Ef is repeatedly scanned with the signal light LS In the second scan, a second cross section is scanned with the signal light LS, wherein the second cross section crosses the interested blood vessel and is located in the vicinity of the first cross section.

The image forming part 220 forms a first cross sectional image, a phase image and a second cross sectional image. The first cross sectional image expresses chronological variation of morphology of the first cross section and is formed based on detection results of the interference light LC acquired by the optical system during the first scan. The phase image expresses chronological variation of phase difference of the first cross section and is formed based on detection results of the interference light LC acquired by the optical system during the first scan. The second cross sectional image expresses morphology of the second cross section and is formed based on detection results of the interference light LC acquired by the optical system during the second scan.

The retinal camera unit 2 photographs a site of the fundus Ef including the location of the first cross section.

The blood vessel region specifying part 231 specifies a blood vessel region corresponding to the interested blood vessel for each of the first cross sectional image, the phase image and the second cross sectional image.

The blood flow velocity calculating part 234 calculates blood flow velocity of the blood that flows within the interested blood vessel at the first cross section based on the chronological variation of phase difference and the specification result of the blood vessel region (gradient of the interested blood vessel obtained from the blood vessel region).

The blood vessel diameter calculating part 235 calculates diameter of the interested blood vessel at the first cross section based on the photographed image of the site by the retinal camera unit 2.

The blood flow amount calculating part 236 calculates amount of blood flow within the interested blood vessel based on calculation result of the blood flow velocity and the calculation result of the diameter. This is a basic action of the present embodiment.

It may be configured that the first scan may be carried out over at least one cardiac cycle of the patient. In particular, when the above [Formula 2] is applied in the calculation of the blood flow amount, the maximum of the blood flow velocity in one cardiac cycle may be used.

The first cross section and the second cross section may be set in the vicinity of the optic papilla of the fundus. In conventional blood flow measurement using laser Doppler, an interested blood vessel is measured at location that is apart from an optic papilla by the optic papilla diameter (or distance more than this) according to the characteristic of the method. However, when OCT is used as the present embodiment, measurement may be carried out at closer locations to the optic papilla. Accordingly, it is considered to improve accuracy and precision of the measurement.

The imaging optical system 30 of the retinal camera unit 2 shares part of optical path with the optical system for OCT measurement. The display 240A displays an image photographed by the retinal camera unit 2. When the user designates the first cross section to the photographed image displayed by means of the operation part 240B, the cross section setting part 237 sets the second cross section based on the first cross section designated and the photographed image. The galvano scanner 42 carries out the first scan of the first cross section designated and carries out the second scan of the second cross section set.

According to the fundus observation apparatus 1 of the present embodiment thus configured, blood flow measurement may be carried out by using the first cross sectional image at the same cross section as the phase image and chronological variation of phase difference. Further, the fundus observation apparatus 1 calculates blood flow velocity based on chronological variation of phase difference and specification result of the blood vessel region, calculates the diameter of the interested blood vessel based on the photographed image, and calculates the blood flow amount based on calculation result of the blood flow velocity and calculation result of the blood vessel diameter. Accordingly, blood flow measurement with high accuracy may be realized.

[Examples of Modification]

The configuration described above is merely illustrations for favorably implementing the present invention. Therefore, it is possible to make arbitrary modification (omission, replacement, addition, etc.) within the scope of the present invention.

A modification example of method of calculating blood flow amount is described. In the present modification example, the blood flow velocity calculating part 234 generates information (blood flow velocity variation information) that expresses chronological variation of the blood flow velocity for each pixel included in the blood vessel region of the phase image. This processing may include: processing of associating pixels of multiple phase images along time series by each of pixel positions; and processing of generating the blood flow velocity variation information based on the multiple pixels along time series corresponding to the respective pixel positions. From such processing, blood flow velocity at each position in the blood vessel region of the first cross section may be obtained.

The blood flow amount calculating part 236 calculates blood flow amount for the respective pixels by time-integrating the blood flow velocity variation information for the respective pixels included in the blood vessel region. From this processing, blood flow amount at each point in the blood vessel region of the first cross section is calculated.

Further, the blood flow amount calculating part 236 calculates blood flow amount within the interested blood vessel by adding the blood flow amounts for these pixels. By this processing, blood flow amounts for the multiple pixels obtained in the prior stage are added together and the total amount of blood that flows within the blood vessel region of the first cross section.

In the above embodiment, the optical path length difference between the optical path of the signal light LS and the optical path of the reference light LR is changed by varying the position of the optical path length changing part 41; however, a method for changing the optical path length difference is not limited to this. For example, it is possible to change the optical path length difference by providing a reference mirror (reference mirror) in the optical path of the reference light and moving the reference mirror in the advancing direction of the reference light to change the optical path length of the reference light. Further, the optical path length difference may be changed by moving the retinal camera unit 2 and/or the OCT unit 100 with respect to the eye E to change the optical path length of the signal light LS. Moreover, in a case that an object is not a living site or the like, it is also effective to change the optical path length difference by moving the object in the depth direction (z-direction).

Computer programs for implementing the above embodiments can be stored in any kind of recording medium that can be read by a computer. As such recording media, for example, an optical disk, a semiconductor memory, a magneto-optic disk (CD-ROM, DVD-RAM, DVD-ROM, MO, and so on), and a magnetic storage (a hard disk, a Floppy Disk™, ZIP, and so on) can be used.

In addition, it is possible to transmit/receive this program through a network such as internet or LAN etc.

[Embodiments of Image Displaying Apparatus]

Embodiments of image displaying apparatus etc. are described in the following with referring to diagrams. It should be noted that components with the same symbol carry out similar action, so repetition of explanation is sometimes omitted.

Figure 8:
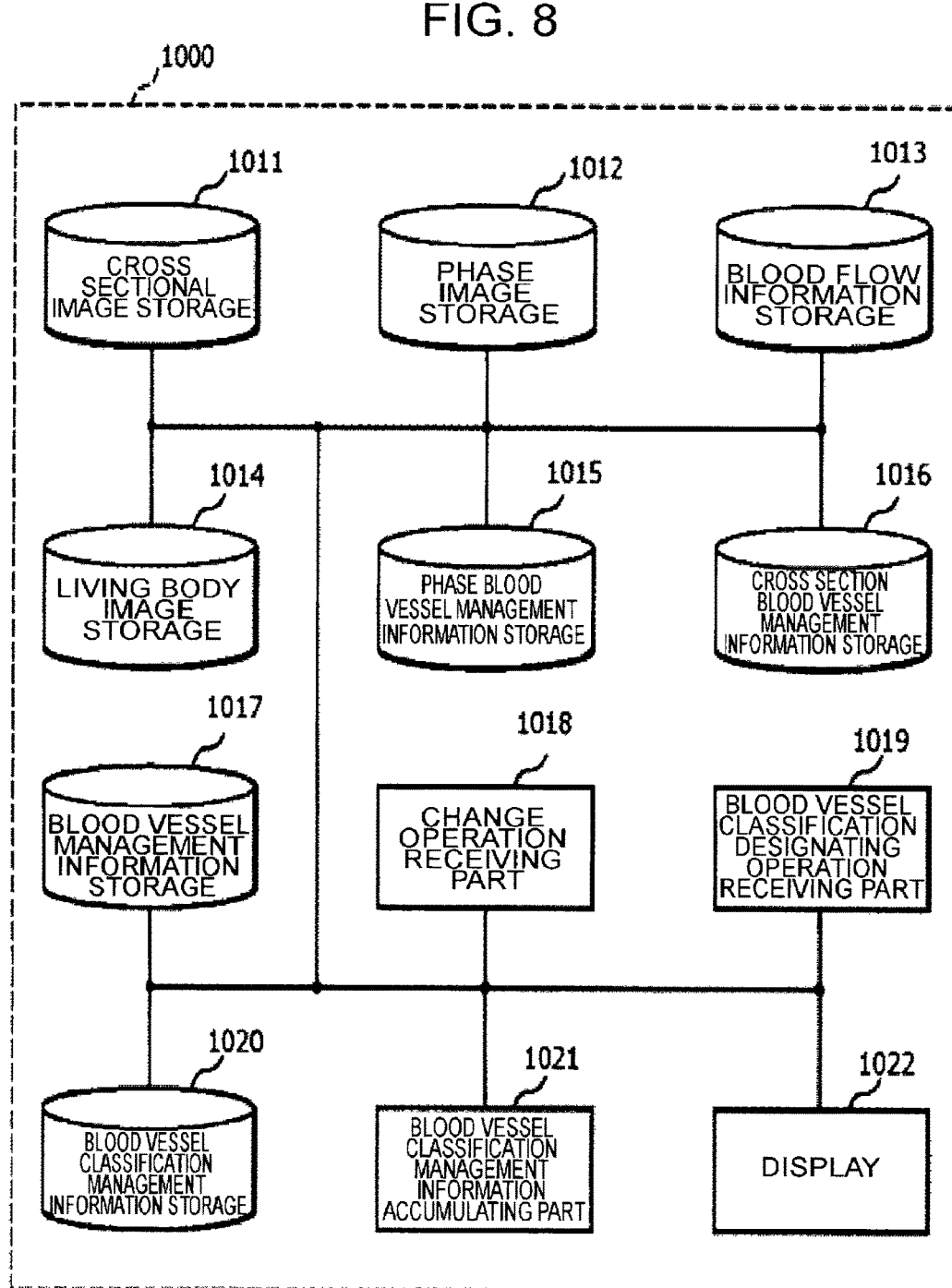
FIG. 8 is a schematic diagram showing an example of a configuration of an image displaying apparatus according to an embodiment.

FIG. 8 is a block diagram of an image displaying apparatus 1000 in the present embodiment. The present embodiment describes an example of processing of displaying a cross sectional image, phase image, blood flow information, cross section blood vessel management information, phase blood vessel management information, etc. acquired in the above embodiments. For example, images and information acquired in the above embodiment are accumulated in cross sectional image storage 1011, phase image storage 1012 and blood flow information storage 1013 etc.

The image displaying apparatus 1000 is provided with cross sectional image storage 1011, phase image storage 1012 and blood flow information storage 1013, living body image storage 1014, phase blood vessel management information storage 1015, cross section blood vessel management information storage 1016, blood vessel management information storage 1017, change operation receiving part 1018, blood vessel classification designating operation receiving part 1019, blood vessel classification management information storage 1020, blood vessel classification management information accumulating part 1021 and display 1022.

One or more cross sectional image group is stored in the cross sectional image storage 1011. A cross sectional image group includes multiple cross sectional images. A cross sectional image is an image expresses inside of a living body acquired from tomographic imaging utilizing OCT or the like, for example. For example, a cross sectional image expresses a cross section at one position in the living body. One cross sectional image group is usually includes multiple cross sectional images acquired for one location. A cross sectional image included in the cross sectional image group is an image associated with time and is a cross sectional image expresses a cross section at least one blood vessel in the living body, for example. Specifically, it is a cross sectional image expresses a cross section that crosses in the extending direction of the blood vessel. Specifically, the cross sectional image is an image of cross section of the living body that is formed, when the living body is repeatedly scanned with signal light output from laser source, based on detection results of interference light between reference light obtained from the same light source as the signal light and scattered light from the living body, and examples of processing of acquiring cross sectional images are described later.

Time associated with a cross sectional image is, for example, the time of acquisition of the cross sectional image (for example, time at which one cross sectional image is acquired using OCT apparatus). The time here may include information such as a date. A cross sectional image group is a moving image consisting of frame images that are one or more cross sectional images associated with time, for example. In this case, time may be associated with each frame image as a time code etc. The time here may be an absolute time such as some hour some minute, may be sequential identification information such as frame number, or may be a relative time that is counted from starting point of time at which one cross sectional image is output (for example, elapse of time from output of one cross sectional image). Further, time may be acquisition timing or output timing of each cross sectional image, or information in which orders of acquisition or orders of output etc. are identifiable. These matters are similar in the below. Further, multiple cross sectional images associated with time may be a file of multiple cross sectional images associated with time etc. For example, in this case, cross sectional images may be played as a moving image by reading out the file of cross sectional images by each time associated. However, a cross sectional image group may be multiple cross sectional images that individually have no information of time arranged in order of acquisition. In this case also, each cross sectional image is considered to be associated with time because time associated with each cross sectional image can be obtained from information such as starting time, frame rate etc. Such matters may be similar for phase images, blood flow information, living body images, etc. A cross sectional image stored in the cross sectional image storage 1011 is an image expressing a cross section at one or more location (site) of eye fundus, cornea etc. in the living body, for example.

Cross section management information is stored in the cross sectional image storage 1011, for example. The cross section management information includes cross sectional image group and blood vessel identification information that is information indicating one or more blood vessel intersecting the cross section expressed by this cross sectional image group. The fact that it crosses one or more blood vessel means that a cross section of one or more blood vessel is included in the cross sectional image, for example. A cross section or blood vessel here is, for example, a cross section that intersects in the direction in which one blood vessel extends. The blood vessel identification information is information such as name of blood vessel, code assigned to blood vessel, one or more coordinate indicating location of blood vessel, etc. The location of blood vessel is location of blood vessel in the living body described later, for example. It should be noted that the location here may be a place or a region. In the case of region, the blood vessel identification information may be multiple coordinate groups indicating contour of this region, multiple coordinate groups of multiple pixels included in this region. Here, ways of defining one blood vessel is not a problem so long as blood vessel is identifiable. For example, area partitioned by end or junction of blood vessel may be considered as one blood vessel, or main blood vessel and blood vessel branched from the main blood vessel may individually be regarded as one blood vessel.

It should be noted that storage here is a concept including temporal memory, for example. For example, processing of temporally storing a cross sectional image acquired by the optical image measuring apparatus 1 is also considered as storage here.

The cross sectional image storage 1011 is preferably a nonvolatile recording medium; however, volatile recording medium may also be used. It should be noted that such matters are the same for the phase image storage 1012, the blood flow information storage 1013, the living body image storage 1014, the phase blood vessel management information storage 1015, the cross section blood vessel management information storage 1016, the blood vessel management information storage 1017 and the blood vessel classification management information storage 1020 etc.

One or more phase image group is stored in the phase image storage 1012. A phase image group includes multiple phase images. A phase image is an image that is associated with time and expresses chronological variation of phase difference at a cross section intersecting at least one blood vessel in the living body. Specifically, the phase image is an image expressing chronological variation of phase difference at a cross section of the living body that is formed, when the living body is repeatedly scanned with signal light output from laser source, based on detection results of interference light between reference light obtained from the same light source as the signal light and scattered light from the living body. One living body image group is usually includes multiple living body images acquired for one location. Typically, detection results of interference light used for acquisition of phase images at one location of the living body is the same as detection results of interference light used for acquisition of cross sectional images at the same location. Therefore, position matching is possible between cross sectional images and phase images acquired at the same location in the same living body. That is, it is possible to give a natural correspondence between pixels of cross sectional images and pixels of phase images acquired at the same location. It should be noted that the same location is considered as the fact that cross section expressed by cross sectional image and cross section expressed by phase image are the same, for example. Examples of processing of acquiring phase image etc. are described later.

Time associated with a phase image is, for example, the same as the time associated with the cross sectional image that is formed from the same detection results of interference light. Alternatively, it may be time at which the phase image is acquired. A phase image group may be a moving image consisting of frame images that are one or more phase images associated with time, a file of multiple cross sectional images associated with time, multiple cross sectional images arranged in order of acquisition. A phase image stored in the phase image storage 1012 is a phase image of a cross section at one or more location (site) of eye fundus, cornea etc. in the living body, for example.

One or more phase management information is stored in the phase image storage 1012, for example. The phase management information includes, for example, phase image group and blood vessel identification information of one or more blood vessel intersecting the cross section corresponding to the phase image group.

It should be noted that storage here is a concept including temporal memory, for example. For example, processing of temporally storing a phase image acquired by the optical image measuring apparatus described later is also considered as storage here.

One or more blood flow information group is stored in the blood flow information storage 1013. A blood flow information group includes multiple blood flow information. Blood flow information is information related to flow of blood in a blood vessel in the living body. One blood flow information group is typically configured by multiple blood flow information acquired for one blood vessel of one location of one blood vessel. Blood flow information is, for example, flow velocity, flow amount etc. of blood that flows in one blood vessel. Blood flow information is associated with time. Time associated with blood flow information is, for example, time at which blood flow information is acquired. Blood flow information is generated, for example, based on chronological variation of phase difference in the region in which the cross section of blood vessel in a phase image acquired for one blood vessel. This object of calculation may be blood flow velocity at a certain point of time, or may be chronological variation of blood flow velocity (blood flow velocity variation information). In the former case, it is possible to selectively acquire blood flow velocity at a preset time phase of electro-cardiogram (such as time phase of R wave), for example. Further, in the latter case, time range is the whole or arbitrary part of scanning period with signal light for acquiring a phase image. When the blood flow velocity variation information is obtained, a statistic of blood flow velocity in the concerned time range may be calculated. Examples of this statistic include mean value, standard deviation, variance, median, maximum, minimum, local maximum, local minimum, etc. Further, histograms may be created for values of blood flow velocity. It should be noted that blood flow information stored in the blood flow information storage 1013 is preferably acquired using OCT. Details of processing of acquiring blood flow information are described later. A blood vessel in the living body here is a blood vessel in an eye fundus, cornea etc. of the living body, for example.

One or more blood flow management information is stored in the blood flow information storage 1013, for example. The blood flow management information includes, for example, blood flow information group and blood vessel identification information of blood vessel corresponding to this blood flow information group.

It should be noted that storage here is a concept including temporal memory, for example. For example, processing of temporally storing blood flow information acquired by the optical image measuring apparatus 1 etc. is also considered as storage here.

The living body image storage 1014 stores a living body image obtained by photographing a living body. A living body is an image obtained by photographing, from the front, a region including location in which a cross sectional image is acquired, for example. The front means front side of a living body (such as a human body), for example. Further, the front may be considered to be a surface onto which signal light is irradiated, wherein the signal light is scanned when performing tomographic imaging for acquiring cross sectional images etc. as described above, for example. For example, a living body image may be considered to be an image obtained by photographing a living body toward a parallel direction to the cross section expressed by a cross sectional image. For example, a living body image is a fundus image such as a fundus photograph obtained by photographing a fundus from a position facing the fundus of a living body or a cornea image obtained by photographing a cornea from a position facing the cornea of a living body and so on when the abovementioned cross sectional image is an image expressing a fundus or cornea. A living body image is preferably an image in which a blood vessel in a living body can be recognized by visual observation etc. A living body image is preferably an image obtained by photographing a location in which one or more cross sectional image, phase image, blood vessel information etc. Moreover, a living body image is preferably an image obtained by photographing a region in which one or more blood vessel included in a cross sectional image, phase image etc. or blood vessel corresponding to blood vessel information.

Further, the living body image storage 1014 may store multiple living body images associated with time. For example, the living body image storage 1014 may store a living body image group including multiple living body images associated with time. In this case, a living body image group typically includes multiple living body images acquired for one location. This location is a concept including a region and an object. Further, this living body image group may be a moving image similar to the abovementioned cross sectional image group.

The phase blood vessel management information storage 1015 stores phase blood vessel management information. The phase blood vessel management information includes phase blood vessel location information that expresses location of a blood vessel in a phase image and blood vessel identification information of this blood vessel. The phase blood vessel management information may further include identification information for identifying a corresponding phase image. The identification information of a phase image may be a code or file name etc. individually assigned to a phase image, or a combination of identification information for identifying the phase image group to which the phase image belongs (for example, file name indicating the phase image group or name of directory in which phase images in the phase image group is stored when the phase image group is a moving image) and time or frame number etc. associated with the respective phase images. However, the identification information of a phase image may be any kind of information as long as phase images are identifiable.

It may be configured to utilize phase blood vessel location information set to one phase image in one phase image group as phase blood vessel location information of other phase images in the same phase image group. In other words, common phase blood vessel location information may be set for the respective phase images in one phase image group. In such a case, identification information of individual phase image is not necessary. However, the phase blood vessel management information preferably includes identification information of phase image group as identification information of phase images when multiple phase images correspond to one blood vessel identification information.

It does not matter how phase blood vessel location information is obtained. For example, phase blood vessel location information may be obtained as information indicating location on a blood vessel in phase image designated by hand etc. using a mouse or brush cursor, or may be obtained by detecting a region including characteristic pixels as blood vessel from phase image using algorithm for detecting a region according to brightness etc. of pixels, for example. Further, phase blood vessel location information may be obtained individually for the respective phase information by the processing etc., or phase blood vessel location information indicating the same location (region) as phase blood vessel location information obtained for one phase image may be set as phase blood vessel location information of other phase image in the same phase image group. It should be noted that examples of processing of detecting location of blood vessel in phase image and setting phase blood vessel location information are described later.

The cross section blood vessel management information storage 1016 stores cross section blood vessel management information including cross section blood vessel location information that expresses location of a blood vessel in cross sectional image and blood vessel identification information of blood vessel. The cross section blood vessel management information may further include identification information for identifying a corresponding cross sectional image. The identification information etc. of a cross sectional image is same as the abovementioned identification information of phase image, so detailed description is omitted. Further, acquisition etc. of cross section blood vessel location information is also same as the abovementioned phase blood vessel location information, so detailed description is omitted. It should be noted that examples of processing of detecting location of blood vessel in cross sectional image and setting cross section blood vessel location information are described later.

The blood vessel management information storage 1017 stores one or more blood vessel management information. The blood vessel management information includes blood vessel location information that expresses location of at least one blood vessel in the living body image stored in the living body image storage 1014 and blood vessel identification information corresponding to blood vessel. Location of blood vessel is typically a region on one blood vessel in the living body; however, it may be one site (coordinate) on blood vessel. Here, a method of defining area of one blood vessel is arbitrary as long as identification is possible as described above. Further, blood vessel management information may include identification information for identifying corresponding living body. It should be noted that, for example, when living body images stored in the living body image storage 1014 configures multiple living body images (living body image group) associated with time that are obtained by photographing one site in the living body (for example, living body image group that is a moving image with frames of living body images is stored), it is possible to utilize blood vessel location information associated with one living body image as blood vessel location information of other living body images belonging to the same living body image group. That is, common phase blood vessel location information may be set for the respective living body images configuring one living body image group. In this case, identification information for identifying living body image group is used as identification information for identifying living body images.

It does not matter how blood vessel location information is obtained. For example, blood vessel location information may be obtained as location on a blood vessel in living body image designated by hand etc. using a mouse or brush cursor, or may be obtained by detecting a region including characteristic pixels as blood vessel from living body image using algorithm for detecting a region according to brightness etc. of pixels, for example. Further, blood vessel location information may be obtained individually for the respective living body information by the processing etc., or blood vessel location information indicating the same location (region) as blood vessel location information obtained for one living body image may be set as blood vessel location information of other living body image in the same living body image group. It should be noted that examples of processing of detecting location of blood vessel in living body image and setting blood vessel location information are described later.

The change operation receiving part 1018 receives a change operation for changing display of one of cross sectional image, phase image and blood flow image that are displayed by the display 1022 described later. Specifically, the change operation is an operation carried out to one image and an operation in which the same change as this operation is carried out to other images. Blood flow image may be a graph or list etc. expressing chronological variation of blood flow information that is created using one or more blood flow information included in one blood flow information group. Details of blood flow image are described later. The operation to any one of cross sectional image, phase image and blood flow image displayed by the display 1022 is, for example, clicking, dragging etc. using a mouse, tapping etc. using touch panel etc., character inputting etc. using keyboard etc. to a region (or location in the vicinity thereof) in which any one of cross sectional image, phase image and blood flow image are displayed on a display device such as a monitor (illustration omitted) etc. The operation to any one of cross sectional image, phase image and blood flow image may also be an operation of a button or pull-down menu displayed in one image.

The operation for changing display is, for example, an operation for changing displayed image. The operation for changing displayed image is, for example, an operation for changing one image currently displayed that is a target of operation to an image of the same kind that is associated with different blood vessel identification information. Here, the image of the same kind means the three kinds, namely cross sectional image, phase image and blood flow image.

For example, the change operation receiving part 1018 receives, as the change operation, an operation for designating a blood vessel to any one of cross sectional image, phase image and blood flow image that are displayed by the display 1022. Then, the change operation receiving part 1018 obtains blood vessel identification information corresponding to the blood vessel designated by the change operation of designating a blood vessel. The change operation of designating a blood vessel may be an arbitrary predetermined operation and it is, for example, an operation of sliding displayed cross sectional image or phase image in the vertical direction, horizontal direction, etc. Further, it may be an operation of pushing a button for changing blood vessel displayed in cross sectional image, phase image and blood flow image being displayed, or an operation of selecting one blood vessel from a selection list of blood vessels. Upon receiving such an operation, the change operation receiving part 1018 obtains, from the cross section management information (or phase management information), blood vessel identification information different from blood vessel identification information corresponding to the cross sectional image group (or phase image group) to which the cross sectional image (or phase image) being displayed belongs.

Further, the operation for changing an image displayed is, for example, an operation for changing one image (target of operation) to an image associated with time different from time associated with this one image.

For example, the change operation receiving part 1018 receives a change operation of designating time to any one of cross sectional image, phase image and blood flow image that are displayed by the display 1022. Then, the change operation receiving part 1018 obtains time corresponding to the change operation. The change operation of designating time may be an arbitrary predetermined operation, and, for example, when displayed blood flow image is a graph associated with time axis, the change operation is an operation of designating location of the graph other than the position indicating time corresponding to cross sectional image currently displayed by clicking using a mouse etc. or tapping on a touch panel. Alternatively, when blood flow information is a list indicating multiple blood flow information associated with time, the change operation is an operation of designating time other than the time corresponding to cross sectional image currently displayed by clicking using a mouse etc. Upon receiving such an operation, the change operation receiving part 1018 obtains, as the time corresponding to the change operation, a value of time at a projected position of the designated position onto the time axis. Further, the change operation of designating time may be an operation of sliding displayed cross sectional image or phase image in the vertical direction, horizontal direction, etc. Alternatively, the change operation of designating time may be an operation of sliding a slider bar (illustration omitted) indicating current playback time in the whole playback time of cross sectional image group or phase image group that is a moving image and being displayed in association with cross sectional image or phase image being displayed.

Further, in the case in which the display 1022 sequentially synchronizes times associated with cross sectional images and phase images and displays the cross sectional images and the phase images with preset frame rate, the change operation receiving part 1018 receives a frame rate change operation for changing frame rate for displaying cross sectional images and phase images. The operation for changing frame rate is, for example, an operation of sliding a slider bar indicating frame rate that is displayed on cross sectional image or phase image using a mouse etc., an operation of pushing a button for receiving change of frame rate that is displayed on or near cross sectional image or phase image using a mouse etc., or an operation of inputting a value of frame rate in a field for imputing a value that is displayed on cross sectional image or phase image using a keyboard etc. Upon receiving the frame rate change operation, the change operation receiving part 1018 obtains a value of frame rate after the change, for example.

Further, the change operation receiving part 1018 may be configured to receive phase blood vessel designating operation that is an operation of designating location of a blood vessel in phase image displayed by the display 1022. The operation of designating location of a blood vessel is, for example, an operation of clicking one or more sites on a region in a phase image in which a blood vessel is displayed using a mouse or surrounding the same using a mouse etc. Upon receiving the phase blood vessel designating operation, the change operation receiving part 1018 obtains blood vessel identification information corresponding to the location designated by the phase blood vessel designating operation from the phase blood vessel management information stored in the phase blood vessel management information storage 1015. For example, blood vessel location information including a coordinate clicked by a mouse etc. is detected from the phase blood vessel management information, and blood vessel identification information corresponding to the detected phase blood vessel location information is obtained from the phase blood vessel management information.

Further, as described later, when the display 1022 superposes and displays a cross sectional image and a phase image, the change operation receiving part 1018 may receive a change operation, that is an operation of changing display, to any one of the superposed image of the cross sectional image and the phase image displayed by the display 1022 and blood flow image. In this case, the change operation receiving part 1018 may receive substantially the same change operation as that received for a cross sectional image and a phase image as above. Further, when the change operation is performed on the superposed image, the change operation receiving part 1018 may carry out processing similar to that in the case of receiving the change operation performed on a cross sectional image or a phase image (for example, processing of obtaining blood vessel identification information, etc.).

For example, the change operation receiving part 1018 may receive blood vessel change designating operation that is an operation of designating a blood vessel in the image superposed by the display. The blood vessel change designating operation is, for example, an operation of designating location of blood vessel in the superposed image. Upon receiving the blood vessel change designating operation, the change operation receiving part 1018 obtains blood vessel identification information corresponding to the location indicated by the blood vessel change designating operation in the similar way as above. The change operation receiving part 1018 may obtain blood vessel identification information corresponding to the location indicated by the blood vessel change designating operation from any of the cross sectional image and the phase image superposed. Further, the change operation receiving part 1018 may receive an operation for instructing superposition of a cross sectional image and a phase image.

Moreover, the change operation receiving part 1018 may be configured to receive blood vessel designating operation that is an operation of designating a location on one blood vessel in a living body image displayed by the display 1022. The operation of designating a location on one blood vessel is, for example, an operation of clicking one or more sites on a region in a phase image in which one blood vessel is displayed using a mouse or surrounding the same using a mouse etc. Upon receiving the blood vessel designating operation, the change operation receiving part 1018 obtains blood vessel identification information corresponding to the location designated by the blood vessel designating operation from the blood vessel management information stored in the blood vessel management information storage 1017. For example, blood vessel location information including a coordinate clicked by a mouse etc. is detected from the blood vessel management information, and blood vessel identification information corresponding to the detected blood vessel location information is obtained from the phase blood vessel management information.

Here, reception of operations is a concept including: reception of information input from input devices such as a keyboard, mouse, touch panel etc.; reception of information transmitted through cable or radio communication; and reception of information read out from recording media such as an optical disk, magnetic disk, semiconductor memory, etc. An input means for receiving an operation may be arbitrary such as a numeric keypad, keyboard, mouse, menu screen, etc. The change operation receiving part 1018 may be realized by a device driver of an input means such as a numeric keypad, keyboard, etc. or a control software of a menu screen etc. The same applies to other receiving parts such as the blood vessel classification designating operation receiving part 1019 etc. described later. Further, the change operation receiving part 1018 may comprise an MPU and/or memory for executing the above processing, the procedure thereof is typically realized by software, and this software is recorded in a recording media such as a ROM etc. However, it may be realized by hardware (dedicated circuits).

The blood vessel classification designating operation receiving part 1019 receives blood vessel classification designating operation that is an operation of designating location of a vein or an artery in living body image displayed by the display 1022 described later. The operation of designating location of a vein in the blood vessel classification designating operation is, for example, an operation of clicking one or more sites on a region in a living body image, displayed by the display 1022 described later, in which vein is displayed using a mouse or surrounding the same using a mouse etc. Similarly, the operation of designating location of an artery in the blood vessel classification designating operation is, for example, an operation of clicking one or more sites on a region in a living body image, displayed by the display 1022 described later, in which artery is displayed using a mouse or surrounding the same using a mouse etc. For example, in the case in which an operation of designating location on a living body image by using a mouse etc after giving an instruction of performing an operation of designating a vein to the blood vessel classification designating operation receiving part 1019, this operation becomes an operation of designating a vein. The same applies to the operation of designating an artery.

The blood vessel classification management information storage 1020 stores blood vessel classification management information including blood vessel identification information and blood vessel classification information that expresses whether a blood vessel is a vein or an artery. Moreover, the blood vessel identification information may further include information that indicates the fact that determination of whether a blood vessel is a vein or an artery has not been carried out.

The blood vessel classification management information accumulating part 1021 obtains blood vessel identification information corresponding to the location designated by the blood vessel designating operation from the blood vessel management information stored in the blood vessel management information storage 1017, and accumulates, in the blood vessel classification management information storage 1020, blood vessel classification management information including the obtained blood vessel identification information and the blood vessel classification information that expresses the blood vessel designating operation received by the blood vessel classification designating operation receiving part 1019 (that is, information that expresses whether the blood vessel designated by the blood vessel designating operation is a vein or an artery). For example, the blood vessel classification management information accumulating part 1021 obtains, from a living body image, information that expresses a coordinate or coordinate group of the designated location(s) or the like as information that expresses the location designated by the blood vessel designating operation, detects blood vessel location information including information indicating the location obtained in the above from blood vessel management information corresponding to a living body image that becomes a target of operation received as blood vessel designating operation, and obtains blood vessel identification information corresponding to the detected blood vessel location information. Then, the blood vessel management information associating the obtained blood vessel identification information with blood vessel classification information corresponding to the blood vessel designating operation is accumulated in the blood vessel management information storage 1017. The blood vessel classification information corresponding to the blood vessel designating operation is, for example, information that expresses whether the blood vessel corresponding to the location indicated by blood vessel classifying operation received before or after blood vessel classifying operation is a vein or an artery.

The blood vessel classification management information accumulating part 1021 is typically realized by an MPU and memory etc. The procedure of the blood vessel classification management information accumulating part 1021 is typically realized by software, and this software is recorded in recording media such as ROM etc. However, it may be realized by hardware (dedicated circuits).

The display 1022 synchronously displays cross sectional image included in cross sectional image group and phase image included in phase image group using time associated with the cross sectional image and the phase image, and displays a blood flow image that is an image expressing multiple blood flow information, from among blood flow information included in blood flow information group, associated with time within a period including time associated with the cross sectional image and the phase image being displayed. For example, the display 1022 preferably displays a cross sectional image and a phase image that are acquired at the same period and for the same site. Further, the display 1022 preferably displays blood flow image that is expressed by blood flow information associated with the same period of blood vessel included in the same site as the site for which the cross sectional image and the phase image are acquired. Here, more preferably, the same period is the same time. Further, the same site here may be considered to include adjacent location with position gap like an error; however, it is preferably the matched location.

Synchronously Displaying cross sectional image and phase image using time associated with the cross sectional image and the phase image means displaying the cross sectional image and the phase image both associated with the same time, for example. Further, typically, cross sectional images included in cross sectional image group and phase images included in phase image group are sequentially displayed, with the same frame rate, so as to synchronize times associated with each other. The display 1022 may display one cross sectional image and one phase image as still images, or may display cross sectional image and phase image as moving images by sequentially reading out and displaying cross sectional images in one cross sectional image group and phase images one phase image group.

The blood flow image an image created using multiple blood flow information, and, for example, a graph expressed in coordinate system in which multiple blood flow information associated with time are expressed with the first axis showing time and the second axis showing values of blood flow information, a list in which multiple blood flow information associated with time are arranged and expressed in ascending order descending order of time, or the like. Next, the display 1022, for example, may obtain times associates with cross sectional image and phase image displayed, obtain blood flow image associated with time within a period including the obtained time, and simultaneously display the cross sectional image, the phase image and the blood flow image.

The inside of period including time associated with cross sectional image and phase image being displayed is a period of length previously designated so as to including this time. The inside of period including time associated with cross sectional image and phase image being displayed may be, for example, a period within a range obtained by adding a preset time to any one or both of front and rear of the times associated with cross sectional image and phase image being displayed. Further, it may be a period including times corresponding to all blood flow information associated with cross sectional image group including cross sectional image being displayed and phase image group including phase image being displayed. For example, it may be a period between the earliest time of blood flow information and the latest time thereof. For example, in the case in which cross sectional image and phase image being displayed are frame images of moving images, this period may vary in accordance with time corresponding to switched frame image (cross sectional image, phase image) every time frame image is switched, or times corresponding to cross sectional image and phase image being displayed may be updated so as not to be included in the period set immediately before.

Further, with respect to blood flow image, it is preferable to display, for example, values of blood flow information corresponding to times corresponding to cross sectional image and phase image being displayed in a different display mode from other blood flow information. The difference of display modes means displaying with distinguishable aspect from other locations, and examples thereof includes overlaying different colors or patterns from other locations and displaying surrounding closing line etc. so as to be distinguishable from other locations. For example, when blood flow image is a graph indicating blood flow information along time axis, straight lines indicating times corresponding to cross sectional image and phase image being displayed may be displayed perpendicularly to the time axis.

Further, the display 1022 may further display a living body image. When one or more living body images are associated with time, the living body images may be synchronously displayed with cross sectional image and phase image.

In the case in which cross sectional image group, phase image group and blood flow information group are associated with blood vessel identification information, in response to designation of one blood vessel identification information, the display 1022 displays cross sectional image included in cross sectional image group associated with this blood vessel identification information, phase image included in phase image group associated with this blood vessel identification information, and blood flow image included in blood flow image group associated with this blood vessel identification information, for example. Thereby, cross sectional image, phase image and blood flow image for the same blood vessel may be displayed.

It should be noted that when the display 1022 further displays a living body image, it is preferable to display a living body image for which one or more blood vessel identification information included in the blood vessel management information corresponding to this living body image coincides with blood vessel identification information corresponding to cross sectional image, phase image and blood flow image being displayed because there is relevance among images being displayed.

In embodiments, the display 1022, in particular, performs the same change as the change corresponding to the change operation to cross sectional image, phase image and blood flow image displayed by the display 1022. That is, when change operation to any one of cross sectional image, phase image and blood flow image being displayed is received by the change operation receiving part 1018, the display 1022 carries out the change corresponding to the change operation to not only the image that is the target of the change operation but also other images. In other words, it is considered that the change to one image is synchronized with other images.

For example, when the change operation receiving part 1018 receives change operation, to one image, for displaying image corresponding to one blood vessel other than blood vessel corresponding to this image, the display 1022 changes all images displayed, including the image that is a target of the change operation, to the above images corresponding to one blood vessel.

For example, the display 1022 obtains cross sectional image, phase image and blood flow image corresponding to blood flow identification information obtained by the change operation receiving part 1018 in response to change operation from cross sectional image group, phase image group and blood flow image group, and displays the images obtained. The obtainment from blood flow image group here is a concept including obtainment of image such as the above blood flow image constructed using blood flow information included in blood flow information group, for example. Specifically, the display 1022 updates the displayed image with the obtained image. It should be noted that regarding the respective images after change, it is possible to display the respective images of time corresponding to the images before change, or display the respective images of other time, for example, time corresponding to starting time of any of the images.

Further, for example, when the change operation receiving part 1018 receives change operation, to one image, for changing time that is a target of display, the display 1022 changes all images displayed, including the image that is a target of change operation, to images corresponding to the time after the above change.

For example, the display 1022 obtains cross sectional image, phase image and blood flow image corresponding to the time obtained by the change operation receiving part 1018 in response to change operation from cross sectional image group, phase image group and blood flow image group, and displays the images obtained. Specifically, currently displayed cross sectional image, phase image and blood flow image are respectively updated by the obtained images.

Further, when the change operation receiving part 1018 receives blood vessel identification information in response to change operation to phase image, the display 1022 obtains and displays blood vessel image using the blood vessel information group corresponding to this blood vessel identification information obtained.

Further, when the change operation receiving part 1018 receives blood vessel identification information in response to phase blood vessel designating operation, the display 1022 obtains cross section blood vessel location information corresponding to the obtained blood vessel identification information using cross section blood vessel management information, and displays the location indicating the obtained cross section blood vessel location information of the currently displayed cross sectional image in a different display aspect from other locations. The different display aspect is the same as above, and, for example, the location indicated by cross section blood vessel location information is overlaid in a preset color.

Further, when the change operation receiving part 1018 receives frame rate change operation, the display 1022 changes frame rates for displaying cross sectional image and phase image to the same frame rate corresponding to the change operation. For example, the display 1022 changes frame rates for displaying cross sectional image and phase image to one frame rate that is indicated by the value of frame rate obtained by the change operation receiving part 1018 in response to frame rate change operation and that is different from the current frame rate. The change in frame rate may be considered as change in reproduction speed of cross sectional images and phase images that are frame images.

Further, the display 1022 may synchronize cross sectional image included in cross sectional image group and phase image included in phase image group using times associated with cross sectional image and phase image, and superpose and display them. The superposition and display here means that contents of both images are displayed by permeability. For example, overlaying one image on the other image, or changing superposition mode from usual superposition mode and displaying images means that at least one image becomes semi-transparent and is superposed.

Further, when cross sectional image and phase image are superposed and displayed, the display 1022 may further display blood flow image that is an image expressing multiple blood flow information, from among blood flow information included in blood flow information group, associated with time within a period including time associated with cross sectional image and phase image being superposed and displayed.

Further, in the case in which cross sectional image and phase image are superposed and displayed, when change operation similar to the above is performed to one of the superposed image and blood flow image, the display 1022 may apply the same change as the change corresponding to this change operation to the superposed image of cross sectional image and phase image as well as the blood flow image displayed by the display 1022.

Further, the display 1022 may obtain blood vessel identification information and phase blood vessel location information corresponding to phase image displayed by the display 1022 from phase blood vessel management information, obtain blood vessel classification information corresponding to the blood vessel identification information from blood vessel classification management information, and display location indicated by the phase blood vessel location information corresponding to the blood vessel identification information of the phase image in a display aspect different from other locations, wherein the display aspect is switched according to whether blood vessel classification information corresponding to phase blood vessel location information is information indicating a vein or information indicating an artery. For example, it is possible to display location indicating a vein and location indicating an artery with different colors. Further, when blood vessel classification information corresponding to phase blood vessel location information is a value indicating no designation of any of vein and artery, it is possible to display the location indicated by this phase blood vessel location information in a different display aspect from vein, artery, etc. It should be noted that in this case, the display 1022 may display at least living body image and cross sectional image included in phase image group corresponding to one blood vessel identification information.

The display here is a concept including display on display devices and projection using projectors, and the like.

It may be thought that the display 1022 does or does not include a display device such as a display. The display 1022 may be realized by driver software of display device, or driver software of display device and display device. Further, the display 1022 may be provided with an MPU and memory etc.; the procedure thereof is typically realized by software, and this software is recorded in recording media such as ROM etc. However, it may be realized by hardware (dedicated circuits).

Figure 9:
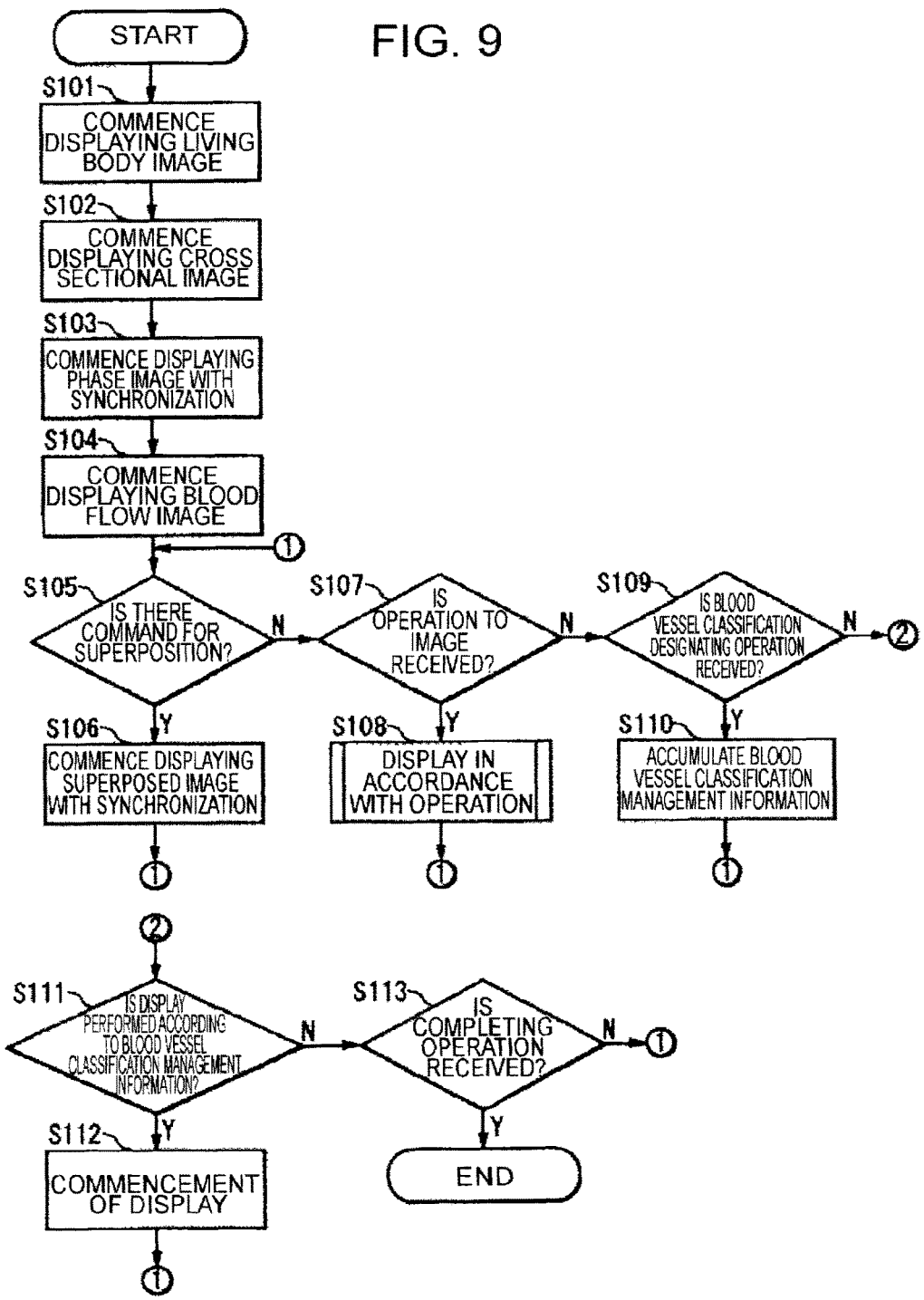
FIG. 9 is a flowchart for explaining the present operation.

Next, actions of the image displaying apparatus 1000 are described with referring to the flowchart of FIG. 9. Here, the case in which cross sectional image group and phase image group are moving images is described as an example.

(Step S101)

The display 1022 starts displaying living body image. When the living body image is a frame image of moving image associated with time, the display 1022 sequentially displays living body images with a preset frame rate.

(Step S102)

The display 1022 starts displaying cross sectional images included in cross sectional image group. The display 1022 sequentially displays cross sectional images included in cross sectional image group with a preset frame rate. When the living body images that have been started displaying in the above step is frame images, the display 1022 synchronizes the cross sectional images with the living body images and display the cross sectional images.

(Step S103)

The display 1022 starts displaying phase images included in cross sectional image group. The display 1022 sequentially displays phase images included in phase image group with a preset frame rate, and synchronizes the phase images with the cross sectional images displayed in the Step S102. For example, cross sectional image and phase image associated with the same time are displayed simultaneously. It should be noted that cross sectional image and phase image displayed by the display 1022 are images including blood vessels indicated in the living image displayed in the Step S101, for example.

(Step S104)

The display 1022 obtains time corresponding to the cross sectional image or phase image being displayed, reads out blood flow information of a period, previously designated, including this time from the blood flow information storage 1013, and displays blood flow image created using the blood flow information read out. It should be noted that in the display processing from the Step S101 to the Step S104, images related to the same time may be displayed simultaneously. In this case, the display 1022 may obtain blood flow image in accordance with time corresponding to the cross sectional image or phase image displayed in the next processing, and simultaneously display this and the cross sectional image and phase image displayed in the next processing.

(Step S105)

The change operation receiving part 1018 judges whether operation for displaying superposed image of cross sectional image and phase image is received or not. If it is received, the processing transfers to the Step S106, and if it is not received, the processing transfers to the Step S107.

(Step S106)

The display 1022 synchronizes cross sectional images and phase images with each other using times associated with these images, and superposes and sequentially displays the cross sectional images and phase images. For example, the display 1022 carries out processing of displaying the superposed image instead of individual display of cross sectional image and phase image. Then, processing returns to Step S105.

(Step S107)

The change operation receiving part 1018 judges whether or not an operation to an image displayed by the display 1022 is received. If it is received, the processing transfers to the Step S108, and if it is not received, the processing transfers to the Step S109.

(Step S108)

The image displaying apparatus 1000 execute display processing in accordance with the operation received in the Step S107. The details of this processing are described later. Then, the processing returns to the Step S105.

(Step S109)

The blood vessel classification designating operation receiving part 1019 judges whether or not a blood vessel classification designating operation is received. If it is received, the processing transfers to the Step S110, and if it is not received, the processing transfers to the Step S111.

(Step S110)

The blood vessel classification management information accumulating part 1021 obtains blood vessel classification management information corresponding to the blood vessel classification designating operation received in the Step S109, and accumulates it into the blood vessel classification management information storage 1020. Then, the processing returns to the Step S105.

(Step S111)

The display 1022 judges whether or not display processing in accordance with the blood vessel classification management information will be executed. For example, it may be configured to determine that the display processing will be carried out when the change operation receiving part 1018 has received an operation for carrying out display processing in accordance with the blood vessel classification management information. Alternatively, it may be configured to determine that the display processing will be carried out when blood vessel classification management information is accumulated. When the display processing is carried out, the processing transfers to the Step S112, and if it is not carried out, the processing transfers to the Step S113.

(Step S112)

The display 1022 carries out the display processing in accordance with blood vessel classification management information. Specifically, location in phase image that is indicated by the phase blood vessel location information of blood vessel classification management information is displayed in accordance with blood vessel classification information in a different display aspect from other locations. Then the processing returns to the Step S105.

(Step S113)

The change operation receiving part 1018 judges whether or not an operation for completing display processing by the display 1022 is received. If it is received, the processing ends, and if it is not received, the processing returns to the Step S105.

Next, details of actions corresponding to the Step S108 of FIG. 9 among actions of the image displaying apparatus 1000 are described with referring to FIG. 10.

(Step S201)

The change operation receiving part 1018 judges whether or not the received operation is a change operation. If it is a change operation, the processing transfers to the Step S202, and if it is not a change operation, the processing transfers to the Step S208.

(Step S202)

The change operation receiving part 1018 judges whether or not the received operation is a change operation for designating blood vessel. If it is a change operation for designating blood vessel, the processing transfers to the Step S203, and if it is not a change operation for designating blood vessel, the processing transfers to the Step S205.

(Step S203)

The change operation receiving part 1018 obtains blood vessel identification information of blood vessel designated by the change operation.

(Step S204)

The display 1022 changes, so as to display cross sectional image, phase image and blood flow image corresponding to the blood vessel identification information obtained in the Step S203, display objects of these images. It should be noted that in the case in which cross sectional image and phase image are superposed, processing that is substantially executed is the same except for processing of superposing and displaying these images. Then, the processing returns to upper processing.

(Step S205)

The change operation receiving part 1018 judges whether or not the received operation is a change operation for designating time. If it is a change operation for designating time, the processing transfers to the Step S206, and if it is not a change operation for designating time, the processing returns to upper processing. It should be noted that when change operation only includes one of an operation for designating blood vessel and an operation for designating time, this processing may be omitted since it can be known that the change operation is an operation for designating time in response to the judgment that it is not an operation for designating blood vessel.

(Step S206)

The change operation receiving part 1018 obtains time indicated by the change operation.

(Step S207)

The display 1022 changes times of the respective images displayed. Specifically, the display 1022 changes the display of cross sectional image, phase image and living body image to the display of cross sectional image, phase image and living body image corresponding to time obtained in the Step S206. Further, the display 1022 changes the display of blood flow image to the display of blood flow image created using blood flow information of a period including time corresponding to the changed cross sectional image or phase image. It should be noted that in the case in which cross sectional image and phase image are superposed, processing that is substantially executed is the same except for processing of superposing and displaying these images. Then, the processing returns to upper processing.

(Step S208)

The change operation receiving part 1018 judges whether or not the received operation is phase blood vessel designating operation. If it is phase blood vessel designating operation, the processing transfers to the Step S209, and if it is not phase blood vessel designating operation, the processing transfers to the Step S210. It should be noted that when cross sectional image and phase image are not superposed, phase blood vessel designating operation is not received here.

(Step S209)

The change operation receiving part 1018 obtains blood vessel identification information corresponding to phase blood vessel designating operation.

(Step S210)

The display 1022 displays blood flow image corresponding to phase blood vessel designating operation. Specifically, blood flow image is obtained using blood flow information corresponding to the blood vessel identification information obtained in the Step S209 and displayed.

(Step S211)

The display 1022 changes the display aspect of location of cross sectional image corresponding to phase blood vessel designating operation. Specifically, the display aspect of location of cross sectional image being displayed corresponding to phase blood vessel designating operation obtained in the Step S9 is changed to display aspect different from other locations. Then, the processing returns to upper processing.

(Step S212)

The change operation receiving part 1018 judges whether or not the received operation is frame rate change operation to any of cross sectional image and phase image. If it is frame rate change operation, the processing transfers to the Step S213, and if it is not frame rate change operation, the processing transfers to the Step S214. It should be noted that even when cross sectional image and phase image are superposed, frame rate change operation to at least one of cross sectional image and phase image may be received here.

(Step S213)

The display 1022 changes frame rate at the time of displaying cross sectional image and phase image to the frame rate indicated by the frame rate change operation. Then, the processing returns to upper processing.

(Step S214)

The change operation receiving part 1018 judges whether or not the received operation is blood vessel designating operation to living body image. If it is blood vessel designating operation, the processing transfers to the Step S215, and if it is not blood vessel designating operation, the processing returns to upper processing.

(Step S215)

The change operation receiving part 1018 obtains blood vessel identification information corresponding to blood vessel designating operation.

(Step S216)

The display 1022 changes, so as to display cross sectional image, phase image and blood flow image corresponding to blood vessel identification information obtained in the Step S215, a target of display of these images. It should be noted that in the case in which cross sectional image and phase image are superposed, processing that is substantially executed is the same except for processing of superposing and displaying these images. Then, the processing returns to upper processing.

It should be noted that in the flowcharts illustrated in FIG. 9 and FIG. 10, procedure of receiving operations etc. for cancelling superposition processing of cross sectional image and phase image and display processing of location in cross sectional image designated by phase blood vessel designating operation and so on, and procedure of cancelling these are omitted; however, in embodiments, it may be configured to carry out cancelling processing by receiving these cancelling operation through receiving part (not illustrated).

Specific actions of the image displaying apparatus 1000 of the present embodiment will be described in the following.

Figure 11:
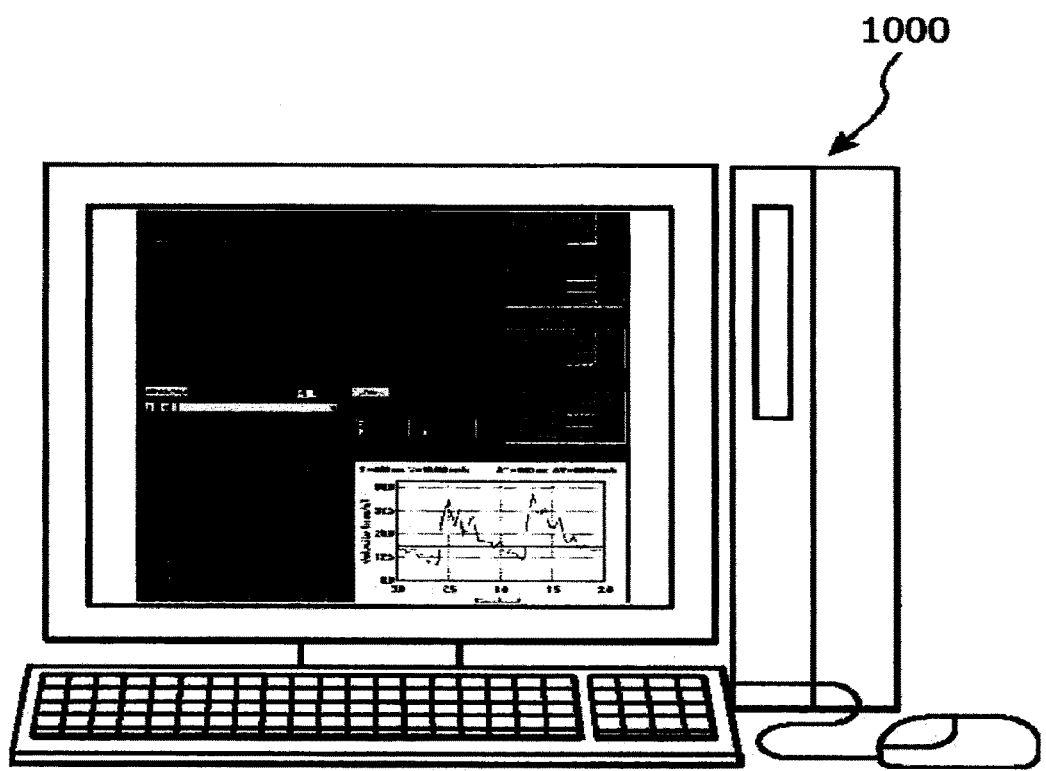
FIG. 11 is a conceptual diagram of the present embodiment.

A conceptual diagram showing an example of the image displaying apparatus 1000 of the present embodiment is illustrated in FIG. 11.

Figure 12:
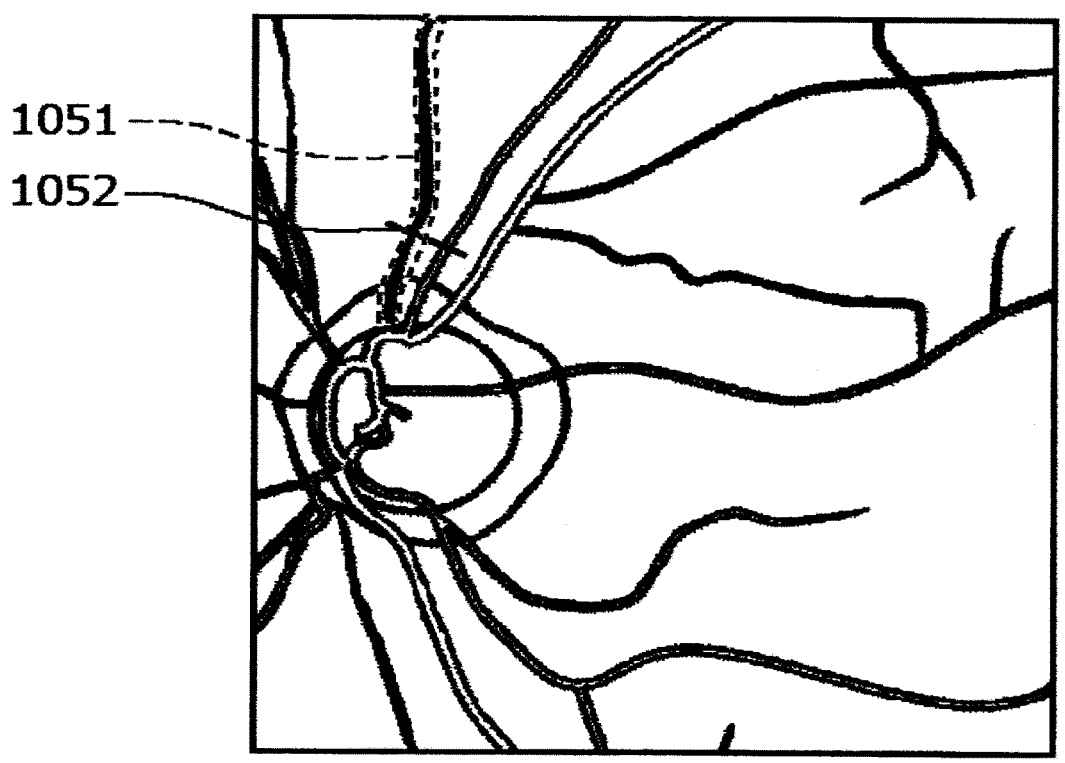
FIG. 12 is a diagram showing an example of a living body image of the present embodiment.

FIG. 12 illustrates an example of living body image stored in the living body image storage 1014. It is assumed here that living body images are fundus images acquired for a fundus of one subject, as an example. It is also assumed here that a fundus image is one frame image constructing a living body image group (fundus image group) that consisting of multiple sequential living body images. This living body image is considered to be a living body image, to which a time code "t1" is attached, among living body images configuring a living body image group named "E01" for a subject with subject identification information "P10001". Here, a time code is time attached to a living body image that is a frame image, and here, it may be expressed as a combination of "year", "month", "day", "hour", "minute", "second", "frame" and the like, for example. It should be noted here that to (n is an integer) is assumed to be a value indicating arbitrary time. Here, values with the same n indicate the same time. The same applies to the following as well. Each living body image configuring a living body image group is associated with a time code and stored in a file of the living body image group, for example. This time code is assumed here to indicate the day and time at which frame images are acquired and the day and time at which data required for acquiring frame images is acquired, for example. The same applies to time codes of other moving images. Further, living body images, cross sectional images, phase images, blood flow images etc. in the present embodiment are images created for explanation, and there are cases in which the images are different from actual data.

FIG. 13 illustrates living body image management information for managing living body images stored in the living body image storage 1014. The living body image management information includes items including "subject ID", "living body image group ID", "time code" and "living body image". The "subject ID" is identification information of subjects. The "living body image group ID" is identification information of living body image groups, and here, a living body image group configures one file and the living body image group ID is the file name thereof. Here, a living body image group associated with one "living body image group ID" consists of one or more fundus images acquired within the same period for one eyeball of one subject. The "time code" is a time code, and is information of time associated with the respective living body images configuring a living body image group, here. In this specific example, cases are described in which the combinations of the "living body image group ID" and "time code" are used as identification information of living body images. It should be noted that it may be considered that subject ID is also part of identification information of living body images. The "living body image" is a living body image associated with a combination of living body image group ID and time code, and is a frame image here.

FIG. 14 illustrates blood vessel management information stored in the blood vessel management information storage 1014. The blood vessel management information includes items including "subject ID", "living body image group ID", "time code", "blood vessel ID" and "blood vessel location information". The "subject ID", "living body image group ID" and "time code" are the same as in FIG. 13. The "blood vessel ID" is identification information of blood vessels expressed in living body images (fundus images here). The "blood vessel location information" is information indicating a region of a blood vessel corresponding to one "blood vessel ID" in a living body image, and consists of coordinate group of pixels on a blood vessel corresponding to one "blood vessel ID" in a living body image here. It should be noted that in the present embodiment, xr and xs (r and s are arbitrary integers) are assumed to be arbitrary values. The same applies to the following. For example, a region 1051 surrounded by dotted lines is assumed to be a region indicating blood vessel location information corresponding to blood vessel ID "V01" Here, the case in which blood vessel location information is attached to each frame image is described; however, it may be configured to utilize blood vessel location information that is set for one frame image also as blood vessel location information of other frame images in the same living body image group.

It should be noted that ways of acquisition of blood vessel location information from a living body image is arbitrary. For example, the user may determine, as a blood vessel, a continuous area with brightness no more than a threshold in an area traced by a cursor using a mouse etc., and obtain information defining a region in the determined area (for example, coordinates of pixels in the area, coordinates of pixels configuring a contour of the area, etc.). It is possible to appropriately designate a region on blood vessel by doing so because blood vessels typically have tendency to be expressed in lower brightness than other sites. Further, it may be configured to automatically detect a continuous area with brightness no more than a threshold in a living body image to obtain a line that connects centers in width direction of this area, and recognize the automatically detected area, an individual blood vessel, that has an interval separated by a junction and end point of this line. It should be noted that such technology may be realized by utilizing technologies such as so-called automatic tracing etc. Blood vessel identification information etc. may be automatically given in the acquisition order etc., or may be designated by the user, for example. Further, it may be configured to give blood vessel location information set for one frame image to other frame images in the same living body image group as blood vessel location information these other frame images.

Figure 15:
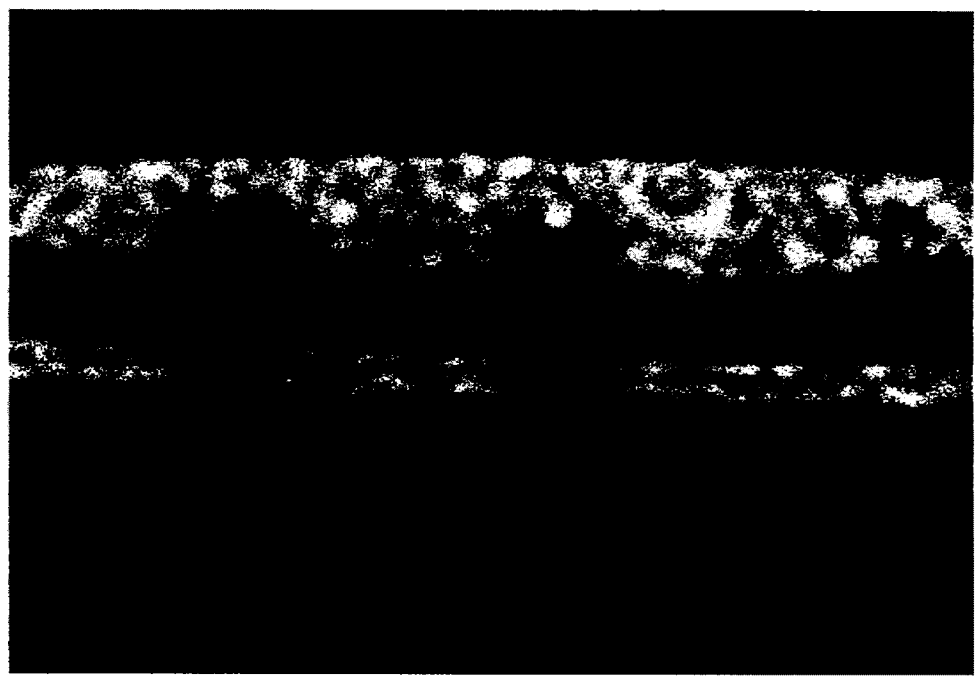
FIG. 15 is a diagram showing an example of a cross sectional image of the present embodiment.

FIG. 15 illustrates cross sectional image stored in the cross sectional image storage 1011. Here the cross sectional image is assumed to be a cross sectional image, imaged using OCT, of a cross section perpendicular to the fundus image illustrated in FIG. 12 at a location crossing one or more blood vessels in the fundus image, as an example. It should be noted that the cross sectional image is assumed to be one frame image configuring a cross sectional image group that is a moving image here. This cross sectional image is assumed to be a cross sectional image to which time code "t1" is attached among cross sectional images in the cross sectional image group with "D01" for a subject of subject identification information "P10001". Here, a cross sectional image group is assumed to configure one file, and be associated with this file name and stored in the cross sectional image storage 1011.

FIG. 16 illustrates cross section management information for managing cross sectional images stored in the cross sectional image storage 1011. The cross section management information includes items including "subject ID", "cross sectional image group ID", "time code" and "cross sectional image". The "subject ID" is identification information of subjects. The "cross sectional image group ID" is identification information of cross sectional image groups, and here, a cross sectional image group configures one file and the cross sectional image group ID is the file name thereof. Here, a cross sectional image group associated with one "cross sectional image group ID" consists of multiple cross sectional images acquired within one period for one site of one fundus of one subject. The "time code" is a time code, and is information of time associated with the respective cross sectional images configuring a cross sectional image group, here. In this specific example, cases are described in which the combinations of the "cross sectional image group ID" and "time code" are used as identification information of cross sectional images. It should be noted that it may be considered that subject ID is also part of identification information of cross sectional images. The "cross sectional image" is a cross sectional image associated with a combination of cross sectional image group ID and time code, and is a frame image here.

FIG. 17 illustrates cross section blood vessel management information stored in the cross section blood vessel management information storage 1016. The cross section blood vessel management information includes items including "subject ID", "cross sectional image group ID", "time code", "blood vessel ID" and "cross section blood vessel location information". The "subject ID", "cross sectional image group ID" and "time code" are the same in FIG. 16. The "blood vessel ID" is blood vessel identification information of blood vessels expressed in cross sectional images. The "cross section blood vessel location information" is information indicating a region of blood vessel corresponding to one "blood vessel ID" expressed in a cross sectional image, and here, is configured by coordinate group of pixels on blood vessel corresponding to one "blood vessel ID" expressed in a cross sectional image. For example, in FIG. 12, the location indicated by a line 1052 indicates a location (site) in which cross sectional image with cross sectional image group ID "D01" is acquired. Here, the case in which cross section blood vessel location information is attached to each frame image is described; however, it may be configured to utilize blood vessel location information that is set for one frame image also as cross section blood vessel location information of other frame images in the same cross sectional image group.

Figure 18:
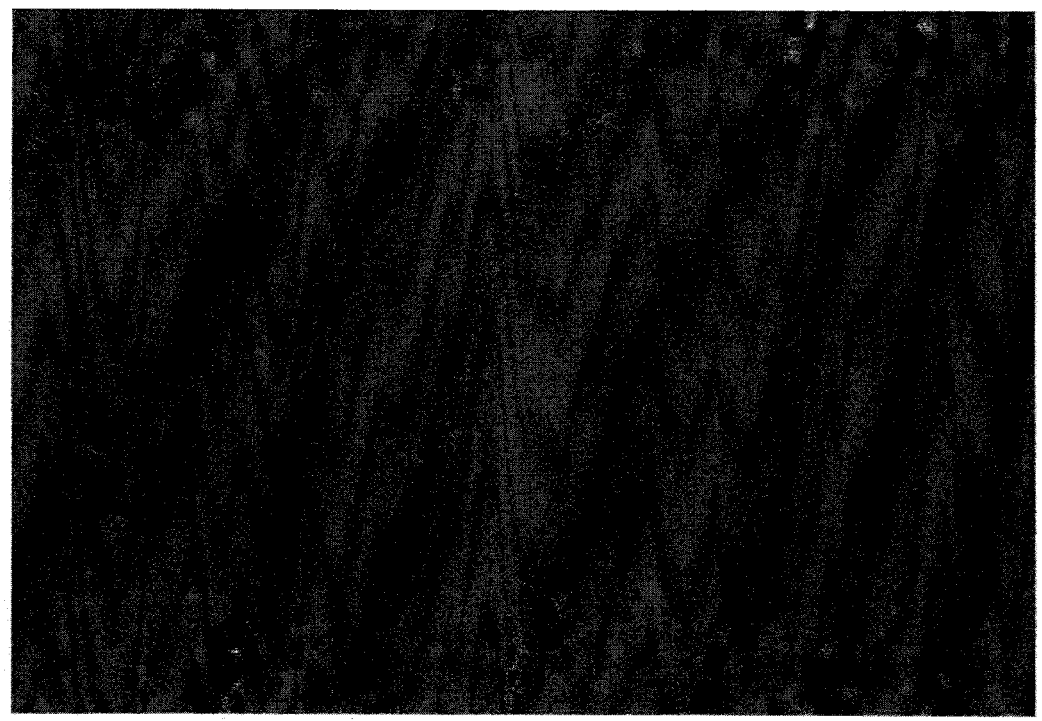
FIG. 18 is a diagram showing an example of a phase image of the present embodiment.

FIG. 18 illustrates phase image stored in the phase image storage 1012. Here the phase image is assumed to be a phase of the same location as the cross sectional image shown in FIG. 14. It should be noted that the phase image is assumed to be one frame image configuring a phase image group that is a moving image here. This phase image is assumed to be a phase image to which time code "t1" is attached among phase images in the phase image group with "D01" for a subject of subject identification information "P10001". Here, a phase image group is assumed to configure one file, and be associated with this file name and stored in the phase image storage 1012.

FIG. 19 illustrates phase management information for managing phase images stored in the phase image storage

1012. The phase management information includes items including "subject ID", "phase image group ID", "time code" and "phase image". The "subject ID" is identification information of subjects. The "phase image group ID" is identification information of phase image groups, and here, a phase image group configures one file and the phase image group ID is the file name thereof. Here, a phase image group associated with one "phase image group ID" consists of multiple phase images acquired within one period for one site of one fundus of one subject. The "time code" is a time code, and is information of time associated with the respective phase images configuring a phase image group, here. In this specific example, cases are described in which the combinations of the "phase image group ID" and "time code" are used as identification information of phase images. It should be noted that it may be considered that subject ID is also part of identification information of phase images. The "phase image" is a living body image associated with a combination of phase image group ID and time code, and is a frame image here.

FIG. 20 illustrates phase blood vessel management information stored in the phase blood vessel management information storage 1015. The phase blood vessel management information includes items including "subject ID", "phase image group ID", "time code", "blood vessel ID" and "phase blood vessel location information". The "subject ID", "phase image group ID" and "time code" are the same in FIG. 19. The "blood vessel ID" is blood vessel identification information of blood vessels expressed in phase images. The "phase blood vessel location information" is information indicating a region of blood vessel corresponding to one "blood vessel ID" expressed in a phase image, and here, is configured by coordinate group of pixels on blood vessel corresponding to one "blood vessel ID" expressed in a phase image. Here, the case in which phase blood vessel location information is attached to each frame image is described; however, it may be configured to utilize blood vessel location information that is set for one frame image also as phase blood vessel location information of other frame images in the same phase image group. Further, in the case in which phase images corresponding to one time are acquired in accordance with cross sectional image associated with the same time, it may be configured to use cross section blood vessel location information set for a cross sectional image acquired in the same location associated with the same time as phase blood vessel location information of phase image of blood vessel.

FIG. 21 illustrates blood flow information management information stored in the blood flow information storage 1013. The blood flow information management information includes items including "subject ID", "blood flow information group ID", "time code", "blood vessel ID" and "blood flow information". Here, it is assumed that blood flow information included in one blood flow information group configures one file, and "blood flow information group ID" is the file name thereof. Here, a blood flow information group associated with one "blood flow information group ID" consists of multiple blood flow information acquired within one period for one site of one fundus of one subject. Here, cases are described in which the combinations of the "blood flow information group ID" and "time code" are used as identification information of blood flow information. It should be noted that it may be considered that subject ID is also part of identification information of blood flow information. The "blood flow information" is blood flow information, and here, is flow velocity as an example.

It should be noted that a value "sp" (p is an arbitrary integer) is an arbitrary value indicating flow velocity of blood.

For example, suppose that the user carries out an operation for displaying an image corresponding to the subject ID "P10001" using a receiving part (not illustrated) of the image displaying apparatus 1000.

The display 1022 reads out living body images in the order from the record indicating "time code" of the earliest time among records (rows) corresponding to the subject ID "P10001" of living body management information shown in FIG. 13, and sequentially displays them with a preset frame rate. Specifically, living body images are sequentially read out and displayed from the time code "t1". The preset frame rate may be a default frame rate, or may be a frame rate associated with living body images. The display here is assumed to be display on a monitor (not illustrated).

Further, the display 1022 obtains one "cross sectional image group ID", "D01" as an example here, from records (rows) corresponding to the subject ID "P10001" of cross section management information shown in FIG. 16, reads out cross sectional images in the order from the record indicating the same time code as the time code value "t1" corresponding the abovementioned firstly displayed living body image from records in which the subject ID of the cross section management information is "P10001" and the cross sectional image group ID is "D01", and sequentially displays them with the same frame rate as the living body images. One "cross sectional image group ID" may be determined in an arbitrary way. For example, it is possible to select the "cross sectional image group ID" with the smallest value in number part from among multiple "cross sectional image group ID", or use a "cross sectional image group ID" designated by the user. The display here is assumed to be display on a monitor (not illustrated).

When the display 1022 displays the cross sectional image of the cross sectional image group ID "D01" and corresponding time code value "t1", the display 1022 obtains, from the cross section management information shown in FIG. 17, the value of "blood vessel ID" associated with this "cross sectional image group ID" and this "time code". Here, "v01" and "v02" are obtained. Then, the display 1022 obtains all the "blood vessel ID", sequentially by "phase image group ID", from the record indicating the "time code" value "t1" and the "subject ID" "P10001" of phase blood vessel management information shown in FIG. 19, and judges whether or not the obtained "blood vessel ID" coincide with the "v01" and "v02" obtained in the above. This processing is repeated until detection of coincidence. Then, "phase image group ID" at the point of time when the coincidence is detected is obtained. Here, the record "F01" in which the "phase image group ID" is "F01", the "subject ID" is "P10001" and the "time code" is "2012/03/12_10:24:12.01" is obtained.

Next, the display 1022 obtains phase images with the "phase image group ID" "F01", from records of phase management information, sequentially in the order from the record of the "time code" "t1", and displays them with the same frame rate as the cross sectional images.

Accordingly, the living body images, the cross sectional images and the phase images are displayed in synchronous fashion.

Further, the display 1022 selects any one of the "blood vessel ID" "v01" and "v02" obtained for cross sectional images in the above. This selection may be determined in an arbitrary way, and here, for example, it is assumed that one with smaller number of the "blood vessel ID", specifically "v01", is selected. The display 1022: sequentially obtains the value of "time code" corresponding to cross sectional images to be displayed; obtains a period, wherein the center of the period is the obtained time code and the period is obtained by adding one second before and after the center; detects the record having "time code" indicating time within the obtained period from the records in which the value of the "subject ID" in the blood flow information management information shown in FIG. 21 is "P10001" and the value of the "blood vessel ID" is the "v01" determined above; obtains the combination of the values of "blood flow information" and "time code" included in the detected record; using this combination, generates, as a blood flow image, a graph in which a first axis (for example, a horizontal axis) shows time indicated by the "time code" and a second axis (for example, a vertical axis) shows flow velocity indicated by the "blood flow information"; and displays the blood flow image. The display here is display on a monitor (not illustrated). Further, here, an image expressed by a straight line that is perpendicular to the first axis is arranged at the position indicated by the "time code" associated with the cross sectional image to be displayed.

Figure 22:
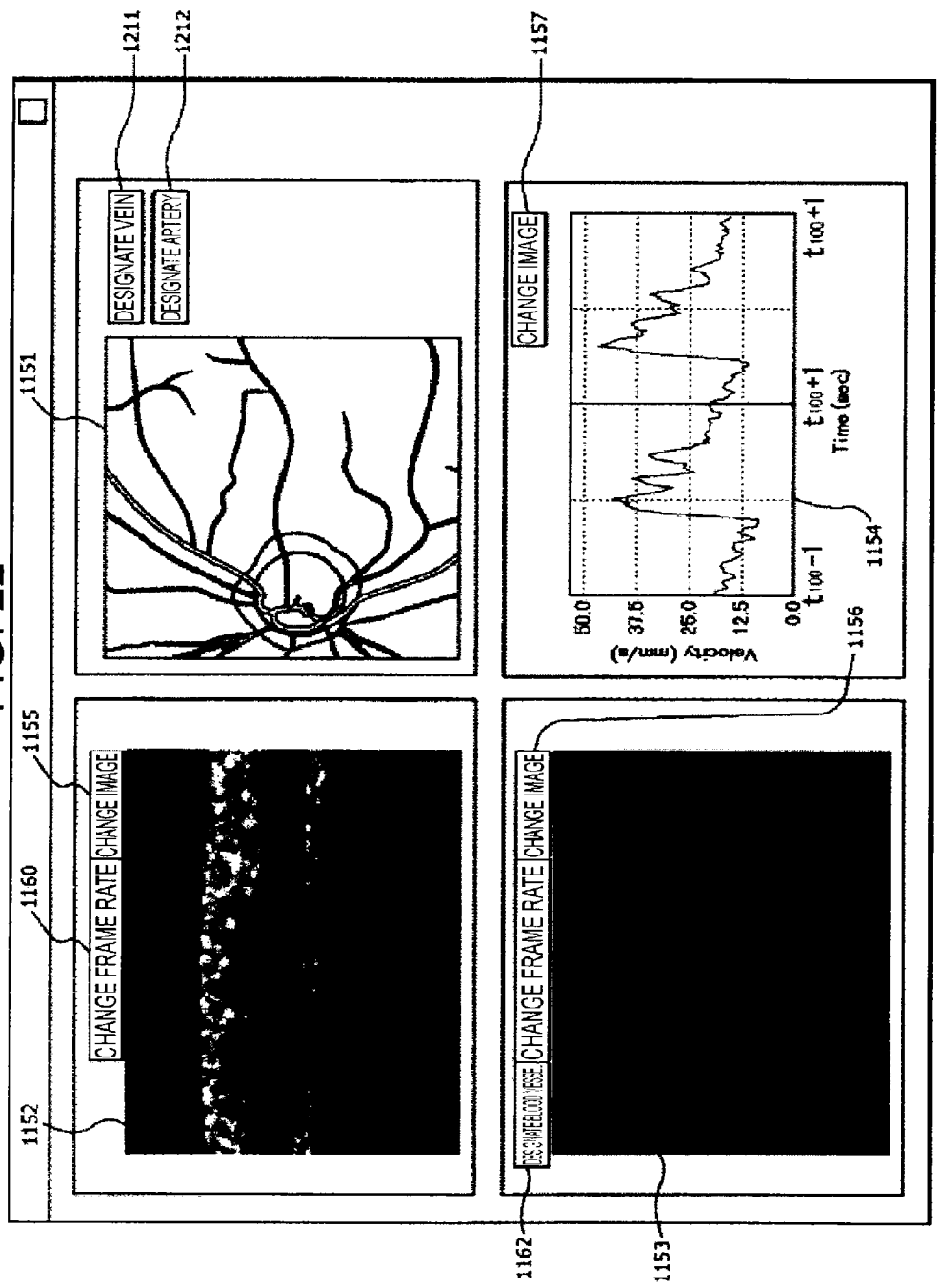
FIG. 22 is a diagram showing an example of display of the present embodiment.

FIG. 22 illustrates a display example of living body images, cross sectional images and phase images by the display 1022. Here, for convenience of explanation, a display example of images, instead of the timing immediately after the commencement of display, at the time "t100" that is the point of time when an arbitrary time has passed from the commencement of display. In the diagram, living body image 1151, cross sectional image 1152, phase image 1153 and blood flow image 1154 are arranged and displayed so as not to overlap each other in a screen.

Here, for example, when the user moves the pointer 1181 onto the image change button 1155 located adjacent to the cross sectional image 1152 and clicks it, the change operation receiving part 1018 obtains "blood vessel ID" other than "v01" and "v02" that are "blood vessel ID" corresponding to the displayed cross sectional image such as one obtained above from records in which the "subject ID" is "P10001" and the value of the "time code" coincides with the "time code" corresponding to the cross sectional image being displayed from among records of the cross section blood vessel management information shown in FIG. 17, and generates a list thereof. Here, applying so-called unique processing to overlapping ones, they are deleted except for one. Then, the generated list 1167 is displayed below the image change button 1155. It should be noted that information of this list may be previously obtained when displaying cross sectional images.

Figure 23:
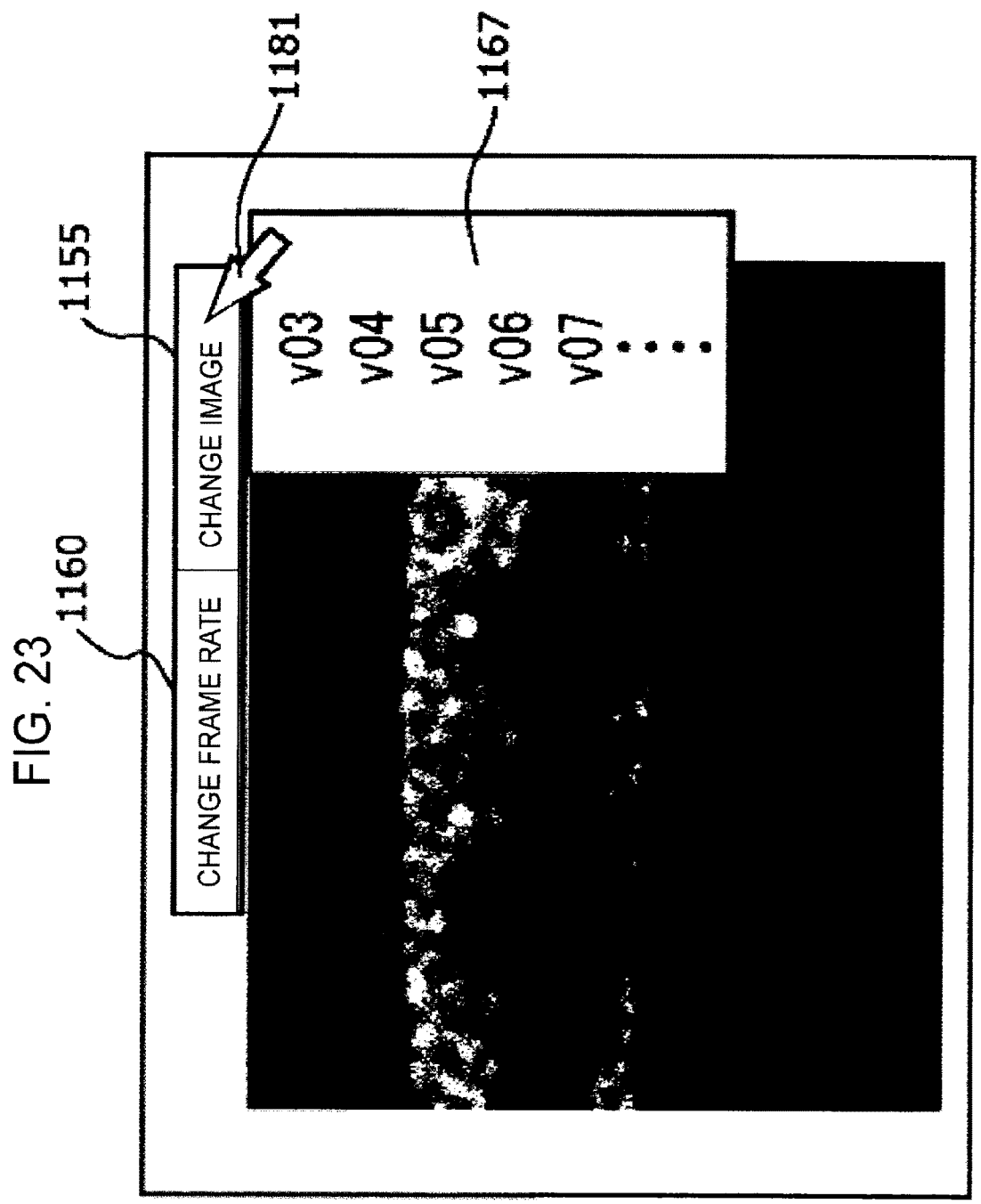
FIG. 23 is a diagram showing an example of display of the present embodiment.

FIG. 23 illustrates an example of the list of "blood vessel ID".

When the user selects "v03" from the list of FIG. 23 by manipulating a mouse etc., the change operation receiving part 1018 receives a change operation for changing a cross sectional image that is a target of display to the cross sectional image corresponding to the blood vessel ID "v03". The display 1022 changes display of cross sectional image in accordance with this change operation and carries out the same change as the change of cross sectional image to other phase images and blood flow images. That is, change of display is carried out so as to display the phase images and blood flow images corresponding to the blood vessel ID "v03".

Specifically, the display 1022 obtains the value of "cross sectional image group ID" from the record in which the value of the "time code" coincides with the value of the time code of the cross sectional image currently displayed and the "blood vessel ID" is "v03" from the cross section blood vessel management information. Then, the display 1022 reads out the "cross sectional image" associated with the obtained "cross sectional image group ID" and the value of the time code of the cross sectional image currently displayed from the cross section management information shown in FIG. 16, and displays it instead of the cross sectional image displayed immediately before. For example, the cross sectional image displayed immediately before is overwritten. Subsequently, the display 1022 sequentially displays cross sectional images in the same cross sectional image group associated with the time codes after the time code associated with this cross sectional image. It should be noted that instead of the time code of the cross sectional image currently displayed, the time code of the cross sectional image displayed next may be used.

Similarly for phase images, the display 1022 obtains the value of "phase image group ID" from the record in which the value of the "time code" coincides with the value of the time code of the phase image currently displayed and the "blood vessel ID" is "v03" from the phase blood vessel management information. Then, the display 1022 reads out the "phase image" associated with the obtained "phase image group ID" and the value of the time code of the phase image currently displayed from the phase management information shown in FIG. 19, and displays it instead of the phase image displayed immediately before. For example, the phase image displayed immediately before is overwritten. Subsequently, the display 1022 sequentially displays phase images in the same phase image group associated with the time codes after the time code associated with this phase image.

Further, relating blood flow images as well, the display 1022 obtains a combination of blood flow information associates with time code within a period including the value of the time code of the phase image currently displayed as above and the blood vessel ID "v03", generates a blood flow image, and displays it instead of the phase image displayed immediately before. Subsequently, the display 1022 sequentially obtains time codes corresponding to cross sectional images (or phase images) to be displayed, and sequentially obtains blood flow images using these time codes as above to display the blood flow images.

From this, cross sectional images in which a blood vessel of the blood vessel ID "v03" is expressed, phase images, and blood flow images related to this blood vessel are displayed on a monitor.

Figure 24:
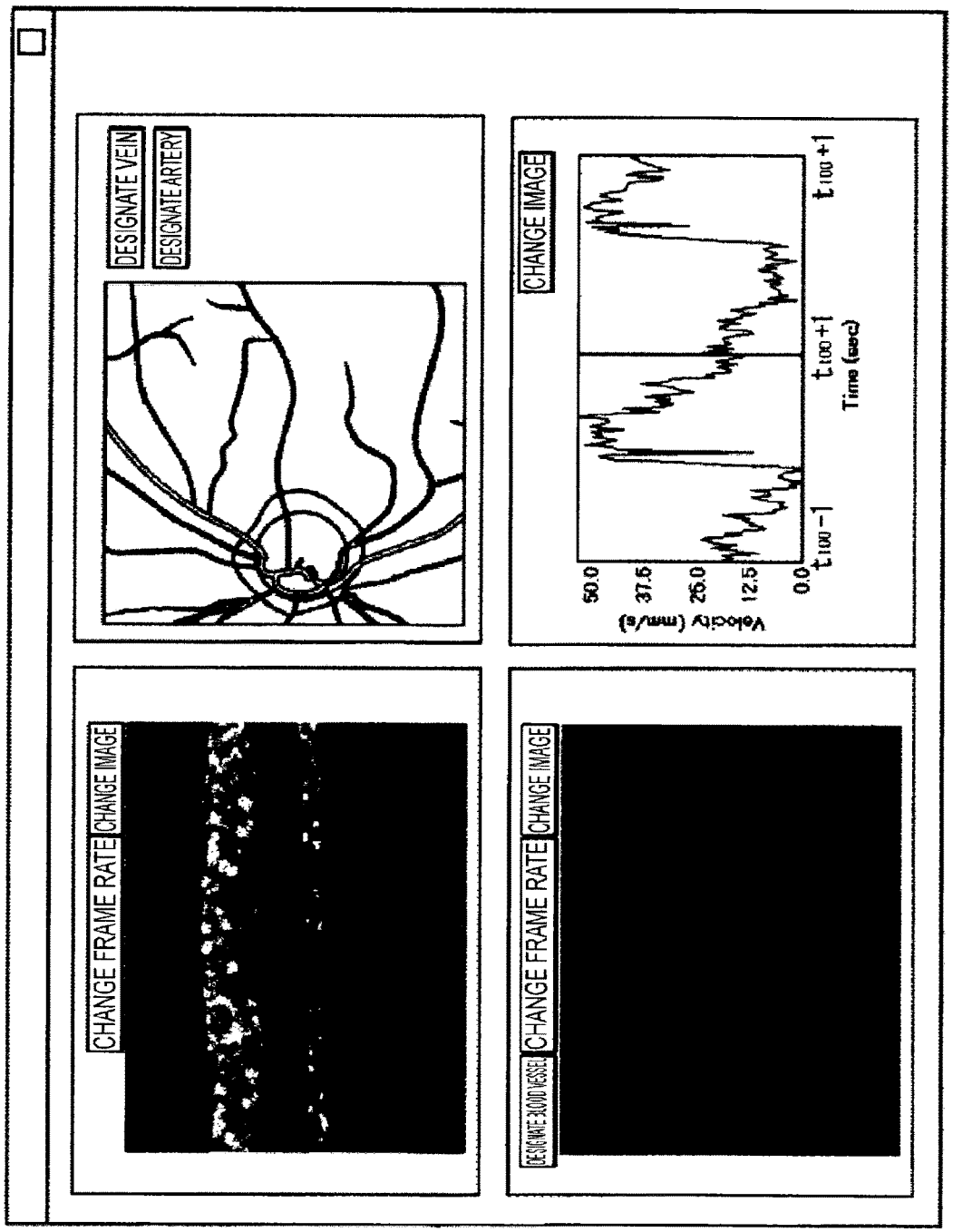
FIG. 24 is a diagram showing an example of display of the present embodiment.

FIG. 24 illustrates a display example of living body images, cross sectional images, phase images and blood flow images by the display 1022 after change of display. From this, it is possible to display images in which blood vessel corresponding to display content is changed in accordance with a change operation.

Further, similarly, in the case in which the image change button 1156 located adjacent to the phase image 1153 or the image change button 1157 located adjacent to the blood flow image 1153 is pushed, a list of the "blood vessel ID" other than the "blood vessel ID" associated with the respective images corresponding to the pushed button, and further when a "blood vessel ID" is selected, similar processing to the above can be executed so as to display phase image, cross sectional image and blood flow image corresponding to the selected "blood vessel ID".

Further, in the state illustrated in FIG. 22, it is assumed, for example, that the user moves the pointer 1181 to a location other than the line indicating the current time on the graph of the displayed blood flow image 1154, and carries out clicking.

Figure 25:
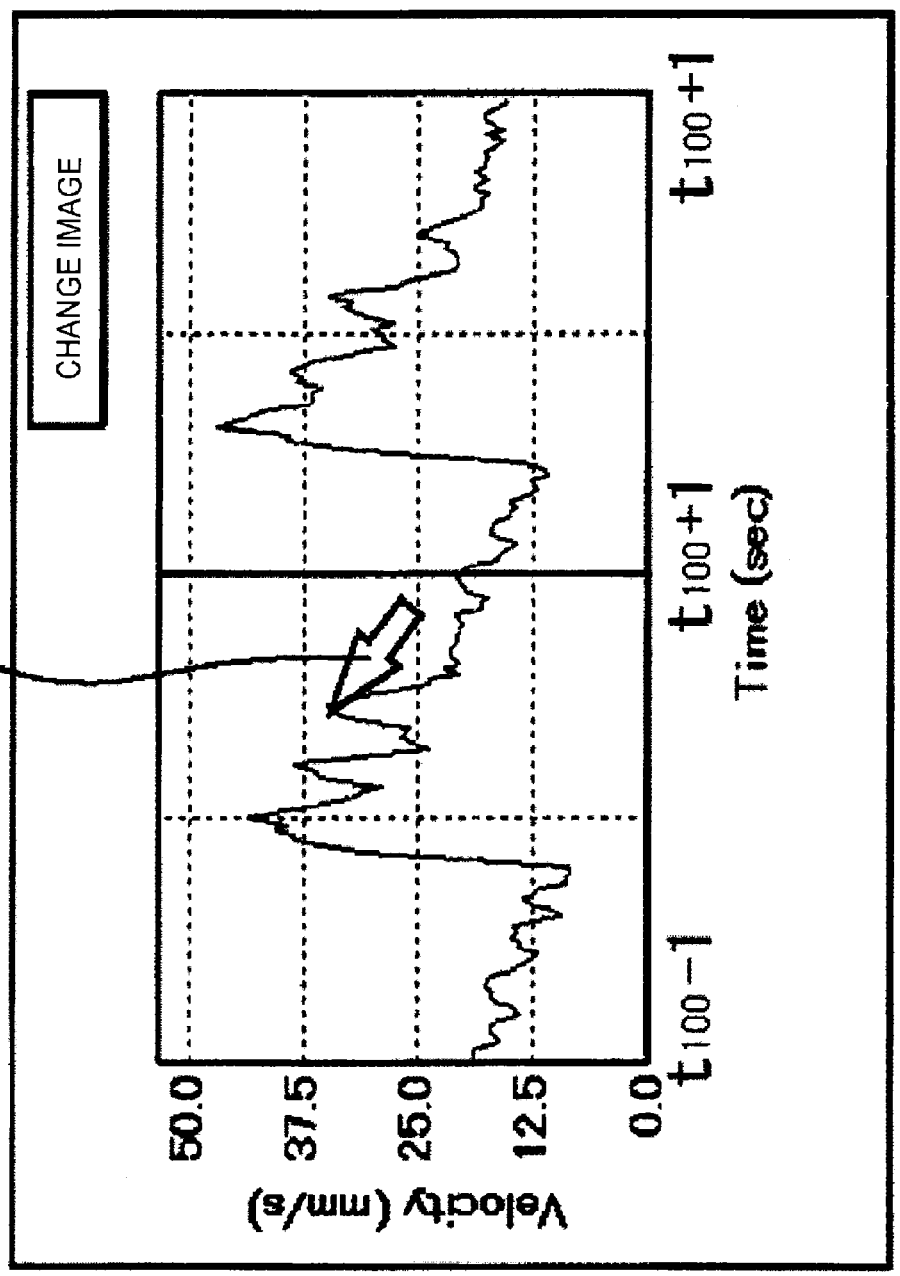
FIG. 25 is a diagram showing an example of display of the present embodiment.

FIG. 25 illustrates a state in which the blood flow image is clicked.

The change operation receiving part 1018 obtains the value of time (value of time code) corresponding to the clicked location from the time axis that is a first axis of the blood flow image 1154. For example, the obtained value of time is "t88". The change operation receiving part 1018 receives a change operation for changing the blood flow image being displayed to the blood flow image corresponding to the obtained time "t88". The display 1022 changes the display of blood flow image in accordance with this change operation, and carries out the same change, as the change executed to blood flow image, to other cross sectional images and phase images. That is, the change of display is executed so as to display the cross sectional image and phase image corresponding to the time "t88".

The display 1022: obtains a period, wherein the center of the period is the time "t88" obtained by the change operation receiving part 1018 and the period is obtained by adding one second before and after the center; detects the record having "time code" indicating time within the obtained period from the records in which the value of the "subject ID" in the blood flow information management information shown in FIG. 21 is "P10001" and the value of the "blood vessel ID" is the value "v01" corresponding to the blood vessel information that is a target currently displayed; generates a blood flow image from the combination of the values of "blood flow information" and "time code" included in the detected record in the same way as above; and displays the blood flow image.

Further, the display 1022: displays cross sectional image included in the record (row) in which the value of the "subject ID" coincides with "P10001", the value of the "cross sectional image group ID" coincides with "D01" that is the value of the "cross sectional image group ID" corresponding to the cross sectional image that is a display target, and the value of the "time code" coincides with the time "t88" obtained by the change operation receiving part 1018 from the cross section management information shown in FIG. 16; and displays the cross sectional images included in the cross sectional image group whose value of the "cross sectional image group ID" is "D01" sequentially in the order according to the time codes.

Further, the display 1022: displays phase image included in the record (row) in which the value of the "subject ID" coincides with "P10001", the value of the "phase image group ID" coincides with "F01" that is the value of the "phase image group ID" corresponding to the phase image that is a display target, and the value of the "time code" coincides with the time "t88" obtained by the change operation receiving part 1018 from the phase management information shown in FIG. 19; and displays the phase images included in the phase image group whose value of the "phase image group ID" is "F01" sequentially in the order according to the time codes.

Further, the display 1022: displays living body image included in the record (row) in which the value of the "subject ID" coincides with "P10001", the value of the "living body image group ID" coincides with "E01" that is the value of the "living body image group ID" corresponding to the living body image that is a display target, and the value of the "time code" coincides with the time "t88" obtained by the change operation receiving part 1018 from the living body management information shown in FIG. 13; and displays the living body images included in the living body image group whose value of the "living body image group ID" is "E01" sequentially in the order according to the time codes.

It is possible to display living body images, cross sectional images, phase images and blood flow images according to the time indicated by the change operation by executing the change operation for changing time to blood flow image in this way.

It should be noted that when an operation for changing time of image displayed is carried out to cross sectional images or phase images as well, the same processing as above is executed by obtaining the time an accordance with this change information. It should be noted that the operation for changing time to cross sectional images or phase images may be received by a slider bar (illustration omitted) indicating reproduction time of a moving image, for example.

Next, a case is described in which the user moves the pointer 1081 onto one blood vessel in the displayed living body image 151 and performs clicking in the state illustrated in FIG. 22. The change operation receiving part 1018 receives a blood vessel designating operation for designating a location on a blood vessel. This blood vessel designating operation is an operation for designating a blood vessel including the clicked location.

Figure 26:
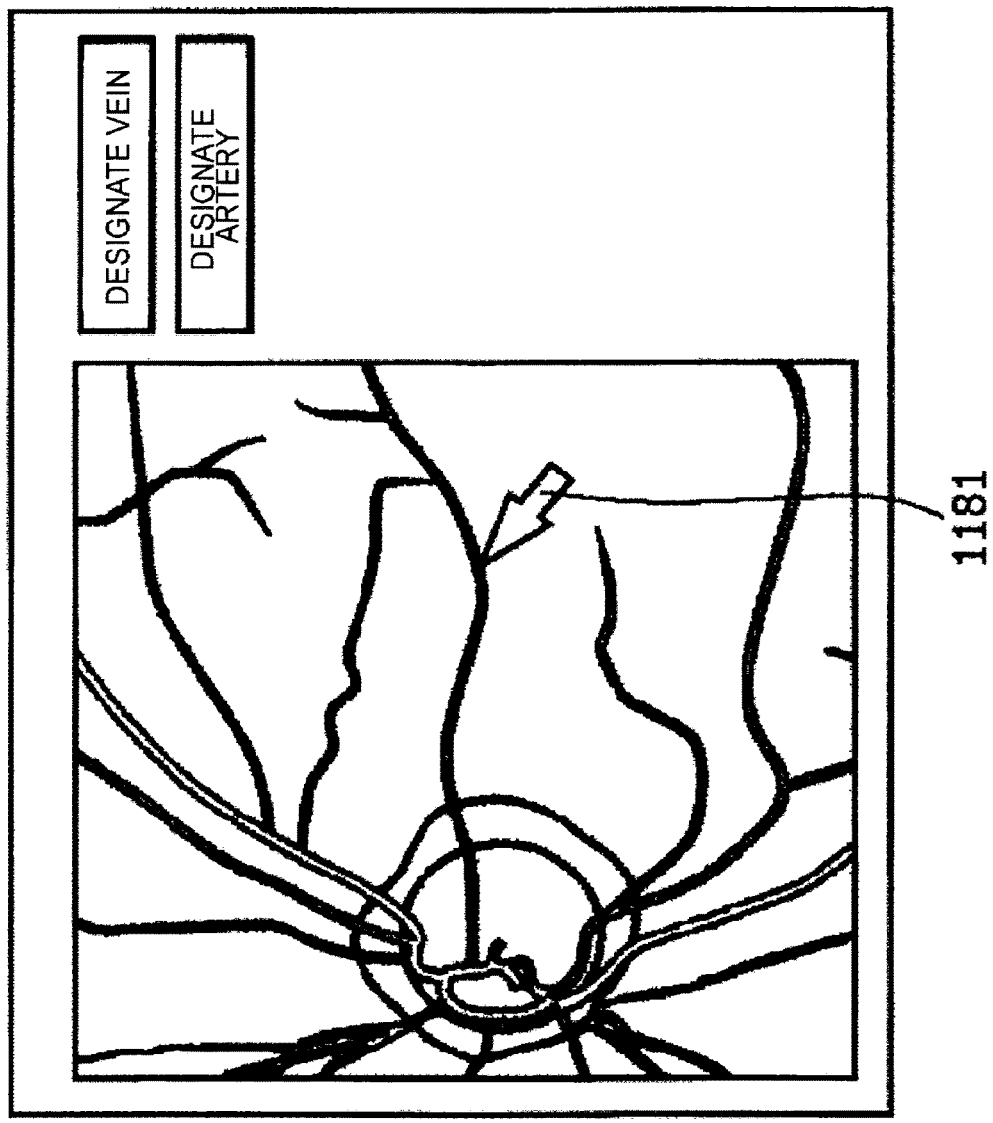
FIG. 26 is a diagram showing an example of display of the present embodiment.

FIG. 26 illustrates a state in which the living body image is clicked.

Once receiving a blood vessel designating operation, the change operation receiving part 1018 obtains the coordinate of the designated location (clicked location). For example, the obtained coordinate is (x33, y33). The change operation receiving part 1018 detects the record having the coordinate that coincides with the above obtained coordinate (x33, y33) within one or more coordinates indicated by the "blood vessel location information" from among the records (rows) in which the value of the "subject ID" coincides with "P10001" and the value of the "time code" coincides with the value "t100" corresponding to the living body image being displayed in the blood vessel management information illustrated in FIG. 14. Then, the value of the "blood vessel ID" of the detected record is obtained as blood vessel identification information corresponding to the location indicated by the blood vessel designating operation. Here, the obtained value of the "blood vessel ID" is assumed to be "v03", for example.

The display 1022 displays cross sectional images and phase images corresponding to the blood vessel ID "v03", that is, cross sectional images and phase images including the blood vessel indicated by the blood vessel ID "v03" by carrying out the same processing as the case of selecting the blood vessel ID "v03" from the list illustrated in FIG. 23 as described above. Further, similar to the above, the display 1022 displays blood flow images corresponding to the blood vessel ID "v03", that is, blood flow images that are created using blood flow information related to the blood vessel indicated by the blood vessel ID "v03". The images thus displayed are similar to those in FIG. 24.

Accordingly, it is possible to display, using the display 1022, cross sectional images, phase images and blood flow images corresponding to the blood vessel designated on living body images by the user. In this case, it is enough to designate a blood vessel and it is not required to designate the site in which cross sectional images are acquired, so there is no need to search the site in which cross sectional images are acquired for a blood vessel that the user wants to observe, and it is possible to display cross sectional images etc. related to a blood vessel arbitrarily designated for observing cross sectional images, therefore, labors are not required for searching the site in which cross sectional images are imaged, and easy and intuitive operation becomes possible.

Next, a case is described in which the user performs an operation for changing frame rates of cross sectional images and phase images that are display targets in the state illustrated in FIG. 22, for example. For example, it is assumed that the frame rate change button 1160 of the cross sectional image 1152 is clicked by using mouse etc. to input "15" fps (frame per second) etc. as a value of frame rate after the change. The change operation receiving part 1018 receives the frame rate changing operation for changing the frame rate to "15" fps as the frame rate changing operation in accordance with this operation.

The display 1022 changes the frame rate of displaying cross sectional images from the current frame rate to "15" fps. Further, the frame rates of phase images and living body images are also changed to the same frame rate. Then, cross sectional images, phase images and living body images are sequentially displayed with the changed frame rate.

The same applies to the case in which a frame rate changing operation is performed for changing the frame rate of phase images.

From this, when a frame rate changing operation is performed to any one of cross sectional image and phase image, the frame rate of the image that is not the target of the change operation between the cross sectional image and phase image may be changed.

When the user selects, for example, a blood vessel designating button for carrying out an operation for designating a blood vessel in phase images in the state illustrated in FIG. 22 and clicks a region on one blood vessel in the phase image 1153 using a mouse, the change operation receiving part 1018 receives this phase blood vessel designating operation for designating the location of a blood vessel in phase image. The phase blood vessel designating operation is an operation for designating the blood vessel including the clicked location.

Upon receiving the phase blood vessel designating operation, the change operation receiving part 1018 obtains the coordinate of the designated location (clicked location). Suppose that the obtained coordinate is (x122, y122), for example. The change operation receiving part 1018 detects the record having the coordinate that coincides with the above obtained coordinate (x122, y122) within one or more coordinates indicated by the "blood vessel location information" from among the records (rows) in which the value of the "subject ID" coincides with "P10001" and the value of the "time code" coincides with the value "t100" corresponding to the living body image being displayed in the phase blood vessel management information illustrated in FIG. 20. Then, the value of the "blood vessel ID" of the detected record is obtained as blood vessel identification information corresponding to the location designated by the phase blood vessel designating operation. Here, the obtained value of the "blood vessel ID" is assumed to be "v02", for example.

The display 1022 detects the record in which the values of the "cross sectional image group ID" and "time code" respectively coincide with the "cross sectional image group ID" and "time code" corresponding to the cross sectional image being displayed and the value of the "blood vessel ID" is the value "v02" obtained above from the records of the phase blood vessel management information illustrated in FIG. 20, and obtains the value of the "phase blood vessel location information" of the detected record. Then, the display 1022 overlays a preset color over the region in the cross sectional image being displayed indicated by this "phase blood vessel location information", thereby assigning the preset color to this region in the cross sectional image. This color is preferably different from those of other regions in the cross sectional image. Then, the display 1022 displays, instead of the cross sectional image being displayed, a cross sectional image in which the color thus preset is overlaid over the region indicated by the "phase blood vessel location information". For example, the cross sectional image displayed immediately before is overwritten by the overlaid cross sectional image.

Figure 27:
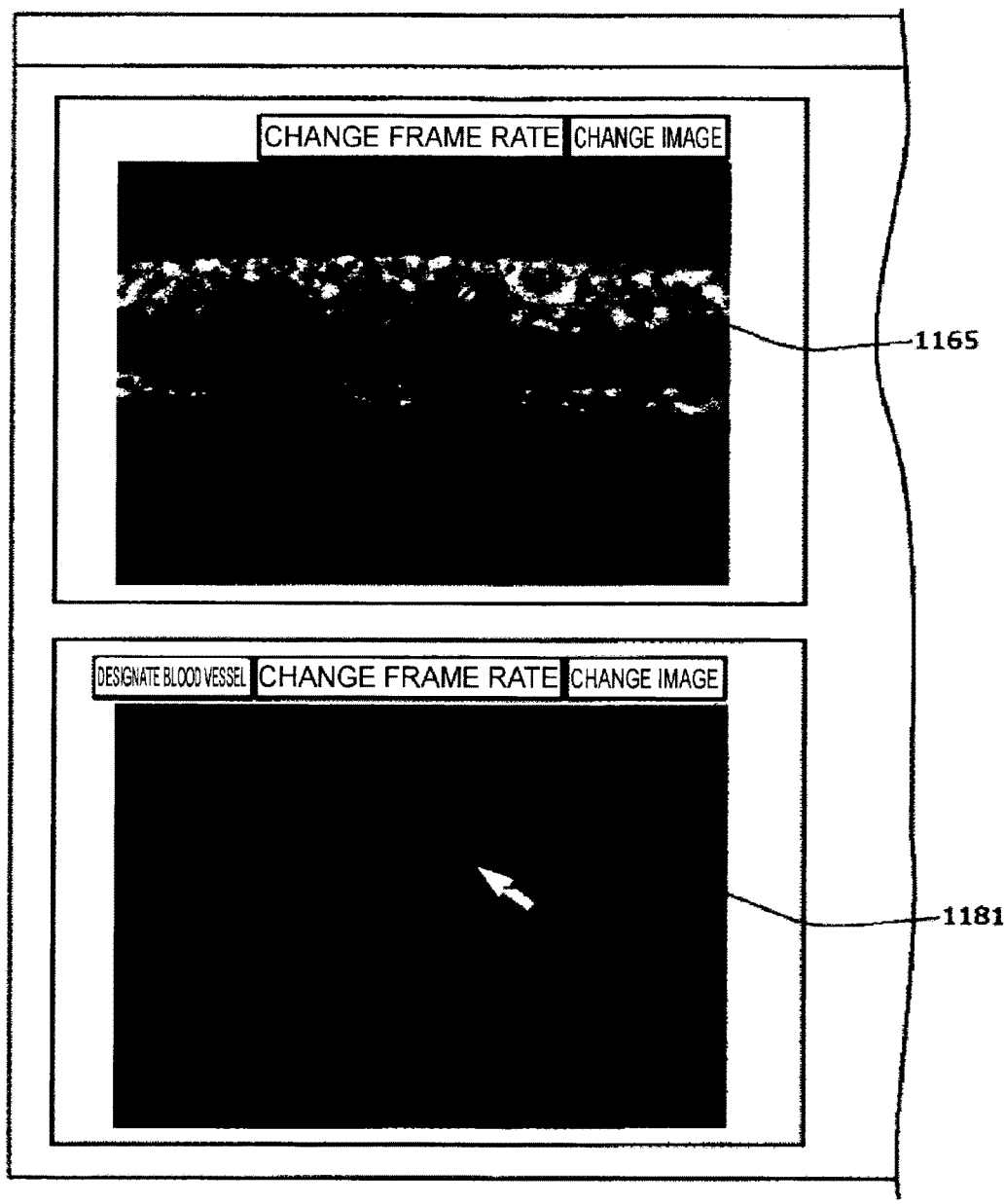
FIG. 27 is a diagram showing an example of display of the present embodiment.

FIG. 27 illustrates a state in which blood vessel region in a cross sectional image corresponding to the phase blood vessel designating operation is displayed in a different aspect from other regions. In this diagram, the shaded region 1165 is supposed to be a site overlaid. From this, when a blood vessel in a phase image is designated by a mouse etc., the location in a cross sectional image corresponding to this blood vessel may be easily understandably displayed in a different aspect from others.

Further, when the change operation receiving part 1018 receives the phase blood vessel designating operation and obtains the blood vessel ID "v02" in the same way as above, the display 1022: detects one or more records in which the value of the "blood flow image group ID" is the "blood flow image group ID" corresponding to the blood flow image being displayed, the value of the "time code" is a value within the same period as the period in which blood flow information corresponding to the blood flow image being displayed is obtained, and the "blood vessel ID" is the value "v02" from the records of the blood flow information management information illustrated in FIG. 21; obtains a combination of the value of the "blood flow information" included in the detected one or more records and the value of the "time code"; obtains a blood flow image using this combination; and display the obtained blood flow image by replacing the blood flow image being displayed (for example, overwriting it). Accordingly, a blood flow image related to the blood vessel designated in the phase image is displayed.

Further, for example, a case is described in which the user carries out an operation for superposing and displaying cross sectional images and phase images using a menu (not illustrated) etc. in the state illustrated in FIG. 22. The change operation receiving part 1018 receives an operation for superposing and displaying cross sectional images and phase images. Then, the display 1022 superposes and displays cross sectional images and phase images that are displayed after the operation. When superposing and displaying them, the superposition is carried out in a way in which the respective contents of the phase images and cross sectional images are simultaneously recognizable by visual sensation etc. Specifically, the display 1022 at least superposes one image over the other image, wherein the transmittance of the one image is adjusted to become transparent. Alternatively, it is possible to superpose imaged as overlay display, or superpose images using composition mode such as multiplication mode in which the under image may be recognizable. Since phase images and cross sectional images to be superposed are displayed synchronously as above, the phase images and cross sectional images in the superposed images are also synchronized.

Figure 28:
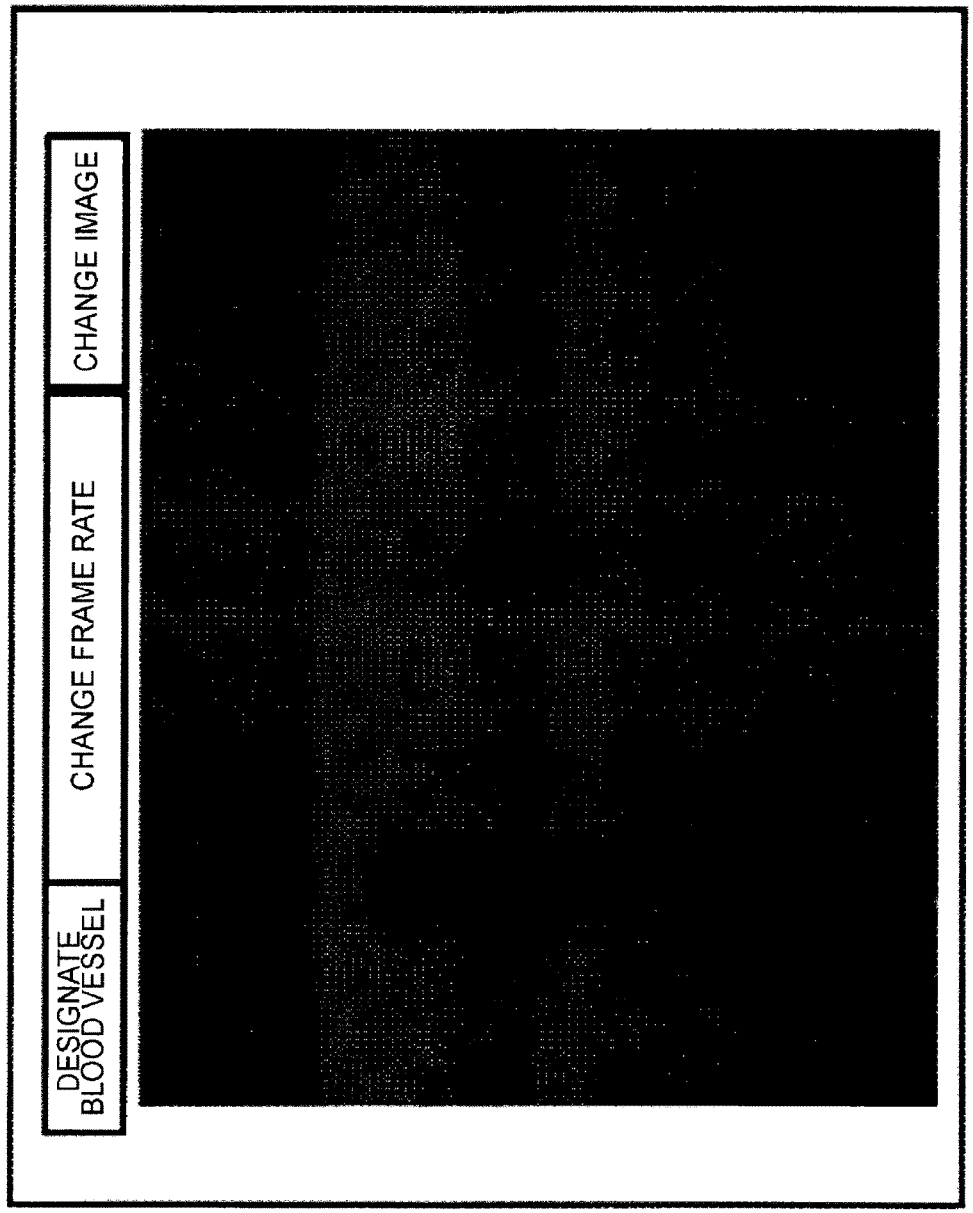
FIG. 28 is a diagram showing an example of display of the present embodiment.

FIG. 28 illustrates a state in which phase images and cross sectional images are superposed and displayed.

Further, in the case in which, as above, phase images and cross sectional images are superposed and the change operation receiving part 1018 receives a change operation to any one of this superposed image and blood flow images, the display 1022 carries out change corresponding to the change operation of the blood flow images that have been a target of the change operation, and further, carries out the same change as the change corresponding to the change operation to the images that have not been the target of the change operation as well.

For example, when the change operation receiving part 1018 receives a change operation for changing time of blood flow images in the same way as above, the display 1022, regarding the blood flow images, obtains blood flow information and time codes within a period in which the center thereof is the time obtained in accordance with the change operation in the same way as above, and obtains and displays a blood flow images. Further, regarding superposition of images, the display 1022 may obtain cross sectional images and phase images corresponding to the time obtained in accordance with the change operation in the same way as above, and displays the superposed images. Further, this also applies to the case in which a change operation for changing time of the superposed images is received. That is, it may be configured to obtain phase images, cross sectional images and blood flow images changed in accordance with the change operation, and display superposed images for the phase images and cross sectional images. Here, it is possible to carry out the change operation in this case by considering that it is a change operation to one of the images superposed, or by considering that it is a change operation to the both.

Further, the same also applies to the case of performing a change operation to blood flow images for changing blood vessel that is a target of graph display, and the case of performing a change operation to superposed images for changing blood vessel displayed in the images. That is, it may be configured to obtain phase images, cross sectional images and blood flow images changed in accordance with the change operation, and display superposed images for the phase images and cross sectional images.

Further, it may be configured that a frame rate change operation to any one of cross sectional images and phase images superposed and displayed is received, and that upon receiving the frame rate change operation, the respective frame rates of the cross sectional images and phase images to be superposed and displayed are changed to the frame rate corresponding to the frame rate change operation (for example, the frame rate designated by the frame rate change operation).

Further, for example, it is assumed that the user performs an operation for designating a region on a vein among blood vessels in the living body image (fundus image) 1151 by pushing the button 1211 for performing an operation for designating a vein. For example, it is assumed that one point on a region on a blood vessel that is a vein is clicked using a mouse. The state in which clicking is being carried out is the same as in the FIG. 26 except for the fact that the button 1211 is being pushed.

The blood vessel classification designating operation receiving part 1019 receives a blood vessel classification designating operation for designating, as a vein, the blood vessel corresponding to the region indicated by the blood vessel location information including the clicked coordinate. It is assumed, for example, that the clicked coordinate is (x13, y13). The blood vessel classification management information accumulating part 1021 detects the record having the coordinate that coincides with the coordinate (x13, y13) corresponding to the blood vessel classification designating operation received by the blood vessel classification designating operation receiving part 1019 within the values of the "blood vessel location information" from among the records (rows) in which the value of the "subject ID" coincides with "P10001", the "living body image group ID" coincides with "E01", and the value of the "time code" coincides with the value "t100" corresponding to the living body image being displayed in the blood vessel management information illustrated in FIG. 14. Then, the blood vessel classification management information accumulating part 1021 obtains the value of the "blood vessel ID" of the detected record as a "blood vessel ID" indicating the blood vessel that is a vein. Here, for example, it is assumed that "vo1" is obtained as the "blood vessel ID" indicating the blood vessel that is a vein. The blood vessel classification management information accumulating part 1021 accumulates blood vessel classification management information including the obtained "blood vessel ID", blood vessel classification information indicating that it is a vein, and the subject ID "P10001" in the blood vessel classification management information storage 1020.

Next, when the user selects the button 1212 etc. for performing an operation for designating an artery and clicks, using a mouse, one point in a region on an artery among blood vessels in the living body image 1151, the blood vessel classification designating operation receiving part 1019 receives a blood vessel classification designating operation for designating, as an artery, the blood vessel corresponding to the region indicated by the blood vessel location information including the clicked coordinate. It is assumed, for example, that the clicked coordinate is (x22, y22). The blood vessel classification management information accumulating part 1021 detects the record having the coordinate that coincides with the coordinate (x22, y22) corresponding to the blood vessel classification designating operation received by the blood vessel classification designating operation receiving part 1019 within the values of the "blood vessel location information" from among the records (rows) in which the value of the "subject ID" coincides with "P10001" and the value of the "time code" coincides with the value "t100" corresponding to the living body image currently displayed in the blood vessel management information illustrated in FIG. 14. Then, the blood vessel classification management information accumulating part 1021 obtains the value of the "blood vessel ID" of the detected record as a "blood vessel ID" indicating the blood vessel that is an artery. Here, for example, it is assumed that "vo1" is obtained as the "blood vessel ID" indicating the blood vessel that is an artery. The blood vessel classification management information accumulating part 1021 accumulates blood vessel classification management information including the obtained "blood vessel ID", blood vessel classification information indicating that it is an artery, and the subject ID "P10001" in the blood vessel classification management information storage 1020.

FIG. 29 illustrates an example of blood vessel classification management information stored in the blood vessel classification management information storage 1020. Here, as an example, a case is illustrated in which other blood vessel classification management information is already stored in the blood vessel classification management information storage 1020. The blood vessel classification management information includes "subject ID", "blood vessel ID" and "blood vessel classification information". The "blood vessel classification information" is blood vessel classification information, and here, it is supposed that the value is "artery" when a blood vessel is a vein and the value is "vain" when a blood vessel is an artery.

Next, suppose that the user manipulates a menu (illustration omitted) etc. to carry out an operation for reflecting blood vessel classification information stored in the blood vessel classification management information storage 1020 to the phase images currently displayed. When this operation is received by the change operation receiving part 1018, the display 1022 reads out the value of the "blood vessel ID" corresponding to the cross sectional images currently displayed from the phase blood vessel management information illustrated in FIG. 20. Specifically, the display 1022: reads out values "v01" and "v02" of the "blood vessel ID" of the record in which the value of the "subject ID" coincides with "P10001", the value of the "cross sectional image group ID" coincides with "F01" and the value of the "time code" coincides with the value "t100" corresponding to the living body image currently displayed; detects the record in which the value of the "blood vessel ID" coincides with any of these in the blood vessel classification management information illustrated in FIG. 29; and obtains a combination of the value of the "blood vessel classification information" and the value of the "blood vessel ID" in the detected record. Here, it is assumed that a first combination of the blood vessel ID "v01" and blood vessel classification information "vein" and a second combination of the blood vessel ID "v02" and blood vessel classification information "artery" are obtained.

The display 1022 detects the record in which the value of the "blood vessel ID" coincides with "v01" that is the value of the "blood vessel ID" of the first combination obtained as above among the records corresponding to the phase image currently displayed in the phase blood vessel management information illustrated in FIG. 20, and obtains the value of the "phase blood vessel location information" of the detected record. Then, the display 1022 changes display aspect of the region in the phase image currently displayed indicated by this "phase blood vessel location information" (that is, the region on the blood vessel indicated by the blood vessel ID "v01") to the display aspect previously associated with "vein" that is the value of the "blood vessel classification information" of the first combination obtained in the above. For example, a preset color is overlaid on this region.

The display 1022 detects the record in which the value of the "blood vessel ID" coincides with "v02" that is the value of the "blood vessel ID" of the second combination obtained as above among the records corresponding to the phase image currently displayed in the phase blood vessel management information illustrated in FIG. 20, and obtains the value of the "phase blood vessel location information" of the detected record. Then, the display 1022 changes display aspect of the region in the phase image currently displayed indicated by this "phase blood vessel location information" (that is, the region on the blood vessel indicated by the blood vessel ID "v02") to the display aspect previously associated with "artery" that is the value of the "blood vessel classification information" of the second combination obtained in the above. For example, a preset color is overlaid on this region. Here, information designating display aspects is accumulated in a recording medium (not illustrated) in association with each blood vessel classification information such that the display aspects of the blood vessel classification information "vein" and blood vessel classification information "artery" become distinguishable. For example, information associating the blood vessel classification information "vein" with overlaying color "red" and information associating the blood vessel classification information "artery" with overlaying color "blue" are accumulated in advance. Then, the display 1022 uses these information to overlay blue on the region corresponding to the above blood vessel ID "v01" and overlay red on the region corresponding to the above blood vessel ID "v02".

Figure 30:
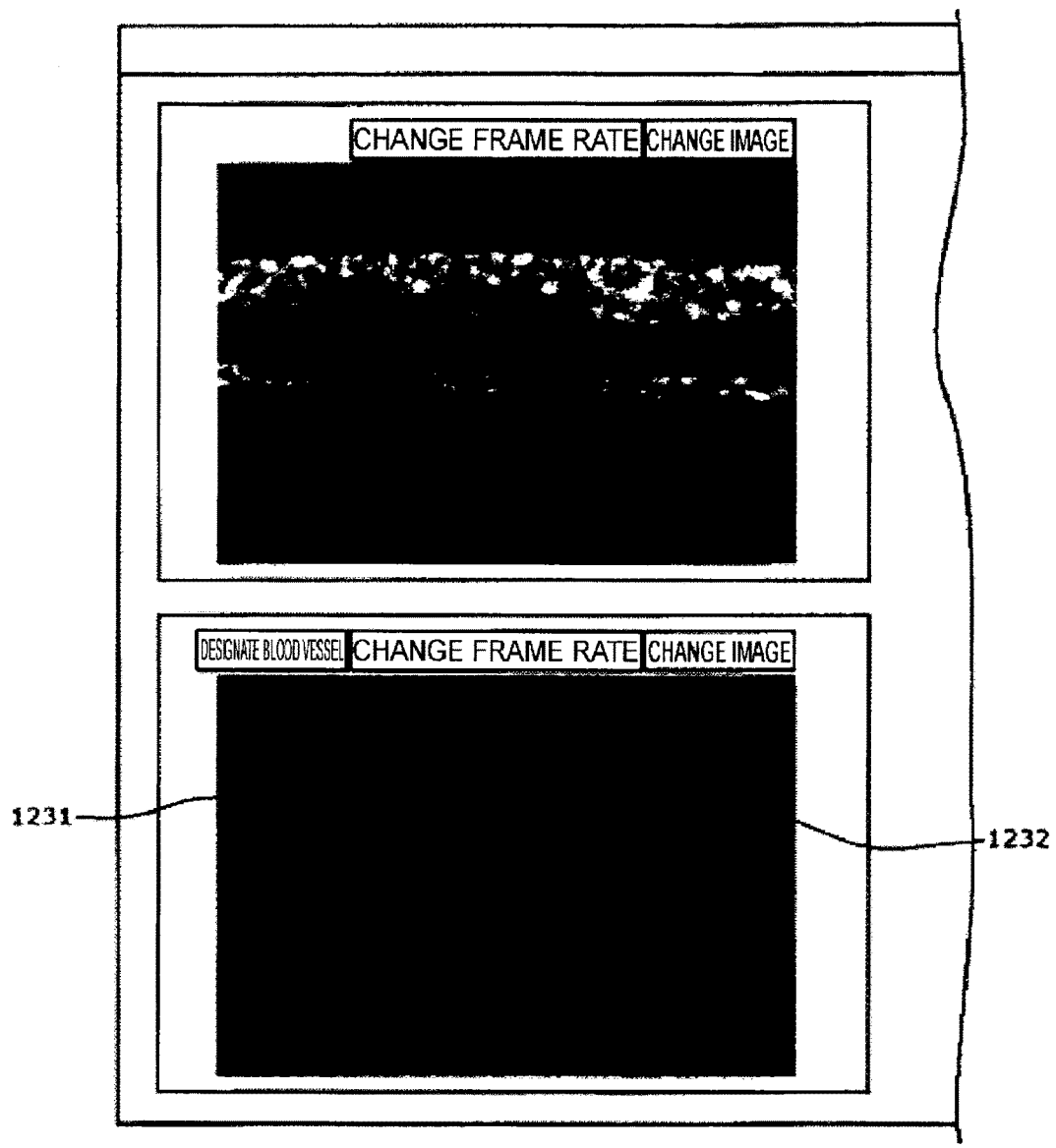
FIG. 30 is a diagram showing an example of display of the present embodiment.

FIG. 30 illustrates an example of the case in which blood vessel classification management information is reflected to phase images and such phase images are displayed. In the diagram, the region 1231 is a region corresponding to the above blood vessel ID "v01", and the region 1232 is a region corresponding to the above blood vessel ID "v02". From such display, it becomes possible to clearly express vein portions and artery portions of phase images. Further, designation of vain/artery may be carried out from living body images such as fundus images, thereby judgment is easy and operability is outstanding.

It should be noted that a case in which blood vessel classification management information is reflected to phase images is described; however, blood vessel classification management information may be reflected to cross sectional images. In this case, information utilized for phase images may be replaced by information corresponding to cross sectional images.

Further, blood vessel classification management information is reflected to phase images according to operations of the user in this example; however, it may be configured to reflect blood vessel classification management information to phase images as default, and in response to every reception of blood vessel classification designating operation, change the display of phase images including corresponding blood vessel.

It should be noted that in this specific example, a case is described in which cross sectional images and phase images in which blood vessel identification information associated with the same time as cross sectional images and phase images being displayed are different when displaying cross sectional images and phase images in which blood vessel identification information are different; however, it may be configured to display cross sectional images and phase images in which blood vessel identification information corresponding to the time associated with cross sectional images and phase images displayed immediately after the cross sectional images and phase images being displayed. This is the same in the case of displaying cross sectional images and phase images in which regions on blood vessels in the cross sectional images and phase images are displayed in a different aspect from other regions, for example.

According to the present embodiment as above, when the display 1022 displays cross sectional images, phase images and blood flow images acquired for the same site in the living body, and when a change operation for changing the display of any one of the cross sectional images, phase images and blood flow images, change of display according to the change operation is carried out for the target image of the change operation and the same change as the change operation corresponding to this change operation for other images, thereby being capable of establishing correspondence among the multiple images even when the change operation is carried out, and therefore, change of display can be executed appropriately for the multiple images acquired for the same site in the living body.

Further, since cross sectional images and phase images acquired for the same site in the living body are superposed and displayed, it becomes possible to compare corresponding sites in the cross sectional images and phase images exceedingly accurately and easily.

Further, upon designating whether a blood vessel in living body images is a vein or an artery, this designation is reflected as the display aspect of a region in phase images in which the blood vessel is displayed; therefore, individual designation for classifying blood vessel to the respective images, and so operation may be simplified.

It should be noted that in the present embodiment, as in the case in which phase images are created using the same information as information utilized for acquiring cross sectional images or blood flow images, cases are described in which correspondence between phase images and cross sectional images is established; however, when correspondence between phase images and cross sectional images is not established, the display may be configured to change image size of at least one of phase images and cross sectional images such that the region indicated by the phase blood vessel location information respectively corresponding to phase images and cross sectional images to be superposed and the region indicated by the cross sectional blood vessel location information are overlapped with each other in the same height or width, and superpose these images.

Further, in each of the above embodiments, each processing may be realized by centralized processing of a single apparatus (system), or alternatively, may be realized by distributed processing of multiple apparatus.

Further, needless to say, two or more communication means (information transmitter etc.) existed in one apparatus may be realized by one medium physically in each of the above embodiments.

Further, cases in which an image displaying apparatus is standalone are described in each of the above embodiments; however, an image displaying apparatus may be a standalone apparatus or may be a server apparatus in a server/client system. In the latter case, the display and/or receiving part receive inputs via a communication line and display a screen.

It should be noted that software that realizes an image displaying apparatus is a program described below. That is, this program is a program configured to cause a computer that is accessible to: a cross sectional image storage configured to store a cross sectional image group including multiple cross sectional images each of which is associated with time and expresses a cross section intersecting at least one blood vessel of a living body; a phase image storage configured to store a phase image group including multiple phase images each of which is associated with time and expresses chronological variation of phase difference at a cross section intersecting at least one blood vessel of the living body; and a blood flow information storage configured to store a blood flow information group including multiple blood flow information each of which is related to blood flow in a blood vessel of the living body and is associated with time, to function as: a display configured to synchronously display a cross sectional image included in the cross sectional image group and a phase image included in the phase image group using time associated with the cross sectional image and the phase image, and display a blood flow image that expresses multiple blood flow information, from among the blood flow information included in the blood flow information group, associated with time within a period including time associated with the cross sectional image and the phase image that are being displayed; and a change operation receiving part configured to receive a change operation for changing display of one of the cross sectional image, the phase image and the blood flow image that are displayed by the display, wherein the display performs the same change as the change corresponding to the change operation to the cross sectional image, the phase image and the blood flow image that are displayed by the display.

Further, this program is a program configured to cause a computer that is accessible to: a cross sectional image storage configured to store a cross sectional image group including multiple cross sectional images each of which is associated with time and expresses a cross section intersecting at least one blood vessel of a living body; and a phase image storage configured to store a phase image group including multiple phase images each of which is associated with time and expresses chronological variation of phase difference at a cross section intersecting at least one blood vessel of the living body, to function as: a display configured to synchronously and superposedly display a cross sectional image included in the cross sectional image group and a phase image included in the phase image group using time associated with the cross sectional image and the phase image.

Further, this program is a program configured to cause a computer that is accessible to: a living body image storage configured to store a living body image acquired by photographing a living body; a blood vessel management information storage configured to store blood vessel management information including blood vessel location information that expresses location of at least one blood vessel in the living body image and blood vessel identification information corresponding to this blood vessel; a phase image storage configured to store phase management information that includes a phase image group including multiple phase images each of which is associated with time and expresses chronological variation of phase difference at a cross section intersecting at least one blood vessel of the living body and blood vessel identification information of a blood vessel intersecting a cross section corresponding to the phase image group; a phase blood vessel management information storage configured to store phase blood vessel management information including phase blood vessel location information that expresses location of a blood vessel in the phase image and blood vessel identification information of this blood vessel; and a blood vessel classification management information storage configured to store blood vessel classification management information including blood vessel identification information and blood vessel classification information that expresses whether a blood vessel is a vein or an artery, to function as: a display configured to display the living body image and a phase image included in the phase image group that is associated with one blood vessel identification information; a blood vessel classification designating operation receiving part configured to receive blood vessel classification designating operation for designating location of a vein or an artery in the living body image displayed by the display; and a blood vessel classification management information accumulating part configured to obtain blood vessel identification information corresponding to the location designated by the blood vessel designating operation from the blood vessel management information, and accumulate, in the blood vessel classification management information storage, blood vessel classification management information including this blood vessel identification information and the blood vessel classification information that expresses whether the blood vessel designated by the blood vessel designating operation is a vein or an artery, wherein the display obtains the blood vessel identification information and the phase blood vessel location information corresponding to the phase image displayed by the display from the phase blood vessel management information, obtains the blood vessel classification information corresponding to this blood vessel identification information from the blood vessel classification management information, and displays the location expressed by the phase blood vessel location information corresponding to the blood vessel identification information of the phase image in a different display aspect from other locations, wherein the display aspect thereof depends on whether the blood vessel classification information corresponding to this phase blood vessel location information is information expressing a vein or information expressing an artery.

It should be noted that regarding the above programs, functions that can be realized only by hardware are not included in the functions realized by the above programs. For example, functions that can be realized only by hardware such as a modem and interface cards in an obtaining part configured to obtain information and a display configured to display information are not included in the functions realized by the above programs.

Further, the number of computer that executes this program may be one or more. That is, centralized processing may be applied, or alternatively, distributed processing may be applied.

Figure 31:
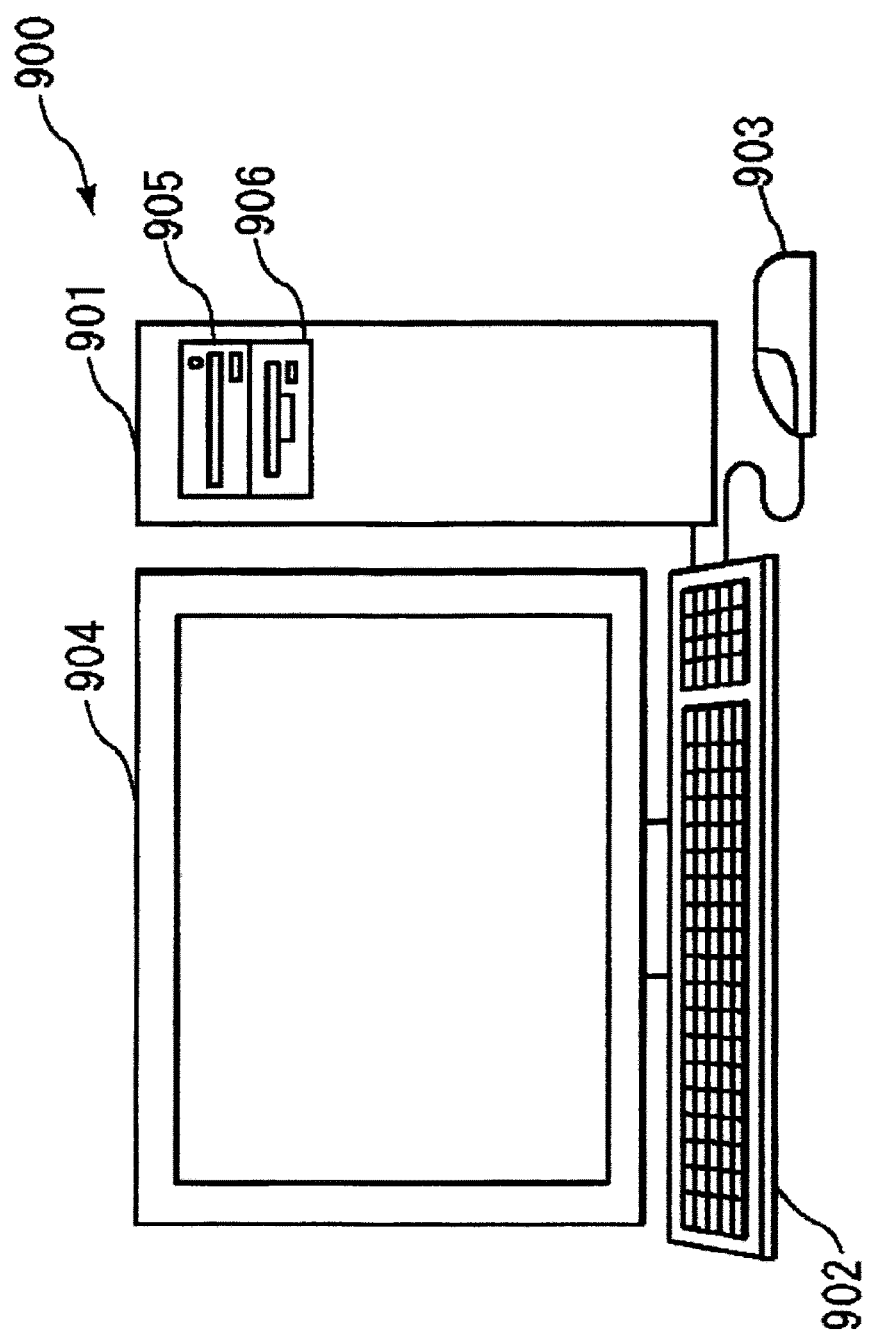
FIG. 31 is a schematic diagram showing an example of the appearance of a computer that realizes an image displaying apparatus of the present embodiment.

FIG. 31 is a schematic diagram illustrating an example of the appearance of a computer that realizes an image displaying apparatus according to the above embodiment. The above embodiment may be realized by computer hardware and computer program executed by the computer hardware.

In FIG. 31, the computer system 900 is provided with a computer 901 including CD-ROM (Compact Disk Read Only Memory) drive 905 and FD (Floppy (registered trademark) Disk) drive 906, a keyboard 902, a mouse 903, and a monitor 904.

Figure 32:
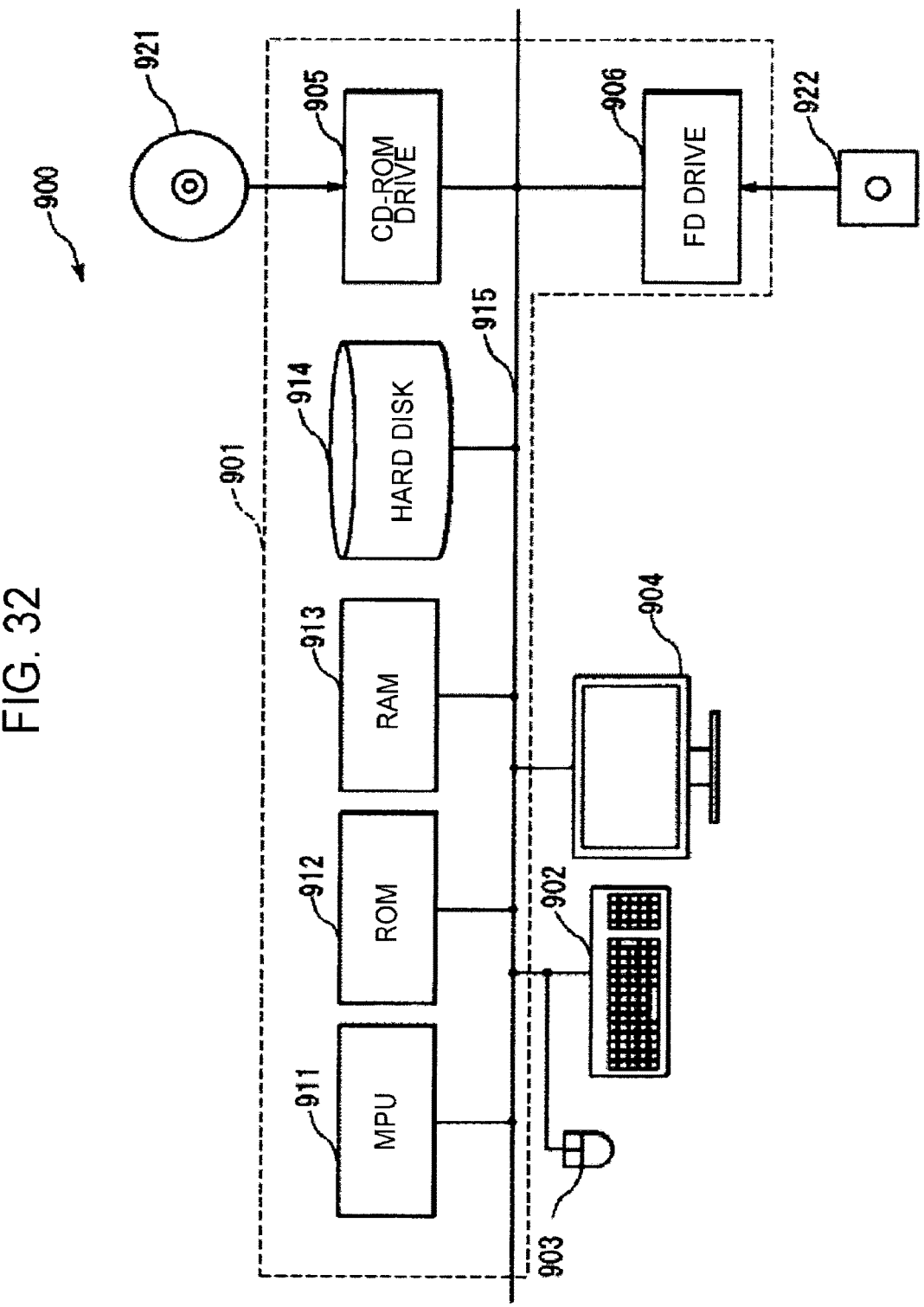
FIG. 32 is a diagram showing an example of an internal configuration of the present embodiment.

FIG. 32 illustrates internal configuration of the computer system 900. In FIG. 32, in addition to the CD-ROM drive 905 and FD drive 906, the computer 901 includes MPU (Micro Processing Unit) 911, ROM 912 for storing programs such as a boot-up program, RAM (Random Access Memory) 913 that is connected with the MPU 911, temporally stores commands of application programs and provides a temporally storing space, hard disk 914 that stores application programs, system programs and data, and bus 915 that connects the MPU 911, ROM 912 etc. with each other. It should be noted that the computer 901 may include a network card (not illustrated) that provides connection to LAN.

Programs that cause the computer system 900 to execute functions of an image displaying apparatus and so on according to the above embodiments may be stored in CD-ROM 921 or FD 922, inserted into the CD-ROM drive 905 or FD drive 906, and/or transmitted to the hard disk 914. Instead of these, the programs may be transmitted to a computer 901 via a network (not illustrated), and/or stored in the hard disk 914. At the time of execution, a program is loaded onto the RAM 913. It should be noted that a program may be directly loaded from the CD-ROM 921, FD 922 or network.

It is not necessary for a program to include an operating system (OS) or third-party program and so on that causes the computer 901 to execute functions of an image displaying apparatus and so on according to the above embodiments. A program may include only part of commands for calling appropriate functions (modules) in a controlled mode and obtaining desired results. Since ways of operations of the computer system 900 are widely known, detailed description is omitted.

The combination of the image displaying apparatus 1000 of the present embodiment and the optical image measuring apparatus of the above embodiment may be regarded as a measuring system, for example.

An image displaying apparatus according to the present embodiment is suitable as an apparatus etc. that displays multiple images acquired for a living body, and in particular, useful as an apparatus etc. that displays multiple images related to one site in a living body acquired using OCT and the like.

EXPLANATION OF SYMBOLS 1 fundus observation apparatus (optical image measuring apparatus)
2 retinal camera unit
10 illumination optical system
30 imaging optical system
31 focusing lens
31A focus driver
41 optical path length changing part
42 galvano scanner
50 alignment optical system
60 focus optical system
100 OCT unit
101 light source unit
105 optical attenuator
106 polarization controller
115 CCD image sensor
200 arithmetic and control unit
210 controller
211 main controller
212 storage
220 image forming part
221 cross sectional image forming part
222 phase image forming part
230 image processor
231 blood vessel region specifying part
232 blood flow information generating part
233 gradient calculating part
234 blood flow velocity calculating part
235 blood vessel diameter calculating part
236 blood flow amount calculating part
237 cross section setting part
240A display
240B operation part
E eye
Ef (eye) fundus
LS signal light
LR reference light
LC interference light
1000 image displaying apparatus
1011 cross sectional image storage
1012 phase image storage
1013 blood flow information storage
1014 living body image storage
1015 phase blood vessel management information storage
1016 cross section blood vessel management information storage
1017 blood vessel management information storage
1018 change operation receiving part
1019 blood vessel classification designating operation receiving part
1020 blood vessel classification management information storage 1021 blood vessel classification management information accumulating part
1022 display

What is claimed is:

1. An image displaying method executed by using: a cross sectional image storage configured to store a cross sectional image group including multiple cross sectional images each of which is associated with time and expresses a cross section intersecting at least one blood vessel of a living body; a phase image storage configured to store a phase image group including multiple phase images each of which is associated with time and expresses chronological variation of phase difference at a cross section intersecting at least one blood vessel of the living body; a blood flow information storage configured to store a blood flow information group including multiple blood flow information each of which is related to blood flow in a blood vessel of the living body and is associated with time; a display; and a change operation receiver that includes an input device to receive a user's input, comprising:
   a display step in which the display synchronously displays a cross sectional image included in the cross sectional image group and a phase image included in the phase image group using time associated with the cross sectional image and the phase image, and displays a blood flow image that expresses multiple blood flow information, from among the blood flow information included in the blood flow information group, associated with time within a period including time associated with the cross sectional image and the phase image that are being displayed; and
   a change operation receiving step in which the change operation receiver receives a change operation for changing display of one of the cross sectional image, the phase image and the blood flow image that are displayed by the display step, wherein
   in the display step, the display performs the same change as the change corresponding to the change operation to the cross sectional image, the phase image and the blood flow image that are displayed in the display step.

2. An image displaying method executed by using a cross sectional image storage configured to store a cross sectional image group including multiple cross sectional images each of which is associated with time and expresses a cross section intersecting at least one blood vessel of a living body; a phase image storage configured to store a phase image group including multiple phase images each of which is associated with time and expresses chronological variation of phase difference at a cross section intersecting at least one blood vessel of the living body and each of which is acquired based on detection results of interference light used for acquisition of a cross sectional image; and a display, comprising:
   obtaining a time corresponding to one of a cross sectional image included in the cross sectional image group and a phase image included in the phase image group;
   synchronizing the one of the cross sectional image included in the cross sectional image group and the phase image included in the phase image group based on the obtained time; and
   synchronously and superposedly displaying, on the display, the one of the cross sectional image included in the cross sectional image group and the phase image included in the phase image group using the obtained time associated with the cross sectional image and the phase image.

3. An image displaying method executed by using: a living body image storage configured to store a living body image acquired by photographing a living body; a blood vessel management information storage configured to store blood vessel management information including blood vessel location information that expresses location of at least one blood vessel in the living body image and blood vessel identification information corresponding to this blood vessel; a phase image storage configured to store phase management information that includes a phase image group including multiple phase images each of which is associated with time and expresses chronological variation of phase difference at a cross section intersecting at least one blood vessel of the living body and blood vessel identification information of a blood vessel intersecting a cross section corresponding to the phase image group; a phase blood vessel management information storage configured to store phase blood vessel management information including phase blood vessel location information that expresses location of a blood vessel in the phase image and blood vessel identification information of this blood vessel; a display; a blood vessel classification designating operation receiver that includes an input device to receive a user's input; a blood vessel classification management information storage configured to store blood vessel classification management information including blood vessel identification information and blood vessel classification information that expresses whether a blood vessel is a vein or an artery; and dedicated circuits configured, or a processing device programmed to perform, as a blood vessel classification management information accumulator, comprising:
   a display step in which the display displays the living body image and a phase image included in the phase image group that is associated with one blood vessel identification information;
   a blood vessel classification designating operation receiving step in which the blood vessel classification designating operation receiver receives blood vessel classification designating operation for designating location of a vein or an artery in the living body image displayed by the display step; and
   a blood vessel classification management information accumulating step in which the blood vessel classification management information accumulator obtains blood vessel identification information corresponding to the location designated by the blood vessel designating operation, and accumulates, in the blood vessel classification management information storage, blood vessel classification management information including this blood vessel identification information and the blood vessel classification information that expresses whether the blood vessel designated by the blood vessel designating operation is a vein or an artery, wherein
   in the display step, the display obtains the blood vessel identification information and the phase blood vessel location information corresponding to the phase image displayed in the display step from the phase blood vessel management information, obtains the blood vessel classification information corresponding to this blood vessel identification information from the blood vessel classification management information, and displays the location expressed by the phase blood vessel location information corresponding to the blood vessel identification information of the phase image in a different display aspect from other locations, wherein the display aspect thereof depends on whether the blood vessel classification information corresponding to this phase blood vessel location information is information expressing a vein or information expressing an artery.

* * * * *